(12) United States Patent
Wiele

(10) Patent No.: US 11,529,256 B2
(45) Date of Patent: Dec. 20, 2022

(54) ASSEMBLY FOR TREATMENT PROVIDING NON-INVASIVE CONTROLLED POSITIONING AND MOVEMENT OF A PATIENT'S JAW

(71) Applicant: Gary B. Wiele, Glendale, MO (US)

(72) Inventor: Gary B. Wiele, Glendale, MO (US)

(*) Notice: Subject to any disclaimer, the term of this patent is extended or adjusted under 35 U.S.C. 154(b) by 0 days.

(21) Appl. No.: 17/312,866

(22) PCT Filed: Dec. 11, 2019

(86) PCT No.: PCT/US2019/065622
§ 371 (c)(1),
(2) Date: Jun. 10, 2021

(87) PCT Pub. No.: WO2020/123592
PCT Pub. Date: Jun. 18, 2020

(65) Prior Publication Data
US 2021/0353451 A1    Nov. 18, 2021

Related U.S. Application Data

(60) Provisional application No. 62/778,143, filed on Dec. 11, 2018.

(51) Int. Cl.
*A61F 5/56* (2006.01)

(52) U.S. Cl.
CPC .................................. *A61F 5/566* (2013.01)

(58) Field of Classification Search
CPC ...... A61F 5/56; A61F 5/566; A61F 2005/563; A61F 7/36; A61C 7/08; A63B 71/085; A63B 2071/086; A63B 2071/088
See application file for complete search history.

(56) References Cited

U.S. PATENT DOCUMENTS 2,479,780 A   8/1948 Remensnyder
4,439,149 A   3/1984 Devincenzo
(Continued)

FOREIGN PATENT DOCUMENTS

CN   205094756 U   3/2016
KR   20110006263 U   6/2011
(Continued)

OTHER PUBLICATIONS

Corresponding Canadian Patent Application No. 111024W-1 Search Report, dated Jul. 22, 2021.
(Continued)

*Primary Examiner* — Camtu T Nguyen
(74) *Attorney, Agent, or Firm* — Sandberg Phoenix & von Gontard PC

(57) ABSTRACT

An oral treatment assembly providing a plurality of medical treatments of a patient that are non-invasive and in particular, provides new methods for treating jaw related medical conditions of a patient through predetermined positioning and controlled or guided movement of a patient's mandible and therefore their mandibular condyles during use, wherein the assembly includes an upper and lower assembly each defining transition portions having a reverse cut angle that extends downward from the posterior forward to the anterior, and where each are configured to selectively engage to restrict the retrusion of the mandible relative to the maxilla and to position the mandible relative to the maxilla downward and in some embodiment slightly forward in a caregiver defined treatment position and having a caregiver defined treatment movement area thereabout. Since the reversed cut angle contains two vectors it also discourages involuntary dropping of the mandible relative to the maxilla.

37 Claims, 18 Drawing Sheets

(56) References Cited

U.S. PATENT DOCUMENTS

| | | | |
|---|---|---|---|
| 4,509,918 A * | 4/1985 | Clark | A61C 7/36 433/5 |
| 4,619,609 A | 10/1986 | Clark | |
| 4,901,737 A | 2/1990 | Toone | |
| 4,969,822 A | 11/1990 | Summer | |
| 5,003,994 A | 4/1991 | Cook | |
| 5,092,346 A | 3/1992 | Hayes et al. | |
| 5,117,816 A | 6/1992 | Shapiro et al. | |
| 5,267,862 A | 12/1993 | Parker | |
| 5,277,202 A | 1/1994 | Hays | |
| 5,313,960 A | 5/1994 | Tomasi | |
| 5,324,196 A * | 6/1994 | Magill | A61C 7/36 433/19 |
| 5,352,116 A | 10/1994 | West | |
| 5,409,017 A | 4/1995 | Lowe | |
| 5,427,117 A | 6/1995 | Thornton | |
| 5,443,384 A * | 8/1995 | Franseen | A61C 7/00 433/18 |
| 5,611,355 A | 3/1997 | Hilsen | |
| 5,642,737 A | 7/1997 | Parks | |
| 5,823,193 A | 10/1998 | Singer et al. | |
| 5,829,441 A | 11/1998 | Kidd et al. | |
| 5,868,138 A | 2/1999 | Halstrom | |
| 6,027,340 A | 2/2000 | Chun | |
| 6,036,488 A | 3/2000 | Williams | |
| 6,041,784 A | 3/2000 | Halstrom | |
| 6,055,986 A | 5/2000 | Meade | |
| 6,161,542 A | 12/2000 | Halstrom | |
| 6,241,517 B1 | 6/2001 | Williams | |
| 6,305,376 B1 | 10/2001 | Thornton | |
| 6,325,064 B1 | 12/2001 | Thornton | |
| 6,491,519 B1 | 12/2002 | Clark et al. | |
| 6,505,625 B1 | 1/2003 | Uenishi | |
| 6,516,805 B1 | 2/2003 | Thornton | |
| 6,604,527 B1 | 8/2003 | Palmisano | |
| 6,666,212 B2 | 12/2003 | Boyd, Sr. | |
| 6,729,335 B1 | 5/2004 | Halstrom | |
| 6,792,952 B2 | 9/2004 | Mauro | |
| 6,845,774 B2 | 1/2005 | Gaskell | |
| 6,877,982 B2 | 4/2005 | Williams | |
| 6,886,566 B2 | 5/2005 | Eubank | |
| 6,983,752 B2 | 1/2006 | Garabadian | |
| 7,146,982 B2 | 12/2006 | Mousselon et al. | |
| 7,178,529 B2 | 2/2007 | Kownacki | |
| 7,354,270 B2 | 4/2008 | Abolfathi et al. | |
| 7,458,811 B2 | 12/2008 | Abels et al. | |
| 7,559,328 B2 | 7/2009 | Eubank | |
| 7,730,891 B2 | 6/2010 | Lamberg | |
| 7,757,693 B2 | 7/2010 | Toussaint | |
| 7,766,016 B2 | 8/2010 | Orrico et al. | |
| 7,836,889 B2 | 11/2010 | Kusukawa | |
| 8,001,972 B2 | 8/2011 | Eubank | |
| 8,033,282 B2 | 10/2011 | Eubank | |
| 8,105,210 B2 | 1/2012 | Seybold | |
| 8,136,529 B2 | 3/2012 | Kelly | |
| 8,166,976 B2 | 5/2012 | Webster et al. | |
| RE43,459 E | 6/2012 | Boyd, Sr. | |
| 8,215,312 B2 | 7/2012 | Garabadian et al. | |
| 8,226,407 B2 | 7/2012 | Hanewinkel et al. | |
| 8,257,079 B1 | 9/2012 | Plowman | |
| 8,297,286 B2 | 10/2012 | Smernoff | |
| 8,459,989 B2 | 6/2013 | Keski-Nisula et al. | |
| 8,534,289 B2 | 9/2013 | Hernandez | |
| 8,550,816 B2 | 10/2013 | Hanewinkel et al. | |
| 8,646,455 B2 | 2/2014 | Webster et al. | |
| 8,708,697 B2 | 4/2014 | Li et al. | |
| 8,752,554 B2 | 6/2014 | Spainhower | |
| 8,783,260 B2 | 7/2014 | Remmers et al. | |
| 8,839,793 B2 | 9/2014 | Diaz | |
| D718,448 S | 11/2014 | Bedford et al. | |
| D718,449 S | 11/2014 | Bedford et al. | |
| 8,931,486 B2 | 1/2015 | Halstrom | |
| 9,237,940 B2 | 1/2016 | Koklu | |
| 9,597,164 B2 | 3/2017 | Li et al. | |
| 9,615,964 B2 | 4/2017 | Rogers | |
| 9,655,692 B2 | 5/2017 | Lucas | |
| 9,655,695 B2 | 5/2017 | Ross | |
| 9,655,768 B2 | 5/2017 | Vaska et al. | |
| 9,707,055 B2 | 7/2017 | Izugami et al. | |
| 9,730,831 B2 | 8/2017 | Keller | |
| 9,744,006 B2 | 8/2017 | Ross | |
| 9,820,882 B2 | 11/2017 | Liptak et al. | |
| 9,844,424 B2 * | 12/2017 | Wu | A61C 7/36 |
| 10,299,894 B2 | 5/2019 | Tanugula et al. | |
| 10,342,526 B2 | 7/2019 | Arden et al. | |
| 2003/0207224 A1 | 6/2003 | Lotte | |
| 2003/0217753 A1 | 11/2003 | Thornton | |
| 2005/0244781 A1 | 11/2005 | Abels et al. | |
| 2006/0014117 A1 | 1/2006 | Abels et al. | |
| 2006/0078840 A1 | 4/2006 | Robson | |
| 2006/0234179 A1 | 10/2006 | Wen et al. | |
| 2007/0023055 A1 | 2/2007 | Roth | |
| 2007/0028926 A1 | 2/2007 | Kotani | |
| 2007/0283967 A1 * | 12/2007 | Bailey | A61F 5/566 128/848 |
| 2008/0060659 A1 * | 3/2008 | Bonato | A61F 5/566 128/848 |
| 2008/0072915 A1 | 3/2008 | Nelissen | |
| 2008/0102414 A1 | 5/2008 | Abels et al. | |
| 2008/0138755 A1 | 6/2008 | Jansheski et al. | |
| 2008/0190437 A1 | 8/2008 | Hervy-Auboiron | |
| 2009/0178684 A1 | 7/2009 | Greenburg | |
| 2010/0065066 A1 | 3/2010 | Hamburg | |
| 2010/0065067 A1 | 3/2010 | Lee | |
| 2010/0154802 A1 | 6/2010 | Fuselier | |
| 2010/0269835 A1 | 10/2010 | Thornton | |
| 2010/0316973 A1 | 12/2010 | Remmers et al. | |
| 2011/0005526 A1 * | 1/2011 | Garabadian | A61F 5/566 128/848 |
| 2011/0005527 A1 * | 1/2011 | Andrew | A61C 7/36 128/848 |
| 2011/0220125 A1 | 9/2011 | Van Dyke et al. | |
| 2011/0308531 A1 | 12/2011 | Grosky | |
| 2013/0014765 A1 | 1/2013 | Meade | |
| 2015/0007830 A1 * | 1/2015 | Remmers | A61B 5/4818 128/848 |
| 2015/0079531 A1 | 3/2015 | Heine | |
| 2015/0157491 A1 * | 6/2015 | Hofmann | A61F 5/566 128/848 |
| 2016/0367394 A1 | 12/2016 | Wagner | |
| 2017/0035533 A1 | 2/2017 | Ross | |
| 2017/0143537 A1 | 5/2017 | Kim et al. | |
| 2017/0202644 A1 | 7/2017 | Ross | |
| 2017/0209238 A9 | 7/2017 | Tanugula et al. | |
| 2017/0231723 A1 | 8/2017 | Lucas | |
| 2017/0273819 A1 * | 9/2017 | Shim | A61F 5/566 |
| 2018/0078344 A1 * | 3/2018 | Falkel | A61C 7/36 |

FOREIGN PATENT DOCUMENTS

| | | |
|---|---|---|
| KR | 101706648 B1 | 2/2017 |
| WO | 2011146419 A1 | 11/2011 |
| WO | 2018064772 A1 | 4/2018 |

OTHER PUBLICATIONS

Search Report to corresponding PCT/US2019/065622 dated Feb. 20, 2020.

Written Opinion to corresponding PCT/US2019/065622 dated Feb. 20, 2020.

DynaFlex Dorsal—DynaFlex, Dorsal Appliance, https://www.dynaflex.com/dental-sleep-laboratory-devices/dorsal/, 2018.

DynaFlex Dorsal AirPlus, Dental Sleep Medicine, "Anti Snoring and Sleep Apnea Devices", https://dynaflex.com/dental-sleep-med/sleep-appliances/dorsal-airplus/, 2014.

DynaFlex Dorsal Device, "Anti Snoring and Sleep Apnea Devices", https://dynaflex.com/dental-sleep-med/sleep-appliances/dorsal-appliance/, 2014.

(56) References Cited

OTHER PUBLICATIONS

Extended European Search report for corresponding European patent application No. 19895405.9, dated Jan. 7, 2022.

* cited by examiner

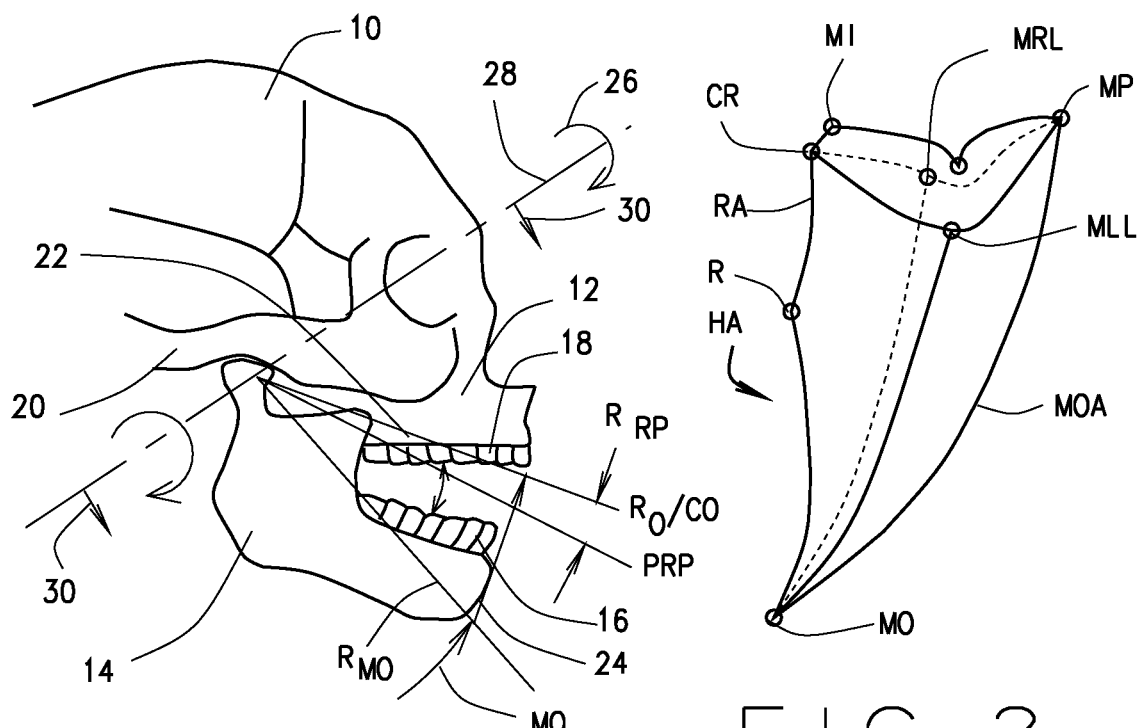
FIG. 1
FIG. 2
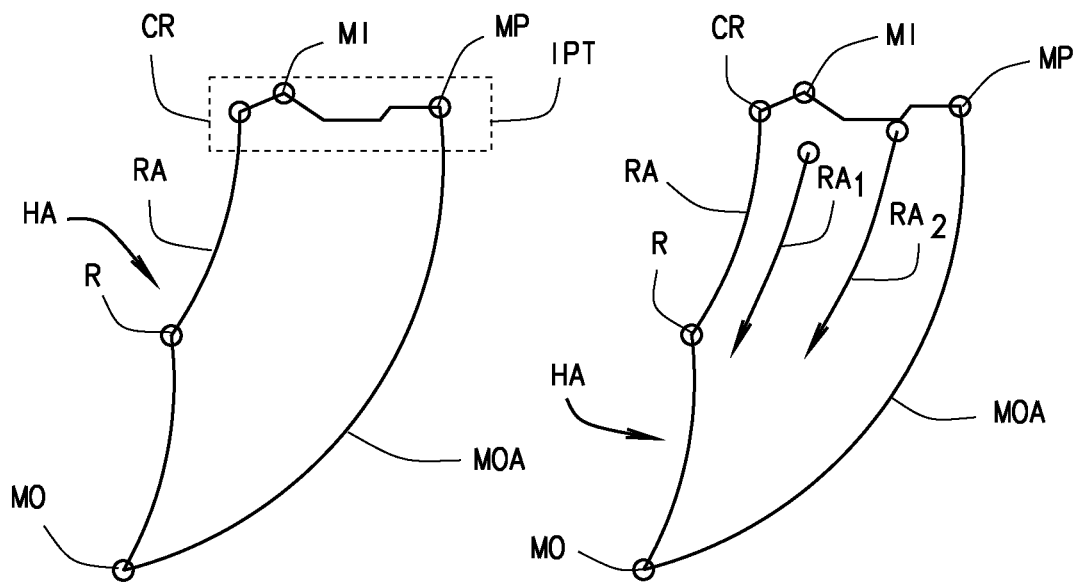
FIG. 2A
FIG. 2B

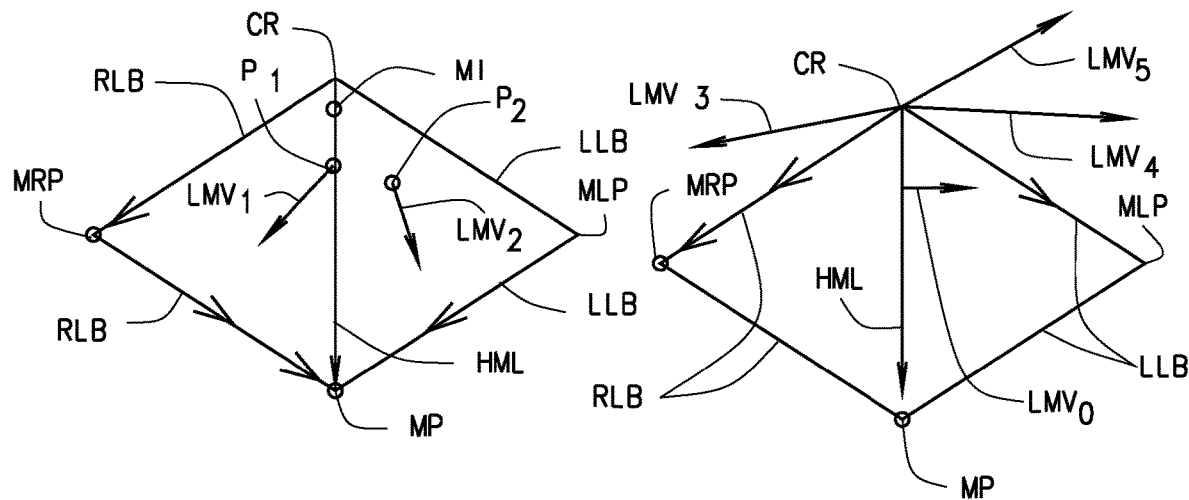
FIG. 2C
FIG. 2D
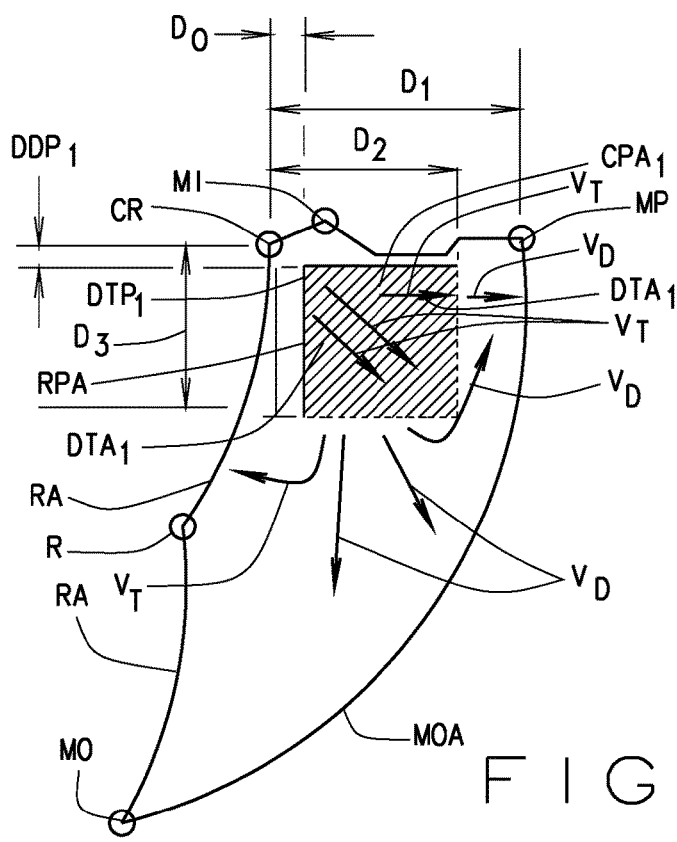
FIG. 3A

ASSEMBLY FOR TREATMENT PROVIDING NON-INVASIVE CONTROLLED POSITIONING AND MOVEMENT OF A PATIENT'S JAW

CROSS-REFERENCE TO RELATED APPLICATIONS

This application is a U.S. 371 National Phase Application of PCT Application This application claims the benefit of U.S. Provisional Application No. 62/778,143, filed on Dec. 11, 2018; each disclosure of which is incorporated herein by reference.

FIELD

The present disclosure relates to medical treatment of a patient through non-invasive use of a jaw control oral treatment assembly, and more specifically, to oral assemblies such as appliances and methods for treating jaw related medical conditions of a patient through predetermined positioning and controlled movement of a patient's mandibular condyles during use of the presently disclosed oral treatment assemblies.

BACKGROUND

The statements in this section merely provide background information related to the present disclosure and may not constitute prior art.

Referring to FIG. 1, a human skull 10 defines a maxilla 12, and a mandible 14. The mandible 14 that holds the lower teeth 16 is flexibly attached to the maxilla 12 that holds the upper teeth 18. The mandible 14 moves relative to the maxilla 12 during mastication, speech, swallowing, breathing/respiration, facial expressions, relaxation such as sleep, and clenching, as well as forced movements from outside forces on the mandible 14. During chewing (mastication) as well as other jaw movements by a person such as talking, the muscles of mastication are responsible for movement of the mandible 14. The mandible 14 is also connected to the temporal bone 20 of the skull 10 via the temporomandibular joint (TMJ) 22, which is an extremely complex joint that permits movement of the mandible 14 in all planes. The classic muscles of mastication span from the skull 10 and onto the mandible 14, thereby allowing for jaw movements during contraction. Factors that regulate the movement and motion of the mandible 14 include, by way of example, these jaw muscles of mastication, and accessory muscles, their neurology, dental occlusion, mandibular condyles, ligaments, tendons, glenoid fossas, and mensisci (discs), articular disc that is a fibrous plate (fibrocartilage bi-concave meniscus), the temporomandibular joint (TMJ) 22, all of which are referred herein collectively as "Jaw Anatomy Factors" JAF.

As illustrated in FIG. 1, the mandible 14 is in an opened mouth position wherein the mandible 14 moves downward along arc 24, which includes in part, a rotation RA 26 about a translatable intercondylar axis IA 28. As shown, if the mandible 14 is fully closed, the mandible 14 is in jaw position $R_O$, which is also referred to as the habitual intercuspal position, also referred to as centric occlusion CO. In position $R_O$/CO, referred hereinafter as CO, the mandible 14 is positioned adjacent to the maxilla 12 where the upper teeth 18 and lower teeth 16 of the mouth are fully engaged. In position CO, that is, the upper teeth 18 and lower teeth 16 are typically in uniform contact on all sides resulting in the mandible 14 being position at its closest position to the maxilla 12. Further, in position CO the condyles (not shown) are positioned within the glenoid fossa (not shown).

When the mandible 14 slightly opens, which can be the rest position (often referred to as the physiologic rest position PRP), the mandible rotates downward around intercondylar axis IA (also referred to as the hinge axis) as shown as rotation $R_{Rp}$. This movement can also include in some patients an inferior vertical drop. This slightly open position PRP results in the lower teeth 16 rotating downward and separating from the upper teeth 18 When the mouth opens further, such as shown in the position of FIG. 1, the mandible 14 can open to a maximum jaw opening position MO, also shown as $R_{MO}$.

For the mandible 14 to move from rest position PRP at CO to the maximum open position MO, the condyles of the mandibular 14 not only rotate further, but also shift forward protrusively relative the glenoid fossa, as the basic movement of the mandible 14 is not only rotational about the intercondylar axis IA, but is also translational. This translational movement 30 of the mandible 14 provides the ability of the mandible 14 to move forward (protrusively), downward, and/or laterally. Further, there is an articular disc that is a fibrous plate (fibrocartilage bi-concave meniscus) that divides the temporomandibular joint (TMJ) 22 into an upper and lower compartment, as well dividing other components of the JAF. This provides the TMJ 22 the ability to move in all three planes. In a normal functioning TMJ 22, opening of the mandible 14 is initiated by rotational movement to about 25 mm of opening, at which point PRP translational movement, or sliding, or protrusive condylar travel enables interincisal opening of the mandible 14 to about 50 mm. When a patient has a translational functional problem, such as a disc or arthritic issue, the patient will still be typically able to utilize the rotational function of the TMJ 22 and open to approximately 25 mm. This is a survival mechanism. The TMJ 22 is also capable of an initial majority translational movement followed by a majority rotational movement.

As noted, the mandible 14 moves laterally relative to the maxilla 12 based on a combination of the JAF factors including the lateral pyerygioid muscles. This lateral movement occurs due to the ability of the right and left side muscles and condyle associated therewith to operate somewhat independent of each other. To provide for the lateral movements, in some cases both sides (right and left) can contract in a lateral movement but by different relative amounts and in other cases one side can contract while the other side relaxes. Pure lateral movement of the mandible 14 occurs when the mandible 14 moves only laterally, with the condyle on one side translating and the condyle on the opposing side rotating.

The TMJ 22 is the anatomical area where the mandible 14 articulates with the skull 10 or cranium at the mandibular condyle/glenoid fossa. The TMJ 22 is a complex multi-axial joint where each side includes a condyle. Factors affecting the operation of this TMJ 22 include the occlusion (contact) of the upper teeth 18 with the lower teeth 16, the TMJ 22 with its ovoid condylar process, glenoid fossa, the masticatory and accessory muscles and their tendons, related ligaments and other JAF as referenced above. As discussed, the basic movements of the mandible 14 is either rotational or translational with rotation occurring with the hinged movement and translations occurring when the mandible 14 moves into a protrusive forward position, a lateral position, or a combination of the two. During opening, the first movement of the mandible is typically a rotational movement that is initially about the intercondylar axis IA with both condyles rotating within the glenoid fossa. Once the opening is larger than the maximum rotating position about the intercondylar axis IA, the condyles translate downward and forward from their most previous position, and can continue to rotate from this offset position (not merely rotating about the intercondylar axis IA). A protrusive movement occurs when the mandible 14 moves, via both the condyles, forward and downward along the anterior slope of the glenoid fossa toward the eminence. This movement of the mandible 14 can also be guided by the sliding of the lower anterior teeth incisal edges against the upper anterior teeth lingual concavities. This guided sliding is referred to either as protrusive guidance or anterior guidance (referred herein as anterior guidance).

By way of reference, it is well known that Posselt described the motions of the mandible in 1957 with simple diagrams, examples of which are shown in FIG. 2 and in FIGS. 2A, 2B, 2C, and 2D. As shown, Posselt's Envelope of Motion, for simplicity sake, provide Posselt's movement diagrams that illustrate the outer borders of the movement of a single point on the mandible 14 that is tracked during the full range of movement. This single point of tracking to the borders is typically the tracking of the incisal tip, which is the point between the two lower central incisors. Posselt's movement diagrams describes a compilation of complicated movements of rotation, translation, joint morphology and multiple muscular coordination of both right and left TMJ's and right and left muscles of mastication, at their typical outer or extreme border positions of such movements.

As shown in FIG. 2, Posselt's diagrams or Posselt's Envelope of Motion illustrate the movements of the mandible 14 at these outer borders of normal functioning joints. Of course, actual border movement diagrams will vary from patient to patient, and as such Posselt and the Posselt's diagrams described herein are only references to provide an illustrated perspective of the border movements of the mandible 14 of a single patient only by way of one example. Each patient will have their own border movements in all three dimensions (sagittal, vertical and horizontal) based on their own specific physiology. As such, in some patients, as will be discussed, some patients can have a mandible 14 whose outside border movements are considerably different or "non-traditional" movements, in that they can move outside of these typical Posselt's movement borders and along vectors that are non-traditional. Generally the traditional movements and borders are described herein for background on understanding the presently disclosed invention, and the applicability of such to non-traditional movements in some patients will also be described by way of examples where applicable. As such, for this disclosure and embodiments described herein, it is irrelevant as to what movements or collective joint positions are pathological or ideal for any one patient, as such is a professional caretaker's decision (that is typically an attending dental orthopedic practitioner) which is based on the facts and the needs of the treatment of the particular patient. The reference herein as in practice is to refer to Posselt's diagrams to describe and communicate what joint positions, locations, and jaw functions are allowed or disallowed or controlled with the current disclosed treatment assembly.

The traditional three dimensional Posselt's border movement diagram as shown in FIG. 2 can also be shown in each individual planes of motion. For the present disclosure's background, the sagittal plane of Posselt's border movements are shown in FIGS. 2A, and 2B, and the horizontal plane of Posselt's border movements are shown in FIGS. 2C and 2D. The movement path of the mandible during its movement in the sagittal and horizontal directions is illustrated to be within the borders of movement where outside of such borders in most patients, unless a non-traditional patient as discussed above, the mandible is not capable of further movement in that direction. These traditional border points define the border limitation of healthy or normal mandibular movements, and moving the mandible 14 to these points is therefore called the "border movements of the mandible 14", which includes centric relation, centric occlusion, hinge movement (also referred to as terminal arc of opening), and maximum jaw opening.

As shown in FIGS. 2A-2B by way of example, the sagittal movement border on the farthest right, which is referred to as the Maximum Opening Arc MOA represents the most protruded opening and closing stroke or movement of the mandible. At the bottom of FIG. 2A, the Maximum open position MO is the maximal mandibular opening point MO wherein the mandible 14 and therefore the mouth cannot be further opened. On the left side of this Posselt's diagram, the border line RA represents the movement of the mandible 14 that is the most retruded movement in that the mandible 14 cannot retrude backwards any further relative to the maxilla 12. Also shown in FIG. 2A, as will be described and discussed in more details with regard to the other Figures and discussion, are:

a. the border movement position of maximum protrusion MP;

b. the border position of maximum intercuspation MI;

c. the border position of centric relation CR (also referred to as CR or retruded contact position RCP);

d. the border point along maximum retruded arc RA (also referred to as Hinge Axis Arc HA) which is the border movement where the condylar heads remain in a reproducible position in the fossa, after which translation begins to occur. The is shown as position R, but also referred to as the Hinge Axis Terminating Point (HAT); and e. the maximum right lateral position MRL and maximum left lateral position MLL as shown in FIG. 2.

There are also additional descriptors identified within Posselt's Envelope of Motion. FIG. 2A illustrates the side plane view or sagittal view of Posselt's Border Movement. As shown at the top of FIG. 2A, the individual protrusive travel IPT plane is the border movement that tracks the front lower teeth 16 of the mandible 14 as they engage the front upper teeth 16 of the maxilla 12 during protrusive travel. The IPT plane includes the borders from the maximum protrusion MP to the maximum intercuspation MI illustrating the border movement that is due to occlusion. The IPT plane is shown in FIG. 2A at the top of the sagittal view and includes the border movements of the closed or nearly closed mandible. These include the border points of the maximum protrusion MP, maximum intercuspation MI, and centric relation CR (also referred to as the retruded contact position RCP). Also, it should be understood that in this sagittal view, the rotational arc RA for opening of the mandible 14 can be initiated from nearly any point along the IPT plane. As such, the illustrated borders do not restrict the point of the start of opening, but only illustrates the outermost borders of such movements. By way of example, a particular opening along a rotational arc RA can be initiated from border position CR, which is termed the Hinge Axis Arc HA which travels along the border as shown in FIG. 2B. However, as shown in FIG. 2B, opening can start at other positions that are not on the borders or movement extremes such as shown by rotational arcs $RA_1$ and $RA_2$, by way of examples. As shown more clearly in FIG. 2B, the mandible 14 is not limited to its movement to the defined Posselt's movement borders as illustrated by the diagrams, but the mandible 14 can typically freely move to and from any position with the Posselt's movement borders for each particular patient. The rotational movement arcs $RA_1$ and $RA_2$ only illustrate two opening movements within such borders and many other movements as to opening and closing are possible.

As shown in FIGS. 2A and 2B, the maximum intercuspation MI is the intercuspal position which is also referred to as the centric occlusion CO. This intercuspal position CO is the occlusal position of the mandible 14 at which the cusps of the teeth 12 of the upper arch fully interpose themselves ideally within the fossas of the teeth 16 of the lower arch. As known in the art, this intercuspation is not always applicable for all patients and in fact varies by person. However, every patient has an intercuspation position CO, which could be cuspid to cuspid tip for a particular patient. In such as case, the upper arch and the lower arch would both have the same planar positions. In most patients, this can be considered the starting point of the protrusive pathway, where the lower incisors are initially guided by the lingual concavity of the maxillary anterior teeth 18 or surfaces of the posterior teeth. As the incisors reach the edge-to-edge position, there is a gradual loss of posterior tooth contact which is reflected in Posselt's border movement diagram as shown in FIGS. 2A, and 2B as the initial downward slope of the border from MI to CR. One skilled the art will understand that these do not apply to all patients and may not be ideal, but are used herein by way of examples as these are often or commonly observed positions and interactions.

During the opening of the mouth, this changes when the mandible 14 is initially moved from the maximum intercuspal position MI during opening of the mouth or jaw. As introduced above with regard to FIG. 1, generally, during opening from the maximum intercuspal position MI, an opening movement (such as an opening movement of about 10 mm is often observed) can be made as a pure rotational movement of the mandible 14 about the intercondylar axis IA which is where the lower teeth 16 slightly separate from the upper teeth 18 which is due to a slight downward position of the mandible 14 through rotation about the intercondylar axis IA. The mandible 14 opens along the intercondylar axis IA with the condyles rotating within the glenoid fossa. This pure rotational movement, as shown in FIG. 2A, of the mandible stops at the terminal hinge axis position R, which is referred by some as the intercondylar axis terminating point HAT. This rotation about arc RA from point CR to point R is considered by those in the art to be the mandible opening movement wherein the condylar moves purely rotationally and therefore in a reproducible retruded position with no anterior-inferior condylar translation. During this movement, the arc RA of the movement of the mandible 14 has its center of rotation passing through the heads of the intercondylar IA.

The further opening of the mandible 14 relative to the maxilla 12 past this position R, results in not only the rotation about the intercondylar axis IA, but also the translations as described above that includes the condyles moving from glenoid fossa by sliding downward and forward to a termination point usually defined by the horizontal surface of the articular tuberosity or the fibrous joint capsule.

As the mandible 14 continues to rotate, the intercondylar axis from which the mandible rotates is translated as compared to the intercondylar axis IA in the CR resting position by a shift wherein the mandible 14 translates downward from the maxilla 12, as well protrusively or outward. This is shown in FIG. 2A as the opening border defined by the rotational arc RA continues past the point R until the maximum mandibular opening point MO is achieved. As shown, due this translation, the curvature of the opening past point R is a different curvature as compared to the rotational arc from CR to R. This further "rotational" movement occurs when the head of the condyle rotates with the translated or gliding movement as a result of the articular disk moving with the condyles against the inferior surface of the glenoid fossa. As noted, the intercondylar axis IA can in essence translate with the movement of the articular disk and condyle movement. Translation occurs typically when the opening of the mandible is greater than 20 to 25 mm. This is shown in FIG. 2A as complimentary mandibular movement until the maximum opening MO is reached. This downward and forward movement of the mandible is enforced by the lateral pterygoid muscle with the maximal mandibular opening MO occurring with full anterior-inferior translation of the condylar heads. Opening movement of the jaw from the maximal mandibular opening point R to the maximum opening point MO requires translation of the condyles downward and forward from their most posterior position. A normal full jaw opening MO is about 50 millimeters as measured from edge of front lower teeth 16 to edge of front upper teeth 18. When measuring the vertical range of motion, the measurement, in some circles, is adjusted for the overbite. For example, if the measurement from the edge of the front lower teeth 16 to the edge of the front upper teeth 18 is 40 millimeters and the overbite is 3 millimeters, then the jaw opening JO is about 43 millimeters.

The reverse occurs during closing of the jaw. During closing, the mandible 14 rotates back around the intercondylar axis IA and translates upward and backward until the first of the teeth 16, 18 come into contact which is where the upper teeth 18 and lower teeth 16 first contact.

FIG. 2A also illustrates the border movement of maximum protrusion by the border arc MOA on the right side from the maximum open position MO to the closed positioned of maximum protrusion MP.

FIGS. 2A and 2B have addressed the sagittal plane movements. FIGS. 2C and 2D illustrate exemplary horizontal plane of Posselt's border movement diagrams that include the lateral and forward movement vectors. The lateral and forward vectors are the movements of the mandible 14 that are most observable in the horizontal plane. If one TMJ 22 is stationary from a translating aspect, then rotates, and one joint translates fully, the one TMJ 22 rotates and the other translates, that is reflected by the traditional border vectors in the horizontal Posselt's diagrams of FIGS. 2C and 2D. As shown in FIG. 2C, the borders for the left and right lateral movements LLB and RLB, respectively, in the horizontal plane are illustrated in this example as starting at the border point of centric relation CR, which is the retruded contact position RCP as described above. The horizontal border movements shown on the right and the left which are referred to as the border arcs for Right Lateral Border RLB with the maximum lateral position being the Maximum Right Lateral position MRP, that reaches a maximum left lateral position at point MLP where after such further forward movement towards the MP laterally moves toward the right. Similarly on the other side Left Lateral Border LLB with the maximum lateral position being the Maximum Left Lateral position MLP, wherein after further forward movement of the mandible 14 moves the mandible 14 to the right towards the maximum protrusion MP.

If and when there is perfect coordination and morphology during a protrusive or forward event, the horizontal movement positioning will be a straight line arc, or horizontal midline HML. As shown in the middle of the horizontal vector plot of FIG. 2C, within the borders of horizontal movement, at the center is a horizontal movement midline HML. The horizontal midline HML is in the center of the horizontal movement the Posselt diagram as it is the horizontal movement where there is only forward movement of the mandible 14 from the point CR to the maximum open position MP and no movement laterally. This is the movement vector where the mandible 14 translates in a forward direction equally on both the right and left sides in synch. As such, in view of FIG. 2C it can be seen that any lateral movement is shown by example lateral movement vectors $LMV_1$ and $LMV_2$, with $LMV_1$ illustrating a right lateral movement and $LMV_2$ illustrating a left lateral movement. For further examples, each of these exemplary lateral movement vectors $LMV_1$ and $LMV_2$ start at a different horizontal (forward and lateral) starting position, with $LMV_1$ laterally sliding to the right side while moving further forward, but starting at a forward point $P_1$ on the HML. As a different example, $LMV_2$ illustrates a lateral slide to the left side, but starting at a jaw position $P_2$ that was already in a forward and left lateral position. $LMV_2$ movement vector illustrates a movement from $P_2$ that is both forward and further to the left. As such, from FIG. 2C it is clear that the horizontal movement vector illustrates that movement of the mandible relative to the maxilla both forward and laterally to the left and right sides of the HML during opening and manipulation of the mandible.

The lateral movement and therefore lateral vector that deviates from the HML in the traditional horizontal Posselt's border movement diagram of FIG. 2C is produced since the movement of the mandible 14 is a compilation of the two TMJs 22 translating and rotating simultaneously. However, as addressed above, there are instances in some patients where the horizontal and in particular the lateral movement is "non-traditional." FIG. 2D illustrates a horizontal Posselt's diagram of a patient where the mandible 14 can move laterally to the right or left with considerably less forward movement as shown by exemplary right lateral movement vector $LMV_3$. In some patients very little to no forward movement occurs but the mandible 14 can move laterally as shown by left lateral movement vector $LMV_4$. Further, in some patients, the mandible can move laterally to one side and actually retrude backwards along a vector that is retruded from the patient's border point of centric relation CR, which is the retruded contact position RCP as shown by vector $LMV_5$. As each of these is outside of the traditional horizontal Posselt's movement borders, these are referred to as non-traditional movements that occur with some patients.

In view of this background description of the movements of the mandible 14, when the geometry of the front teeth provides anterior guidance that prevents the back teeth from contacting when the mandible 14 is in the forward protruded position. This is generally accepted as good because there is a proprioceptive feedback loop that decreases muscular clamping. Without anterior guidance provided by the front teeth, the molars are likely to contact or hit in ways that generate undesired oblique forces that can also be increased forces.

It should be understood, that the resting position of the TMJ 22 is not when the patient's teeth are biting together or fully occluded. Rather, the muscular balance and proprioceptive feedback provides that the physiologic rest for the mandible is the physiologic rest position PRP, which is not equivalent to the point of maximum intercuspation MI. The PRP creates an inter-occlusal clearance or freeway space ($R_O$), which is usually 2 to 4 mm between the upper teeth 18 and the lower teeth 16. In the physiologic rest position PRP, the mandible 14 is at rest in an upright position with the condyles being in an unstrained and neutral position within the glenoid fossae. This position can usually be sustained by a patient as it is comfortable and takes little muscle control. The physiologic rest position PRP is unstrained or neutral as the various forces acting on the mandible 14 are equalized or in equilibrium enabling the jaw muscles to be relaxed. The physiologic rest position PRP is not determined by the teeth 16, 18 or occlusion between the teeth 16, 18, but rather by the patient's muscles and the nature forces of gravity on the mandible 14. In the upright PRP position, the condyles are also anterior and inferior as compared to their centric relation CR positions and the teeth 16, 18 are spaced apart forming a gap or jaw opening R referred herein as $R_{PRP}$ as described above with regard to FIG. 1 The $R_{PRP}$ is often referred to as the inter-occlusal space, freeway space, or wedge space.

It should also be noted, the industry varies with what is considered a retrusive/protrusive ideal, and the opinion varies concerning which particular application. In one embodiment, such as for use in an airway stabilization treatment, protrusive maximum would be about 60% of the maximum protrusive range of motion for the patient. It should be noted that in industry practice, there is considerable variance as to what is the "ideal" vertical dimension of occlusion for any patient. For the present disclosure, a liberal vertical maximum is described and defined herein at 70% of the rotational capacity of the opening function of the mandible 14.

As described above, the complexity of the movements of the mandible 14 enables the human jaw to perform its many tasks from talking to chewing. However, this complexity also can create or be related to problems wherein individuals must be treated for a variety of different jaw related conditions, such as, by ways of examples, osteoarthritis improper bite, patient pain and suffering, displaced menisci, snoring, and sleep apnea. As such, there is a need for an oral treatment assembly that can be used by a caregiver for use by a patient to treat one or more disorders or conditions such as TMJ joint stabilization and/or healing, patient airway stabilization, training or retraining of the musculature involved in a lateral disclusion slide, and prevention of compression or certain movements.

Furthermore, while numerous methods, systems and assemblies such as oral appliances have been developed over the years to treat some of these various afflictions, the inventor hereof has found the existing systems have numerous limitations and setbacks during preparation by a caregiver, can be difficult for a patient to use, can restrict patient jaw control more than is required thereby often making them undesirable for some patients to use as prescribed. Further, the inventor hereof has found that none of the prior art assemblies can be used by a caregiver to be customized for use in simultaneous treating more than one patient condition or jaw infliction during a single treatment process as the prior art assemblies are primarily aimed only at a single patient condition such as sleep apnea, leaving the other conditions to be treated using other means or not being treated at all.

SUMMARY

The inventor hereof has succeeded at designing various embodiments of a new treatment assembly and the methods of use of an oral treatment assembly that are each capable of treating numerous patients' medical conditions all through controlled positioning and also controlled movement guidance of the mandible relative to the maxilla. Various embodiments and aspects of the treatment assembly and its use for methods of treatment include for each of a mandibular and maxillary an oral tray at least one or two pair of mating reverse-cut or angled transition portions that provides, based on caregiver determination for each particular patient, one or more features that include retrusion prevention jaw positions. In some embodiments, one or both of the mandibular and maxillary oral tray assemblies can include a block, and in some embodiments where both the mandibular and maxillary oral trays including blocks, such blocks provide for the mated mandibular and maxillary transition portions having a reverse-cut angle, which can be on one side or on both the right and left sides. In other embodiments, as will be described, the reverse-cut angled transition portions can be formed not by mandibular and maxillary blocks but by an upward extending front centered pedestal with a distal end that engages in an upward cavity formed from a downward extending skirt with interior bearing surface walls.

In various embodiments, the treatment assembly as described herein can selectively retain the mandible relative to the maxilla during use and prevent separation therefrom during a relaxed musculature or control and limit retrusive forces placed on the TMJ condyle/joint. In some embodiments, the prevention of jaw retrusion, that can include the mere prevention of mandible retrusion, can be effectively used to prevent TMJ joint compression, stabilize or treat a displaced TMJ disc, decrease or eliminate snoring, treat certain types of sleep disorders such as sleep apnea, and counteract CPAP mask forces. The inventor hereof has identified that retrusion prevention is often sufficient for holding the patient's airways open during sleep, which is different than the commonly believed required mandible advancement that requires or forces a mandible jaw advancement, which is generally implemented in the existing prior art assemblies and treatments. The presently disclosed treatment assembly and method of treatment, uses a reverse angled transition portion that defines new occlusal surfaces that allows for jaw protrusion and lateral movement by the patient during use even when preventing retrusion.

In some embodiments, the treatment assembly can be configured to provide for lateral guidance, which can provide for the reduction in muscular pressure exerted by the closing of the master and temporal muscles. Further, in some embodiments, the angle of the transition portion and its positioning can be configured to control condylar movement as will generally be described.

In some embodiments, the treatment assembly described herein can also include one or more of:

a. a protrusive discluder feature, such as an additional disclusion angled contact surface between the mandible and maxilla portions of the treatment assembly that can be the transition portions or otherwise that provides for predetermined controlled protrusive disclusion.

b. an anterior discluder feature, such as a separate or additional feature or angle (disclusion angle) that provides a predetermined controlled anterior disclusion of molars and premolars;

c. a lateral disclusion feature such as a lateral disclusion angle or surface or feature to the transition portion or to another feature that provides predetermined controlled lateral disclusion guidance of a patient's movement of the mandible during use of the treatment assembly.

d. selective positioning of the posterior teeth to be in occlusion or out of occlusion during treatment, or otherwise to select or change occlusal contact points during treatment by providing new occlusal surfaces that include or exclude "centric" contact points anterior or posterior of the transition portions that can be defined by the caregiver to provide a dividing line in the anterior-posterior direction.

In some embodiments, the combination of retrusion prevention, condylar travel control and control of the occlusion, the oral treatment assemblies have applications for preventing and treating numerous medical conditions as will be briefly described herein.

The various aspects and features of the present disclosure will be in part apparent and in part pointed out below in the detailed description.

It should be understood that various aspects of the disclosure may be implemented individually or in combination with one another. It should also be understood that the detailed description and drawings, while indicating certain exemplary embodiments, are intended for purposes of illustration only and should not be construed as limiting the scope of the disclosure.

BRIEF DESCRIPTION OF THE DRAWINGS

FIG. 1 illustrates a typical human skull and in particular the mandible (lower jaw) to the maxilla (upper jaw).

FIG. 2 illustrates Posselt's border movements of a typical or traditional mandible in the three planes of movement.

FIGS. 2A, 2B, 2C, and 2D illustrate Posselt's border movements of typical or traditional mandible planes of movement with the combination of FIGS. 2A, and 2B illustrating the movements in the sagittal plane and FIGS. 2C and 2D illustrating the movements in the horizontal plane.

FIG. 3, including FIGS. 3A and 3B, illustrates reference Posselt's diagrams for the sagittal plane and the horizontal plane, respectively, illustrating a condylar positioning area CPA for treatment using the oral assemblies according to various embodiments of the present invention.

FIG. 7, including

FIG. 8, including

FIG. 9, including

It should be understood that throughout the drawings, corresponding reference numerals indicate like or corresponding parts and features.

DETAILED DESCRIPTION

Figure 3B:
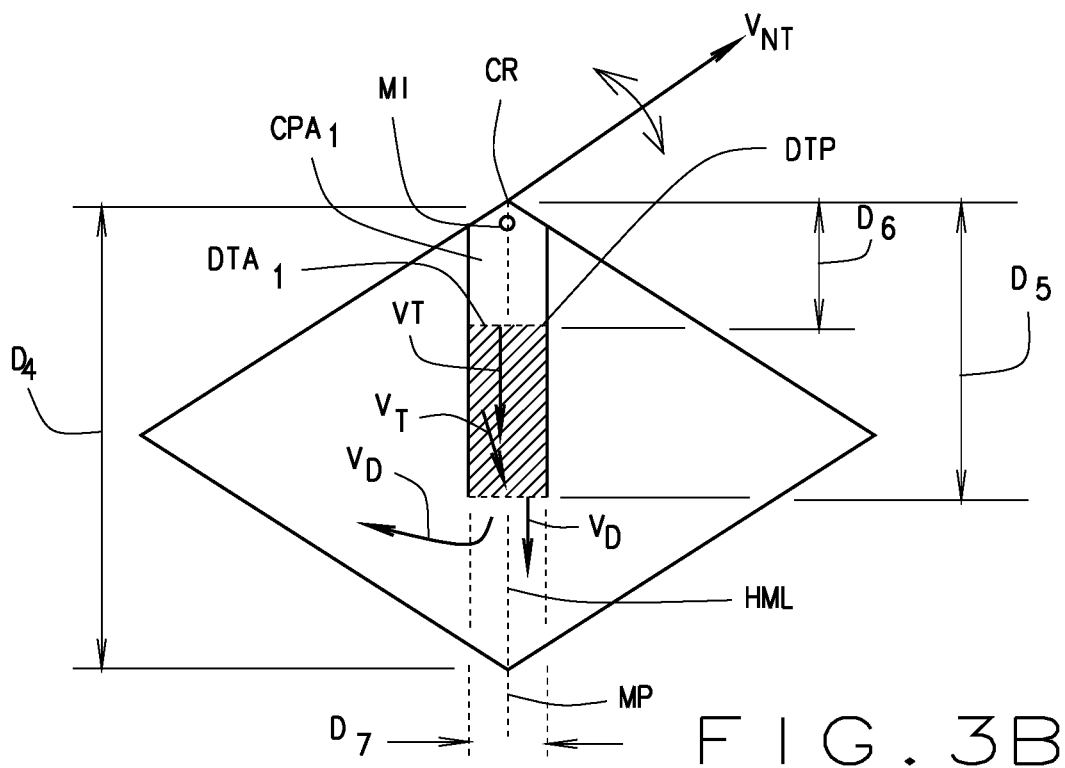

The following description is merely exemplary in nature and is not intended to limit the present disclosure or the disclosure's applications or uses.

The disclosure oral treatment assembly and the various exemplary embodiments herein is a jaw mandibular condyle control assembly. As disclosed, the various embodiments provide that during use by a patient, the oral treatment assembly disallows retrusion. As will be described herein, the oral treatment assemblies described herein generally provide for treatment by "retrusion prevention" or at least retrusion discouragement or disallowance (both of which are referred herein generally as retrusion prevention RP). The same oral treatment assemblies can also be used, alone or with retrusion prevention for treating other jaw issues of a patient as determined by a caregiver. In the sagittal view of the Posselt's movement diagram as described above, for any given patient a caregiver of the patient, based diagnostics of the patient's conditions and treatment, selects or creates a synthesized treatment starting point for the patient's mandible 14, which can be considered analogous to the maximum intercuspation MI for the patient. From that starting point, the position of the oral treatment assembly position or Determined Treatment Point DTP provides for disallowing retrusive movement of the mandible 14 during treatment using the oral treatment assembly as described herein. As will be described, in some embodiments, one or more embodiments of the oral treatment assembly described herein can provide for treatment that places the patient's mandible 14 in a position that maintains the mandible 14 in a position of relaxed muscles of mastication. In other embodiments and treatment uses, the oral treatment assemblies can be used during treatment use to train the muscles of mastication to move or operate along caregiver identified preferred vectors of movement, such as to correct improper movements or to provide such movements that are more relaxed or desirable for a particular patient.

In various embodiments, additional features of the oral treatment assembly can provide additional treatment capabilities that will enable the caregiver to provide to the patient user controlled and allowed movements that deviate from the DTP but within a determined treatment allowed movement area (determined treatment area) DTA that is an area defined relative to or in reference to Posselt's movements or diagram. The DTA is determined by the caregiver for each particular patient and can change during a course of treatment for each patient but results in the design and specification of one or more of the various features, structures and parameters of the oral treatment assembly 100 as described herein. By way of examples, as will be explained further, the oral treatment assembly 100 includes upper and lower transition portions 112, 116, upper and lower respectively that combined for the transition portion 109 that have features such as height and reverse angle selection, the shape, angles, and can provide new occlusal surfaces, and other features, dimensions, slopes and surface feature of the oral treatment assemblies 100. The DTA is a caregiver determined and assembly designed movement area of the assembly 100 that control curtained determined boundary movements within the DTA area, and that typically includes at one location along the DTA boundary the DTP. When designed by the caregiver, in most cases the DTA enables the patient to move their mandible 14 from the DTP along predetermined borders in certain directions and border paths that are guided or controlled along defined surface features of the caregiver determined oral treatment assembly. As will be described, these features can include guiding the horizontal and lateral boundary movements and also can include providing for controlled occlusion and disclusion with such vertical, horizontal, lateral, and protrusive movements. In some embodiments, new occlusal surfaces are provided by the disclosed oral treatment assembly 100. These oral treatment assemblies 100 can include features as will be described herein that also provide, by way of examples, the lateral aspect of anterior guidance, the protrusive aspect of anterior guidance, and total vertical dimension of occlusion, as well as others as will be described.

The oral treatment assemblies 100 as described herein provide at least the prevention of jaw retrusion as defined above. The inventor hereof has determined that, by way of example, the treatment of sleep apnea, the mere prevention of mandible 14 retrusion including in some cases the disallowance of retrusion, without requiring or forcing a mandible 14 to be advanced, as is generally the practice in the art, can be sufficient in many patients to hold the patient's airways open. In other treatment uses, the prevention of jaw retrusion can be utilized for treatment of a displaced disc TMJ 22 and for use with certain types of CPAP masks when treating sleep disorders.

As described herein, various embodiments of the oral treatment assembly 100 can be configured from upper and lower oral treatment assemblies 102, 104 when placed on the upper teeth 18 of the maxilla 12 and the lower teeth 16 of the mandible 14, respectively, to create a new occlusal surface that replaces during treatment the natural occlusal surface of the patient's natural teeth 16, 18. These new occlusal surface provided by the treatment assemblies 100 can include several new oral treatment assembly "artificial" occlusal surfaces (referred herein simply as "new occlusal surfaces") for occlusion during use of the assemblies, which can include, by way of example, a new anterior occlusal surface and separately a new posterior occlusal surface, or a combination thereof. As such, while a patient may have a defined pretreatment border movement area such as the above described by Posselt's border movements, during use of the oral treatment assembly 100, the oral treatment assembly 100 controls and can restrict certain border movements of the patient's mandible 14 that can start at the DTP and still allow free movement within the DTA under most common border movements during use, that can include occlusion. As noted herein, the caregiver can also configure the oral treatment assemblies to prevent certain types of occlusion during use of the tray.

Some embodiments of the oral treatment assembly 100 can be formed to have a pair of left and right transition portions 109 that can, in some embodiments, provide the new occlusal surfaces. For each such pair of transition portions 112, 116, the transition portion 109 transition portion 109 has an upper (maxilla 12) and a lower (mandible 14) transition feature that mate or otherwise engage during contact, that can include where specified by the caregiver the providing of the new occlusal surfaces, and that provides for caregiver determined selective positioning of the mandible 14 in the determined treatment position DTP relative to the maxilla 12 during static rest during use by the patient. In some embodiments, the oral treatment assembly 100 includes an upper tray assembly and a lower tray assembly, but can be formed by other suitable structures as well. The upper assembly can include upper assembly features, such as upper blocks, on one or both the right and left sides, with each customized by the caregiver defining the upper right and left transition portions and can include defining the a portion of the new occlusal surface. The lower assembly can include a mating lower transition portion that can also be formed on lower assembly features, such as lower blocks, also on the right and left sides and also with each customized by the caregiver defining the lower right and left transition portions that are configured to mate with the upper right and left transition portions thereby providing the mating or matching portion of the new occlusal surfaces. The oral treatment assembly's upper and lower assemblies can in some embodiments be configured to retain, through selectively engaged retention or coupling of the transition portions 112, 116, the mandible 14 relative to the maxilla 12 during treatment at the DTP while still enabling the patient to selectively move the lower jaw from the DTP within the DTA. This can include the patient moving the mandible 14 from the DTP protrusively (forward), laterally (side to side), as well as downwardly, each along a predetermined angle or vector from the borders defined by the DTA. Further, the oral treatment assembly 100 can control the movement of the mandible 14 during treatment so that each of the vectors of allowed movement from the border defined by the DTA cooperates with the allowed other directions and along their allowed vectors, or otherwise from the determined treatment position but within the DTA. Further, the oral treatment assemblies 100 can be configured to enable the patient to move their mandible 14 to both engage and disengage the lower transition portion 116 from the upper transition portion 112 for the placement and removal of the upper and lower oral treatment assemblies of the oral treatment assembly.

In some embodiments, the position and angle of the transition portions 112, 116 and their mating transition features that can form the new occlusal surfaces, among other features, are configured to move the mandible 14 forward from the patient's CR position or from the MI position to a coupled or retained position wherein the DTP positions the mandible 14. This forward titration is referred to as titrated mandibular advance. By way of just one example, the oral treatment assembly 100 can be configured to have transition portions 112, 116 having a DTP that is advanced forward in the horizontal plane as shown in FIGS. 2C and 2D, such as may be along the HML, but could be also be positioned to have a lateral offset from the HML. In one exemplary embodiment, the forward advance of the DTP can be about 60 percent of the maximum forward position of the mandible 14 relative to the maxilla 12 for the particular patient. In such an exemplary embodiment, the 60% titrated forward position of the mandible 14 relative to the static position when in the transition portion 112, 116 are in the engaged or mated position that can form the new occlusal surfaces and that provide cuspid and/or anterior guidance and other of the treatment features as described herein, while still enabling the patient with the ability to move the mandible 14 forward or laterally. As such, a reduction impact on the muscles of mastication can provide benefits to some patients as determined and provided by the caregiver.

In one embodiment, the transition portions 112, 116 of each oral treatment assembly 100 are configured by the caregiver so that the patient's eye teeth are touching. In such embodiments, the oral treatment assembly 100 can provide that the eye teeth prevent a side by side lateral movement of the mandible 14 relative to the maxilla 12 during use of the treatment assembly 100 at least when the patient's mandible 14 is in the DTP. In such embodiments, the transition portions 112, 116 of the oral treatment assemblies 100 not only prevent retrusion from DTP, but also prevent or control lateral movement (to the right or left). Further, the transition portions 112, 116 can be shaped in some embodiments to control the lateral movement along defined controlled lateral vectors during any patient induced forward movement of the mandible 14 from the DTP, within the DTA, especially where contact between the mated transition portions 112, 116 continues to occur.

In some embodiments, to provide for a secured mating of the transition portions 112, 116 at the DTP and in areas of the contact within the DTA, the transition portions 112, 116 are configured to have a reverse cut or reverse angle. A reverse angle, as will be explained in further details, provides that during the mating or coupling of an upper mating feature of the upper transition portions 112, 116 with the lower mating feature of the lower transition portions 112, 116, aids in the retaining the mandible 14 relative to the maxilla 12 in the DTP position and inhibits the involuntary lowering of the mandible 14. The reverse angle is a reverse cut each transition portion 112, 116 from the rear of the gum line of the upper teeth 18 of the maxilla 12 downward and forward to the crowns of the upper teeth 18 and continues downward and forward to the gum line of the lower teeth 16 of the mandible 14. The angle of the reverse angled transition portions 112, 116 from the rear upper position to the lower position is determined by the caregiver for each patient based on the identified treatment requirements for that patient. In some embodiments, a reverse angle of between about 22 degrees to one that is equal to or less than about 90 degrees, or slightly less such as 89 degrees relative to the occlusal plane can inhibit the involuntary down movement of the mandible 14 during use. In some embodiments and/or for some patients, this reverse angle RPA of the transition portion 109 has been found to be suitable to be about 90 degrees, or slightly less at about 90 degrees. On the low end while about 22 degrees can be suitable, it has also been found that about 30 degrees up to about 89 degrees is also suitable for some patients and some applications. However, such RPA reverse angle can also be dependent or impacted by the selection of the amount of forward titration of the determined DTP as well as other surface and other features of the transition portion 109 such as will be described herein.

In some embodiments, the determined RPA has been identified to be plus or minus of 10 degrees from the "about" 45 degree angle from the occlusal plane, and in some between about 22 and about 45%, which can be plus or minus 0 to 5 degrees. The angled cut of the transition portion 109, which is composed of the upper transition portion 112 and the lower transition portion 116, which in some embodiments can be formed using the mated twin blocks 120, 122 formed on oral dental assemblies, by way of one example can be an oral tray or can be another structure carrying means, that form the oral treatment assembly 100 can be configured by the caregiver based on position and angle of the RPA so as to control and/or limit condylar movement from the DTP and within the DTA that is a treatment area within that is a subset of Posselt's border movements during treatment use.

Of course, as understood by one of ordinary skill in the art in reviewing this disclosure, the reverse angle may be very slight, especially depending on the design and placement of the transition portions 112, 116 for the upper and lower assemblies, respectively. For example, as will be described in further detail below, the transition portion 109 can be configured to also form new occlusal surfaces that have occlusal surfaces with selectively determined location, height, and determined occlusal placement or occlusal prevention. One or both of the upper and lower transition portions 112, 116 can have transition portion surfaces 132, 134, respectively (i.e., upper transition portion surface 132, and lower transition portion surface 134) that are configured with increased friction or with additional engaging features such as lips or a lip and mating groove. Such additional features of the transition portions 112, 116 and the formed new occlusal surfaces can work in cooperation with the reverse angle of the transition portion 109 to selectively engage the transition portions 112, 116 at or near the DTP during treatment use. These additional transition portion 109 features can further restrict, prevent, control, or limit, in cooperation with the forward titration and the reverse angle, involuntary downward movement of the mandible 14. As will be described, where such additional transition portion 109 features are present, the amount of forward titration and the amount of reverse angle can be optimized by the caregiver to provide other desired effects such as relaxed muscles of mastication, or the training of such, rather than solely to only provide for the selectively held engagement of the transition portion 109 to prevent the involuntary downward movement of the mandible 14.

In some treatment design and uses, the transition portions 112, 116 such as formed new occlusal surfaces can be configured to provide anterior guidance which provides for a relative reduction in contraction of the muscles that compress the condyles against the glenoid fossa.

In some embodiments, the reverse angle of the transition portion 109 not only engages and retains or selectively couples the mandible 14 at the DTP that may be in a forward titrated position but when the transition portions are engaged, the reverse angle restricts or controls the downward movement of the mandible 14 relative to the maxilla 12. This restriction on the downward movement of the mandible 14 can restrict the involuntary opening of the patient's mouth during use. The prevention of the patient's mandible 14 from moving downward and rotating downward and backward can provide for the treatment use in some patients such as for treatment of sleep apnea when used by the patient during sleep.

Cuspid Guidance Feature

In some embodiments, the oral treatment assemblies can be configured to provide cuspid guidance (canine lateral or anterior guidance) which, during treatment use, can enhance the normal cuspid guidance to further guide the rear or posterior teeth apart during treatment use. The cuspid guidance feature of the oral treatment assembly can be configured, such as in the design of the transition portion 109 and directly adjacent to the transition portion 109, so that the mandible 14 is slid laterally or forward relative to the maxilla 12 during treatment thereby providing advanced molar separation during a mandibular sliding movement by the patient. As addressed above, the design configuration of the transition portions transition portion 109 and their transition features, such as the reverse angles and new occlusal surfaces, can be configured so that during use, the oral treatment assemblies 100 restrict and/or prevent the unintentional downward movement of the mandible 14 and with it the separation of the cuspids at the defined transition portion 109, which can be the position of relaxed musculature or control that limits the retrusive forces placed on the temporomandibular condyles (joints). However, during treatment use when the mandible 14 is protruded in a forward position, as addressed above, occlusion provided by the geometry of the anterior teeth 16, 18 separate the posterior teeth 16, 18 which forces the posterior teeth 16, 18 apart. This movement further forces the mandible 14 in a slight downward or open position.

The embodiments of the assemblies 100 enable the patient to selectively move the mandible 14 forward protrusively from the DTP and generally within the DTA during use. Of course, any intentional movement of their mandible 14 by the patient can exceed the forward and downward dimensions and control features provided by the oral treatment assembly 100 that are beyond the DTA. When such occurs, such as when the patient intentionally desires to disengage the engaged transition portion 109 of the oral treatment assembly 100 to remove either one or both of the upper and/or lower oral treatment assemblies of the oral treatment assembly 100, the patient can move their mandible 14 protrusively and then downward past the area of the DTA, which will enable the patient to disengage the transition portions 112, 116 and the engagement of the upper and lower oral treatment assemblies 100 and therefore the treatment use thereof.

In some embodiments, the transition portion 109 of the upper and lower oral treatment assemblies 100 can also be configured by the caregiver to allow and provide for cuspid or first bicuspid lateral guidance and/or anterior guidance. The caregiver may select embodiments where cuspid or first bicuspid lateral guidance and/or anterior guidance are provided in the design and configuration of the oral treatment assembly 100 for a particular patient to provide the patient with reduced muscular pressure or contraction that is exerted by, but not limited to, the masseter and temporalis muscles during the protrusive or lateral movement of the jaw. The provided cuspid or first bicuspid lateral guidance and/or anterior guidance can aid in the positioning of the mandible 14 that replaces the muscular pressure required by the patient to sufficiently fully close their mouth. Further, oral treatment assemblies 100 with cuspid or first bicuspid lateral guidance and/or anterior guidance can be used to train, or retrain the masseter, temporalis, and JAF during movement along caregiver defined vectors and disclusion angles during treatment use of the oral treatment assembly 100.

Retrusion Prevention

As addressed above, the transition portion 109 provide among other benefits, retrusion prevention RP by providing reverse or negative retrusion prevention RP relative to the occlusal plane in an anterior-posterior direction. As described above, the reverse cut or negative angle referred to as retrusion prevention angle RPA extends from the upper gum line that is often near the gum line of the posterior upper teeth 18, downward and forward towards the anterior lower teeth 16. The RPA of the engaged lower transition portion 116 with the upper transition portion 112 defines the amount of the forward mandible 14 movement required by the patient to engage and disengage the lower oral treatment assembly 100 from the upper oral treatment assembly 100. This reverse or negative angle RPA is in contrast to prior art systems that utilize a forward angle that requires muscular contraction and a camming-type action by the patient in order to engage and selectively couple the assemblies in the protrusive position during treatment use. As disclosed herein, the reverse or negative angle a slight muscular contraction by the patient is used to place the treatment assemblies into their treatment position and after placed in such position the patient's muscles can be relaxed and or "turned off" during treatment use as the negative angle RPA retains or couples the lower assembly 114 and therefore the mandible 14 relative to the maxilla 12 unless the patient specifically and intentionally moves the mandible 14. As also disclosed herein, even after being placed by the patient in the treatment position DTP, the patient is provided with caregiver controlled movements along the new occlusal surfaces as well as other movements that can provide the patient with increased movement for speech and other patient desired movements. The definition of the DTP and the selection of the RPA and its positioning enables the mandible 14 to stay coupled or engaged with the maxilla 12 without muscular contraction by the patient, due to the stretch memory in the jaw's muscles, ligaments, tendons and JAF.

The position of the transition portion 109s having the RPA along the occlusal plane from the posterior to the anterior teeth for a particular patient's oral treatment assembly 100 is determined by the caregiver for the particular patient, and can be located in any position as so determined necessary to provide the desired selection of treatments and therefore treatment features of the oral treatment assembly 100.

In various embodiments, the selection of the position of the transition portion 109 by the caregiver for the oral treatment assembly 100 is made so that the mandible 14 is positioned relative to the maxilla 12 at the caregiver's determined DTP when the oral treatment assembly 100 is used by the patient for treatment. However, unlike like many currently known oral assemblies, the presently disclosed assemblies 100 positions the mandible 14 relative to the maxilla 12 at a DTP but allows an amount of movement of the mandible 14 relative to the maxilla 12 in the DTA as determined by the caregiver. As described above the DTA provides a restricted or limited movement of the mandible 14 from the DTP retrusively, downward, and laterally. Further, as described herein, such movements can be controlled in that the caregiver can define the transition portion 109 the provides other treatment features and functions and wherein the oral treatment assembly also provides new occlusal surfaces that, while the transition portions 112, 116 are engaged or being engaged, control the movements of the mandible 14 relative to the maxilla 12 in different directions as described in this disclosure and as selected by caregiver for each particular patient's needs.

The oral treatment assembles 100 can be formed from oral assemblies that can cover all or just a portion of the lingual surfaces of the anterior teeth 16, 18. This can include covering only the crown of the anterior teeth 16, 18 or can extend downward with a skirt towards the gums. In some embodiments, the two opposing sides of the oral treatment assemblies 100 can be separate or connected using an arch or other body structure as known in the art or applicable to the patient. As will be described herein, each right side of a oral treatment assembly 100 that is composed of a right assembly set comprising a right upper assembly 110 and a right lower assembly 114, and a left upper assembly 110 and a left lower assembly 114, can be design by the caregiver to have different structure features, such as dimensions, angles and the like as described herein as each side may be configured to structurally operate differently in order to accomplish the overall determined treatment for a particular patient or that may vary over time for that particular patient.

After an evaluation of a particular patient by the caregiver, the caregiver initially defines the DTP for which the treatment assembly 100 will be designed. Further, the caregiver identifies and selects the treatments for the patient for which the particular oral treatment assemblies 100 will be used to treat. As noted above, the present oral treatment assembly 100, unlike those of the prior art, enable the caregiver to treat multiple patient conditions during a single treatment use, and therefore, each oral treatment assembly 100 can be designed to have more than one treatment feature. After the caregiver determines the treatments to be addressed through use of the oral treatment assembly 100 for a particular patient, the caregiver identifies the DTP and also designs the determined treatment movement area DTA. In some embodiments, this determined DTA provides for treatment of the patient by first placing the mandible 14 relative to the maxilla 12 at the DTP that keeps the jaw muscles relaxed. The DTP can also be defined by the caregiver to be a position that provides the patient with a caregiver determined treatment "idealized" bite relation of the mandible 14 relative to the maxilla 12. By way of example, a caregiver can determined an "idealized" bite relation of the mandible 14 relative to the maxilla 12 during treatment and use of the treatment assembly 100 that provides a caregiver determined "idealized" joint position airway. This is one example of the defining of the DTP at a position that provides for dual treatments, which is one of the benefits of the present treatment assembly 100 as compared to known treatment assemblies that are specifically designed and only capable of use for a single jaw related treatment.

Of course, when considering the selection of the DTP the caregiver also considers the controlled movements therefrom as to the provided or available DTA, which provides for further treatment through the controlling and possible training of one or more JAF such as the muscles of mastication by way of example, during patient movements. The selection of the DTP and the DTA area of controlled and allowed movements therefrom during treatment use that is completely different than other known prior art devices as such prior art devices effectively lock or clamp the patient's mandible 14 to the maxilla 12 during treatment use, which is undesirable. Furthermore, prior art devices do not provide for caregiver determined treatment lateral or anterior guidance. In contrast to the prior art, each embodiment of the presently disclosed oral treatment assembly 100 can be customized by the caregiver that provides the transition portion 109 and also in some embodiments, new occlusal surfaces that enables caregiver determined selective steady state positioning and temporary selective coupling retaining at the DTP and also allows movement therefrom as selected and designed by the caregiver. Further, by providing the determined treatment point DTP, and controlled vectors of movement along borders that define the DTA, not only does the oral treatment assembly 100 maintain the benefits of the caregivers determined treatment positioning, but enables the caregiver to provide other treatment to the patient such as through the training of the movements and vectors of movements of one or more JAF, including, but not limited to, the jaw muscles of mastication, the mandibular condyles, the ligaments, and the tendons.

While many different embodiments for implementing the described oral treatment assembly 100 are possible based on the present disclosure, three exemplary embodiments are shown in FIGS. 7, 8, and 9 that illustrate three different oral treatment assembly devices according to this disclosure.

These are by way of example, and other embodiments and implementations are considered to be within the scope of this disclosure and claims. Each of the three exemplary embodiments provides for upper and lower selectively engaging transition portions 112, 116 having a RPA providing retrusion prevention, and which also show by way of example other structural feature that provide other treatment features. As described herein, the positioning of the RPA prevents the retrusion of the mandible 14 backward beyond the caregiver determined DTP and that also selectively engages or couples the mandible 14 to the maxilla 12 by way of the RPA in a manner that prevents the mandible 14 from dropping away from the maxilla 12 during treatment by selectively restricting or inhibiting the unintentional downward movement of the mandible 14. As will be described, in some embodiments, the present inventor has identified that, contrary to the present prior art which focuses on advancement or protrusion of the mandible 14, many of which "lock" the mandible 14 to the maxilla 12 thereby inhibiting patient desired selective movement of the mandible 14 by the patient during use, such as for talking or otherwise. In some embodiments, the presently disclosed assemblies 100 and methods of treatment are focused on a caregiver determined DTP that can be selected by the caregiver to prevent retrusion that helps keep the jaw muscles relaxed, but also, while doing so provides for patient controlled and selected movements away from the DTP within the DTA in predetermined controlled movements protrusively, downwardly and laterally.

During practice of the present disclosure, while some patient's may differ and therefore will be some outlier applications, it is expected that for the majority of patients, the borders of the DTA for allowed lateral movement of the mandible 14 by the oral treatment assembly 100 will be determined to be from between 0 to about 3 mm from the "skeletal" midlines R-L and from the CR to 60% protrusive capacity. This area is defined on the top and right by the Posselt's border movement diagram, on the left by the vertical line or plane containing the ICP as shown if FIG. 3A, and the determined DTP point, and a horizontal line/plane that can contain, but is not required to contain, a swallow against resistance SAR point as shown by way of example in FIGS. 4C and 4D. FIGS. 3A, 3B, 4A, 4B, 4C and 4D illustrate a plurality of different exemplary DTA that can contain condyle positioning areas CPA such as shown as areas, $CPA_1$ in FIGS. 3A and 3B, $CPA_2$ in FIGS. 4A and $CPA_3$ in FIGS. 4B and 4C, each of which can be an area for condyle positioning for different patients based on an evaluation by a caregiver. Also as shown, for each patient the caregiver can define a DTP and DTA, which only by way of example and not limited thereto, is shown in these figures as the determined treatments points $DTP_1$ in FIGS. 3A and 3B, $DTP_2$ in FIGS. 4A, and $DTP_3$ in FIGS. 4B and 4C, as well as the determined treatment areas $DTA_1$, $DTA_2$, $DTA_3$, respectively. These examples DTAs are the determined and designed areas of allowed of selective movement by the patient for restricted or limited movement after the treatment assembly 100 has selectively coupled or otherwise retained (selective positioning and retaining referred to herein as coupling) the lower transition portion 116 to the upper transition portion 112) during treatment use.

Referring first to FIG. 3 and in particular FIGS. 3A and 3B, the above disclosed oral treatment assembly 100 and method of use treatment thereof is illustrated in to reference to the Posselt's movement diagrams as described in the Background section above. FIGS. 3A and 3B however further illustrate the caregiver determined treatment points and movement regions that include an exemplary identification of the condyle positioning area $CPA_1$, $DTP_1$ and the $DTA_1$ in the sagittal and horizontal planes of Posselt's border movements, respectively. FIGS. 3A and 3B reflect one exemplary embodiment of a caregiver's design treatment borders and area of controlled and free movement within the Posselt's movement area for the oral treatment assembly 100 consistent with this disclosure and the various embodiments of the oral treatment assemblies and features thereof of the oral treatment assembly 100 and the methods of treatment as described in this disclosure.

As illustrated in FIGS. 3A and 3B, an initial area within the Posselt's border movement diagram can be the Condyle Positioning Area $CPA_1$. The inventor hereof has defined and identified the CPA for design and treatment use of presently disclosed oral treatment assembly 100 typically composed of an upper assembly 110 and a lower assembly 114 (as will be shown in FIG. 5A) for treating patients that have various jaw related treatment conditions. In some embodiments, each oral treatment assembly 100 is customized to not only one or more of the patient's upper teeth 18 and lower teeth 16, but each is also designed based on the evaluation by the caregiver of the patient and the development of a treatment plan by the caregiver for that patient. In some embodiments, for each patient, the caregiver first determines a CPA which can be, but is not always, a point that approaches the physiologic rest position PRP for that patient. The CPA is best understood with reference to the Posselt's border movement diagram as described above. The CPA is an area within the Posselt's movement border where, for that patient, the caregiver has determined that the condyles should be positioned for treatment by placing and maintaining during treatment the condyles to within a determined desired movement area. The $CPA_1$ is shown in the sagittal plane in FIG. 3A to typically be an area that is downward and to the protruded position from the CR. The $CPA_1$ for this particular patient extends downward a distance of $D_3$ to a point about midway between the CR and the Hinge Axis Terminating Point position R. This $CPA_1$ also is defined in the protruded position directly forward from CR to a position that is as distance of $D_2$, which is about two-thirds of the maximum protrusion MP, distance $D_1$. As shown in this illustrated example, the top border line of the $CPA_1$ is shown slightly below the Posselt's border containing CR, MI and MP, which is only intended to reflect by way of example a thickness as to the oral treatment assembly 100, the amount of which may be negligible in some implementations or can be greater in other implementations depending on the implementing structure and materials.

The caregiver determines after analysis and evaluation of the patient and the particular one or more condition(s) or disorder(s) that can be treated through the use of the oral treatment assembly 100, the determined treatment point DTP within the CPA for treatment thereof. It should be understood that DTP can be multiple DTPs and in the alternative only be a DTA. The DTP and DTA for each patient will vary depending upon the patient as well as the condition or disorders to be treated and the determinations by the caregiver at various times or stages during the treatment using the oral treatment assembly 100. While shown by way of example in FIGS. 3A and 3B, the DTP can be a single treatment point within the three dimensions to which the caregiver defines and then specifies the features, positions and design and selection of the transition portions 112, 116 and other features of the oral treatment assembly 100. In some embodiments the DTA can be a defined limited treatment area that is not based on a single DTP but multiple DTPs or none at all. For example, the DTA could be determined by the caregiver to be solely based on the determined CPA for some types of treatments.

These are described in more detailed below but generally all embodiments of the treatment assembly as described herein includes two mated pairs of transition portions 112, 116 as will be addressed with reference to FIGS. 5-9, with a transition portion 109 having a an upper transition portion 112 and a mated lower transition portion 116. In some embodiments, these mated transition portions 112, 116 provide the negative angle RPA, and can collectively, when engaged, form some or all of new occlusal surfaces, and/or form, among other treatment features as described herein for providing predefined treatment movement borders and controlled vertical and horizontal vectors of movement therefrom. As shown in FIG. 5, the upper transition portion 112 is formed by one or more features of the assembly's upper assembly 110 and the lower transition portion 116 is formed by one or more features of the assembly's mandibular or lower assembly 114.

FIG. 3A also illustrates one exemplary selection of a DTP, identified as $DTP_1$, which was selected to be a distance $DDP_1$ downward from the CR and in a downward position from the MI for this patient. As the $DTP_1$ in this example is within the borders of the CPA, the oral treatment assembly 100 will be designed to prevent the mandible 14 from moving upward, decrease in vertical dimension, immediately from position $DTP_1$ that is protruded at a distance D0 from CR, wherein an assembly 100 prevents retrusion from position $DTP_1$ backward from protruded distance $D_0$ based on the RPA which defines the left border of the $DTA_1$. However, the patient can move the mandible 14 downward and protrusively as shown by allowed movement vectors $V_T$ that are within the $DTA_1$. As such, the DTA in this example is the area $DTA_1$ which is shown to be a subset within the CPA that is downward and to the right (protrusive) to the $DTP_1$. An allowed movement within the $DTA_1$ is shown as movement vector $V_T$ that can originate any position of the mandible 14 including from the determined treatment position at DTP, and that allows movement downward and protrusively therefrom.

As illustrated, the $DTA_1$ only provides for a new movement border in the closed position at the top and in the closed position on the left the latter of which is defined by the transition portion 109 and whose shape or slope is controlled by the selection of the RPA. As noted, a patient if free to move their mandible 14 from the treatment position defined by the RPA and other features including protruding their mandible 14 outward and downward along vectors $V_T$ that are within the DTA. Once the patient moves their mandible outside of the $DTA_1$, the patient's mandible moves along disengage vectors $V_D$, which are movement vectors wherein the patient can disengage the oral treatment assembly 100, such as disengaging the transition portion 109, which occurs with the lower transition portion 116 becomes disengaged or coupled from the upper transition portion 112. As one of skill in the art will understand, while the DTA and CPA are illustrated to in these figures to have linear lines, in most implementations, such DTA and CPA borders for the retrusion prevention or retrusion advancement or for occlusal separation will not be linear as they are determined and defined by the interacting surfaces and feature of the upper and lower assemblies 110, 114.

Figure 4A:
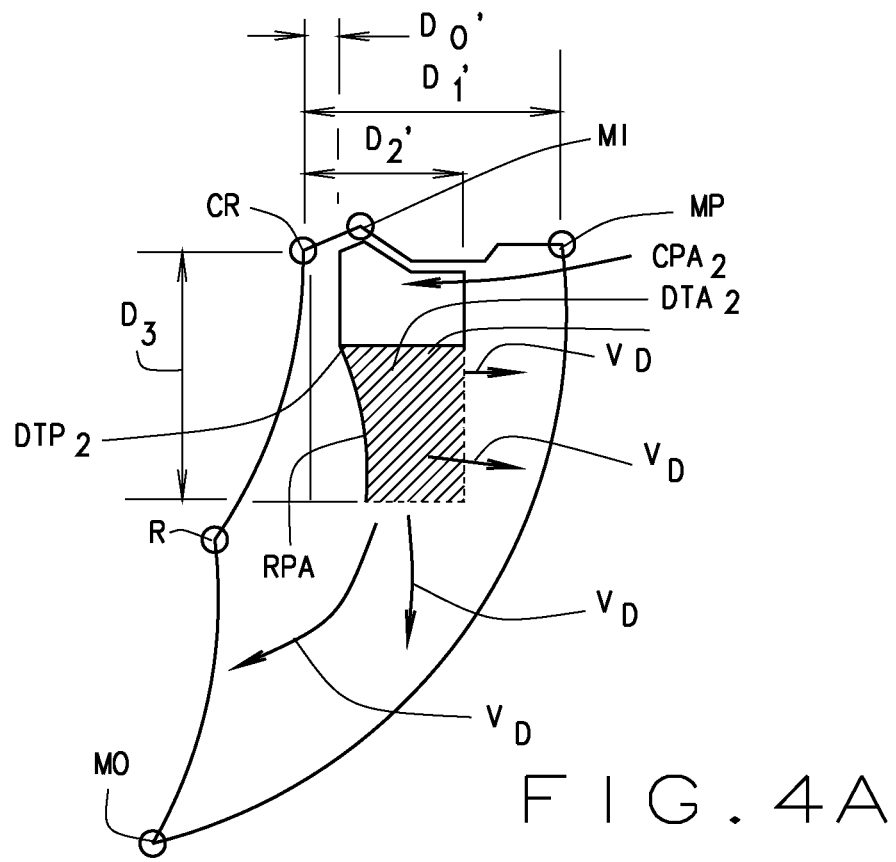
FIGS. 4A and 4B, illustrates the sagittal plane and FIGS. 4C and 4D illustrated the horizontal plane of the Posselt's movement diagram as modified by other embodiments of the present disclosure to illustrate a swallow against resistance (SAR) point and a condyle positioning area CPA for use with various embodiments of the treatment methods and assemblies of the present disclosure.

FIG. 3B illustrates these caregiver determined treatment points and areas for the oral treatment assembly 100 and features thereof in the Posselt's horizontal movement plane. As shown in this example, the CPA has been identified by the caregiver for this patient to be a protrusive forward movement from the CR forward to a distance of $D_5$, which is about two thirds of the maximum protrusion MP distance $D_4$. The CPA has also been defined to allow both a left and right lateral movement from the HML with a fully lateral movement from left and right of a distance of $D_7$. This forms the CPA in which the caregiver can select a DTP wherein the caregivers has determined ensure the proper positioning of the patient's condyles. In this example, the caregiver has identified that the $DTP_1$ is the protruded forward distance of $D_6$ from the CR, which by way of example is on the HML, but is not limited thereto in other implementations. The $DTA_1$ is shown as the area down and to the left and right of $DTP_1$ that is a protruded portion of the $CPA_1$ wherein the patient can move their mandible 14 further downward and also laterally to the left and right at total movement distance of $D_7$ about the HML during the treatment, which can that the condyles are positioned in the CPA of which the DTA is a subset. An example of one allowed movement vectors within the $DTA_1$ is shown in FIG. 3B as $V_T$. It should be understood that the regions of the $CPA_1$, the $DTP_1$ and the region of the $DTA_1$ as shown in FIGS. 3A and 3B are only exemplary and the disclosure and its embodiments are not limited to such examples. Further as shown, if the mandible 14 is moved lower than distance $D_5$, the assembly 100 becomes disengaged. Once disengaged, the wearer user/patient can move the mandible 14 with relative freedom as shown by disengage vectors $V_D$ that provide disengaged freedom of motion of the mandible by the user. By way of one example, while the $DTP_2$ in FIG. 3B is shown to be off the midline HML, as in some embodiments the caregiver may select a $DTP_2$ for a particular patient that is to the left or to the right of the HML but still within the CPA such as may be desired to train or treat one or more of the patient's JAFs. As introduced above, a patient may have a non-traditional horizontal mandible movement ability which is shown by way of example by movement vector $V_{NT}$ that can be at various angles and positions outside of the traditional Posselt's horizontal movement borders. In some examples, a caregiver can utilize the oral treatment assembly 100 and the determination of the CPA, DTP and DTA to treat patient's having such non-traditional mandibular movements The illustrated assembly controlled sagittal movements of FIG. 4A is similar to those of FIG. 3A but illustrate the selection of the $CPA_2$, the $DTP_2$ and the region of the $DTA_2$ for another patient or for different treatments using a different implementation or design of the presently disclosed oral treatment assembly 100. As shown in FIG. 4A, in some embodiments, the inventor has identified the applicable condyle positioning area $CPA_2$ for the patient and identified a $DTP_2$ as being at a location within the determined CPA that is about vertically under the intercuspal position ICP about one-half the distance between the ICP and the perpendicular horizontal line including the maximal mandibular opening R (i.e., the Hinge Axis Terminating Point HAT). In the exemplary embodiment of FIG. 4A, the $CPA_2$ is identified as having a greater downward distance $D_3$ that is closer to position R than as compared to that of the implementation of FIG. 3A. The $DTP_2$ is defined by the caregiver to be less protruded as compared that of FIG. 3A in that protruded distance $D_0'$ is less than D0. FIG. 4A also illustrates that the $DTP_2$ is downward from that of $DTP_1$ therefore provides treatment control of the mandible 14 to move the mandible 14 forward as the mandible 14 moves downward along the $DTA_2$ treatment border which is defined by the RPA of the transition portion 109. The shown RPA is an example of the transition portion 109 feature controlled movement of the mandible 14. As with FIG. 3, the treatment vectors $V_T$ illustrate the allowed patient non-controlled free movement of the mandible 14 by the patient during treatment that is still controlled within the $DTA_2$, up and until, the mandible is moved outside of the $DTA_2$ wherein the disengage vectors $V_D$ illustrate the movement whereby the patient can freely disengage the assembly 100 and therefore the treatment provided thereby Further, as shown in FIG. 4A, once the $CPA_2$ is determined and established for a patient, the $DTP_2$ is defined that is used under the presently disclosed methods and the resulting design of the treatment assembly 100 for configuring the placement and positioning of the transition portion 109, which is determined by the caregiver for the determined placement positioning of the patient's condyles. The treatment assembly 100 is designed as described in various embodiments herein so that during use of the treatment assembly 100 that the patient's condyle is positioned within condyle position area $CPA_2$ as shown. As shown in the sagittal view of FIG. 3A, the disclosed vertical dimension of occlusion area is depicted as the determined $CPA_2$ for this patient. Similarly, as to the horizontal plane of movement, FIG. 3B illustrates the horizontal positioning and control of the mandible 14 within the determined CPA2 that is shown by vectors $V_T$. Also as similarly disclosed in FIG. 3A, once the patient moves their mandible 14 downward or forward or both, sufficient to move the mandible 14 into a position wherein the treatment assembly 100 is no longer engaging or coupling the transition portions 112, 116, at these movements of the mandible 14, the patient can disengage the treatment assembly 100 and can freely move the mandible 14 downward forward and also backward, when in the downward disengagement position throughout the disengaging area and in various movements of disengaged freedom movements. To reengage the treatment assembly 100, the user must move their mandible 14 upward and protrusively in amounts sufficient for the lower assembly block 122 to have its lower transition portion 116 be positioned to again engage with the upper transition portion 112 of the upper assembly block 120. The patient will likely have to selectively move their mandible 14 forward and then upward to reengage the transition portions 112, 116 and therefore selectively engage the treatment assembly to move back within the control positions of the $DTA_2$.

Figure 4B:
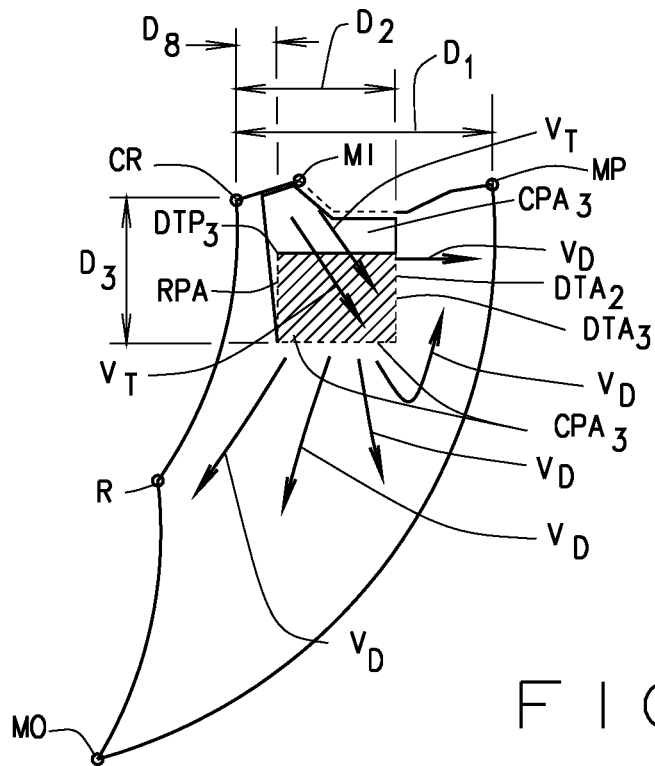

FIG. 4B illustrates a slightly different embodiment for a patient wherein the caregiver identifies that the $CPA_3$ for the particular patient should be located protrusively of the MI. In this case, retrusion of the mandible 14 beyond the left diagrammed border of $CPA_3$ is prevented by placement of the $DTP_3$ along the left border of the determined $CPA_3$ and the $DTA_3$. Further, patient allowed movement of their mandible 14 within the $DTA_3$ is limited to additional protrusion and downward movement from the $DTP_3$ such as along movement vector $V_T$ as illustrated.

The $DTA_2$ is shown in FIG. 4A to be within the $CPA_2$ that is forward protrusively and also downward reflecting the limited allowed movement of the mandible 14 relative to the maxilla 12 forward and downward enabling the patient limited movement of the mandible 14 about a SAR. Similarly, $DTA_2$ is shown in FIG. 4A to be within the $CPA_2$ that is forward protrusively and also downward reflecting a different limited allowed movement of the mandible 14 relative to the maxilla 12 forward and downward about the SAR. Of course, other movement areas for the DTA are possible. The limitations of the DTA are that once the DTP such as an SAR is established and the treatment assemblies are designed and manufactured, backward movement of the mandible 14 is prohibited by the interlocking of the transition portions 112, 116 and the downward movement is restricted by the RPAs that are configured to restrict the downward movement of the mandible 14 through the slope of the RPAs that forces the mandible 14 forward or protrusively when the mandible 14 is moved downward and which can be configured to prevent the unintended separation of the mandible 14 from the maxilla 12 through limiting the releasing or uncoupling unless there is an intended selective protrusive movement by the patient of the mandible 14 to release or decouple the lower transition portion 116 from the upper transition portion 112. This is shown in FIG. 4B as the disengaging vectors $V_D$ after disengagement as disengaged freedom motions. Once disengaged, the patient is no longer receiving treatment from wearing the assembly 100 and therefore has freedom of motion of the mandible 14 to the extent the such movement is restricted upward until the lower assembly 114 contacts the upper assembly 110 whereby further upward movement is restricted unless the mandible 14 is sufficiently forward or moved forward to engage the lower transition portion 116 with the upper transition portion 112 of the upper and lower oral treatment assemblies 110, 114, respectively.

FIG. 4B provides an illustration of the horizontal view of the Posselt's border movement diagram but that includes the $DTP_3$ such as by way of example the SAR point and condyle positioning area $CPA_3$ as described above, but in the horizontal plan of Posselt's border movements. FIG. 4B illustrates that the $CPA_3$ can also be identified and the DTP3 as well as the $DTA_3$ identified and specified in the manufacture of the treatment assemblies to provide anterior guidance including lateral guidance in the horizontal plane of Posselt's border movements. As shown in FIG. 4B, the caregiver can determine and design and provide to the patient a treatment assembly 100 that not only provides placement of the mandible 14 relative to the maxilla 12 in the sagittal plane but also that places the mandible 14 to prevent retrusion from $DTP_3$ and the retrusion border defined by the RPA and controlled selective protrusive movement during use by the patient.

This can include determining the DTP in a lateral position in the fully closed position to address lateral position and training of the mandible 14 relative to the maxilla 12, and therefore positioning of the left condyle and the right condyle in each of their desired positions, each of which may be different as determined by the caregiver for the particular patient. Further, the determined lateral DTP can include a lateral guidance feature that also allows for restricted lateral movement of the mandible 14 relative to the maxilla 12 about the determined lateral DTP.

Where applicable, the caregiver identifies for each patient the DTA for treatment movement that allows for the guidance in the lateral plane as shown in FIG. 4B of the mandible 14 relative to the maxilla 12, which can provide for treatment of condyles in the lateral plane as well. This lateral guidance or lateral movement aspect of the treatment assembly 100 can be provided in some embodiments by the same transition portions 112, 116 as described above for placement and movement control in FIG. 4A, through further sloping in the lateral plane of the transition portions 112, 116, or in some embodiments, additional structural features can be provided by the treatment assembly 100 to provide this additional placement of the mandible 14 relative to the maxilla 12 in a resting position $DTP_3$, and movement guidance of the mandible 14 relative to the maxilla 12 from such resting position $DTP_3$ during treatment use by the patient. Various exemplary embodiments will be described below in FIGS. 7, 8 and 9, by way of examples.

As noted above the common feature of the two mated pairs of transition portions 112, 116 is to engage, retain or otherwise selectively couple the mandible 14 relative to the maxilla 12 of each patient at the caregiver determined DTP, while still allowing the patient to have predetermined movement of the mandible 14 relative to the maxilla 12 during treatment use of the treatment assembly 100. Such predetermined protrusive and downward movements from the DTP is determined by the caregiver to be within a DTA that provides for ensuring the determined treatment that includes retrusion prevention as well as the other treatments as described herein. The DTA is determined to be from the DTP as determined by the caregiver but ensures that that no retrusion beyond the DTP can occur and that any movements protrusively, downward and laterally can be all controlled, restricted or limited as determined for suitable treatment by the caregiver. Following determination of the DTP and then the DTA, the caregiver specifies for the design and manufacture of the oral treatment assembly 100 composed of an upper assembly 110 and a lower assembly 114 and their transition portions 112, 116, respectively, as well as the other structure features as disclosed herein, for that patient based on the identified treatment of each patient.

By way of another example embodiment, the DTP will now be described wherein the DTP treatment point is determined by the caregiver based on a determined Swallow Against Resistance SAR area or point. It should be understood that this is only exemplary and is not intended to be limited to only this determined DTP.

In one such embodiment, the caregiver can utilize the known diagnosis position area known as Swallow Against Resistance SAR in locating a determined treatment point DTP. The utilization of the SAR has been identified by the inventor hereof for some embodiments of the oral treatment assembly 100 for use in placement of the mandible 14 during treatment of some patients. The SAR is understood by those in the art as being an area that is within Posselt's border movements. One such applicable SAR as identified by the inventor is a reference point determined for a particular patient that places the mandible 14 in a specific desired treatment position DTP or DTA, the position that the caregiver determines is the position that approaches the caregiver's determined physiologic rest position PRP for that particular patient.

With a vertical position or movement from this applicable DTP, i.e., the mandible 14 being opened more, it has been determined by the inventor that some patients using the treatment assembly 100 will be more likely to allow lip separation which can discourage nasal breathing. Nasal breathing is intended whenever possible during use as it increases utilizable oxygen and increases the quantity of relaxed muscles.

Figure 4C:
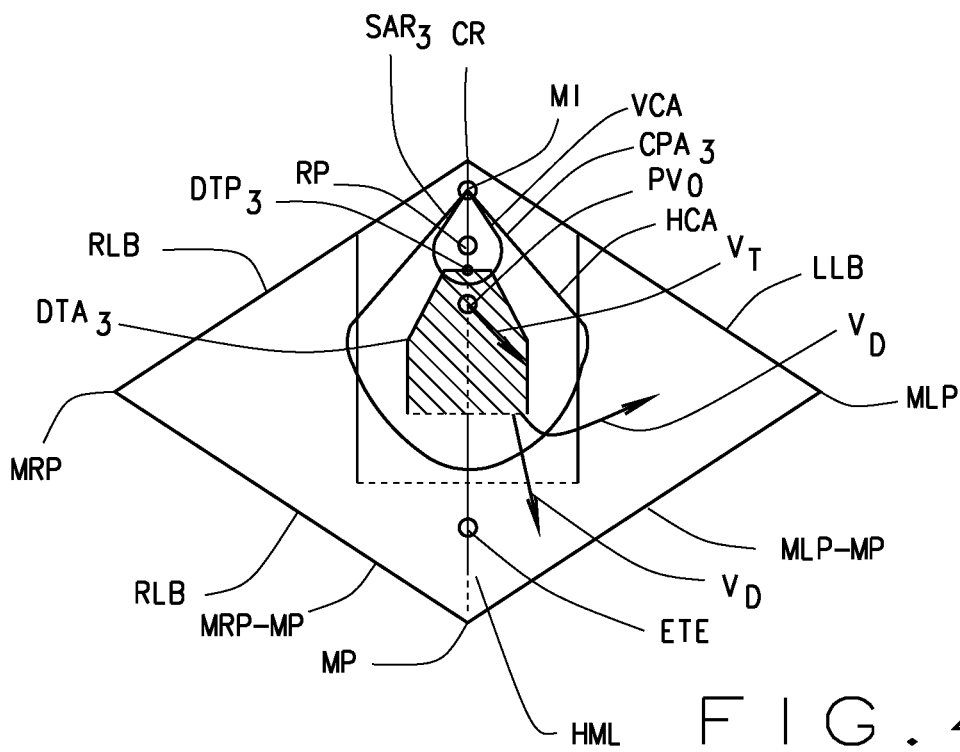
FIG. 4, including

FIG. 4C illustrates in the horizontal vector plane the retruded positions at the top starting at the CR along the left and right borders RLB and LLB to the maximum right lateral position MRP, and on the left maximum lateral position MLP. As the mandible 14 moves forward, the outer borders retreat to the point MP along border vectors MRP-MP and MLP-MP, respectively. In this horizontal movement vector plane, the caregiver can define a CPA having left and right lateral borders. As shown each is relative to the HML. The SAR area is identified as starting from the MI and downward and laterally and includes the PRP. In this example, the caregiver has defined the $CPA_3$ to include the $SAR_3$. Further areas are illustrated as being the vertical contact area VCA and the horizontal contact areas HCA that can be defined by the caregiver for design of the oral treatment assembly 100 as will be discussed further below.

As shown, the $DTP_3$ is identified to be within the $SAR_3$ and slight protruded from the PRP. In horizontal vector movement plane, this embodiment of the $DTA_3$ as selected by the caregiver extends forward and laterally from the $DTP_3$, but within borders of the $CPA_3$. The caregiver would then define the one or more features of the oral treatment assembly 100 to guide and control the movement of the mandible 14 along the borders of the $DTA_3$, but still allow the patient to move their mandible 14 from the $DTP_3$ to positions and along vectors that are within the borders of the $DTA_3$. One example of such is the position $PV_1$, wherein the patient has moved their mandible 14 forward along the HML slightly from the $DTP_3$ and from this position has then moved their mandible 14 along a vector $V_T$ (not shown) which is forward and to the left. As shown, the forward most border of the $DTA_3$ is defined as a dashed line indicating that any further forward movement of the mandible 14 beyond this forward position, such as any movement from the $DTA_3$ that is forward from the dashed border line towards the MP, results in the oral treatment assembly 100 not providing any further control or guidance whereby the patient has complete freedom of mandible 14 movement. This may occur where the patient moves their mandible 14 forward and then downward (not shown in the horizontal plane) along disengagement vectors $V_D$ and disengages the lower transition portion 116 from the upper transition portion 112 of the oral treatment assembly 100 of the lower assembly 114 and the and upper assembly 110, respectively.

Figure 4D:
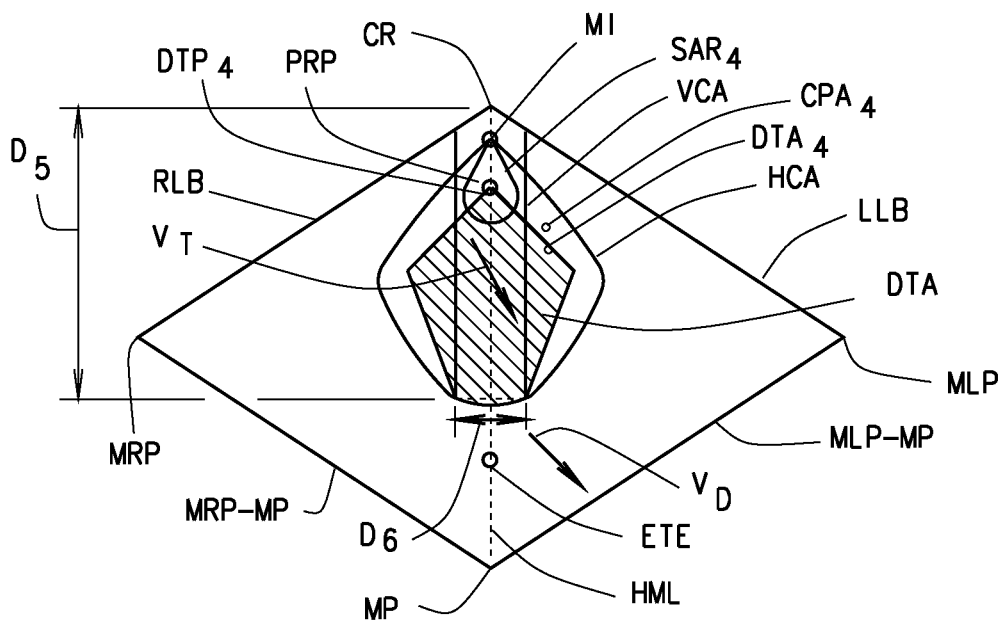

FIG. 4D illustrates another horizontal movement vector of another treatment and oral treatment assembly 100 designed based thereon. This example is similar to that of FIG. 4C, but in this example, the $DTP_4$ was selected by the caregiver to be at the PRP, which in this case is near the center of the SAR for this patient. The $CPA_4$ is defined as being spaced apart left and right of the HML, however, the $DTA_4$ starts at the $DTP_4$ and the borders of the controlled movement extend forward and laterally therefrom. This reflects the selection of the features of the oral treatment assembly 100 by the caregiver to allow the patient to move their mandible 14 along a controlled lateral vector $V_T$ as the patient moves their mandible 14 forward. The borders of the $DTA_4$ guide the mandible 14 forward and allow for some lateral movement, but such lateral movement $V_T$ is limited to a freedom of movement within the $DTA_4$ by the borders of the defined $DTA_4$, which is implemented in the features of the particular oral treatment assembly 100 for this patient. For example, in the features, angles and dimensions of the transition portions 112, 116 of the oral treatment assemblies 110, 114 and, in this illustration, the same on both the left and right sides. Of course, as one of ordinary skill in the art will understand, the caregiver can define the DTA and therefore the transition portion 109 features of the oral treatment assembly 100 so that the left side controls the left lateral movement different than the right side control of the right lateral movement, based on the needs of the treatment. This may be beneficial in training the muscles of mastication or of JAF factors as may be determined by the caregiver for the particular patient.

The assemblies 100 and method of use thereof as conceived by the inventor hereof includes various embodiments for the design and fabrication of patient specific and customized pairs of an upper assembly 110 and a lower assembly 114, referred herein in one exemplary embodiment as oral treatment assembly 100. In some embodiments, these may be oral trays, but this disclosure is not limited to trays or to full trays. Each pair of oral treatment assemblies 110, 114 include a new and improved set of treatment assembly 100 implemented transition portions 112, 116 that provide for specified functions as identified by the caregiver as being needed for the particular patient. Each of the pair of transitions portions 112, 116, and their features as described herein include at least a reverse cut angled RPA as measured from the Occlusal Plane OP and can also form, at least in part and in some embodiments, new occlusal surfaces 118, 119. Where the RPA includes such new occlusal surfaces 118, 119, the transition portions 112, 116 that slope in the direction from the top along the gum line of the upper teeth 18 downward and backward along a line to the gum line of the lower teeth 16. These reverse sloped transition portions provide retrusion prevention RP and in some embodiments, if so positioned, can provide for protrusion advancement as well.

Referring now to FIG. 5, FIGS. 5A, 5B, 5C and 5D provide illustrations of the oral treatment assemblies with transition portion 109 having the reverse angle RPA. The treatment assemblies 100 can be formed from oral trays forming the upper assembly 110 and lower assembly 114 respectively. These can be U-shape, or can be a left side and a right side that are coupled together with a bridging member such as behind the front teeth 16, 18 in some embodiments. Whether an oral tray with cavities or otherwise formed upper and lower assemblies 110, 114, the upper and lower assemblies 110, 114 can be formed by any suitable means. This can include molding of an acrylic or other material, vacuum forming, shrinking, traditional clasping including ball clasp, wire, delta and circumferential, 3D printing, and CAD/CAM milling, by ways of examples, and not limited thereto. Various materials for the forming the upper and lower assemblies 110, 114 and various features as described herein such as the transition portion 109 can be used as a caregiver may find suitable. These can include a single material for all components such as an acrylic, or may include a softer material such as a cushioning material for all or only a portion of each of the upper and lower assemblies and their features as described herein.

Figure 5A:
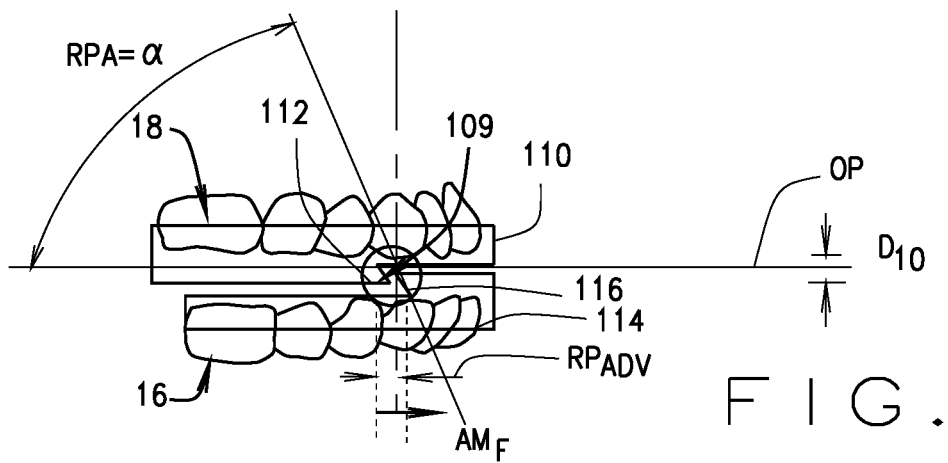
FIG. 5 includes FIGS. 5A and 5B illustrating side views of an assembly and includes FIGS. 5C, and 5D illustrating upper and lower oral blocks providing illustrations of some of the features and design of the retrusion prevention RP of some exemplary embodiments of the present disclosure.
Figure 5B:
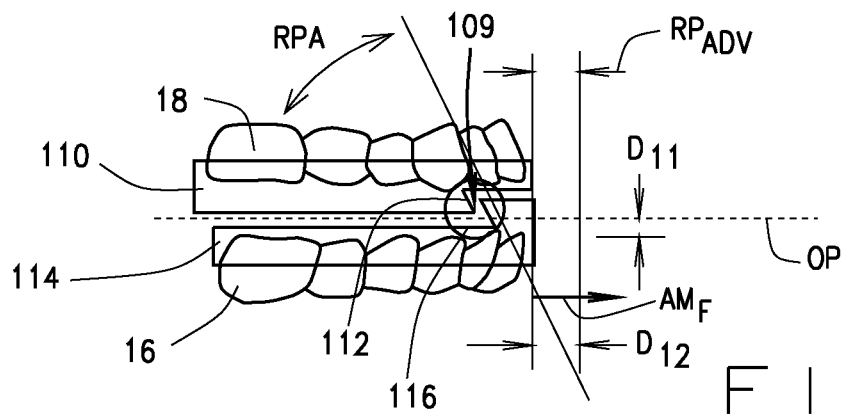
Figure 5C:
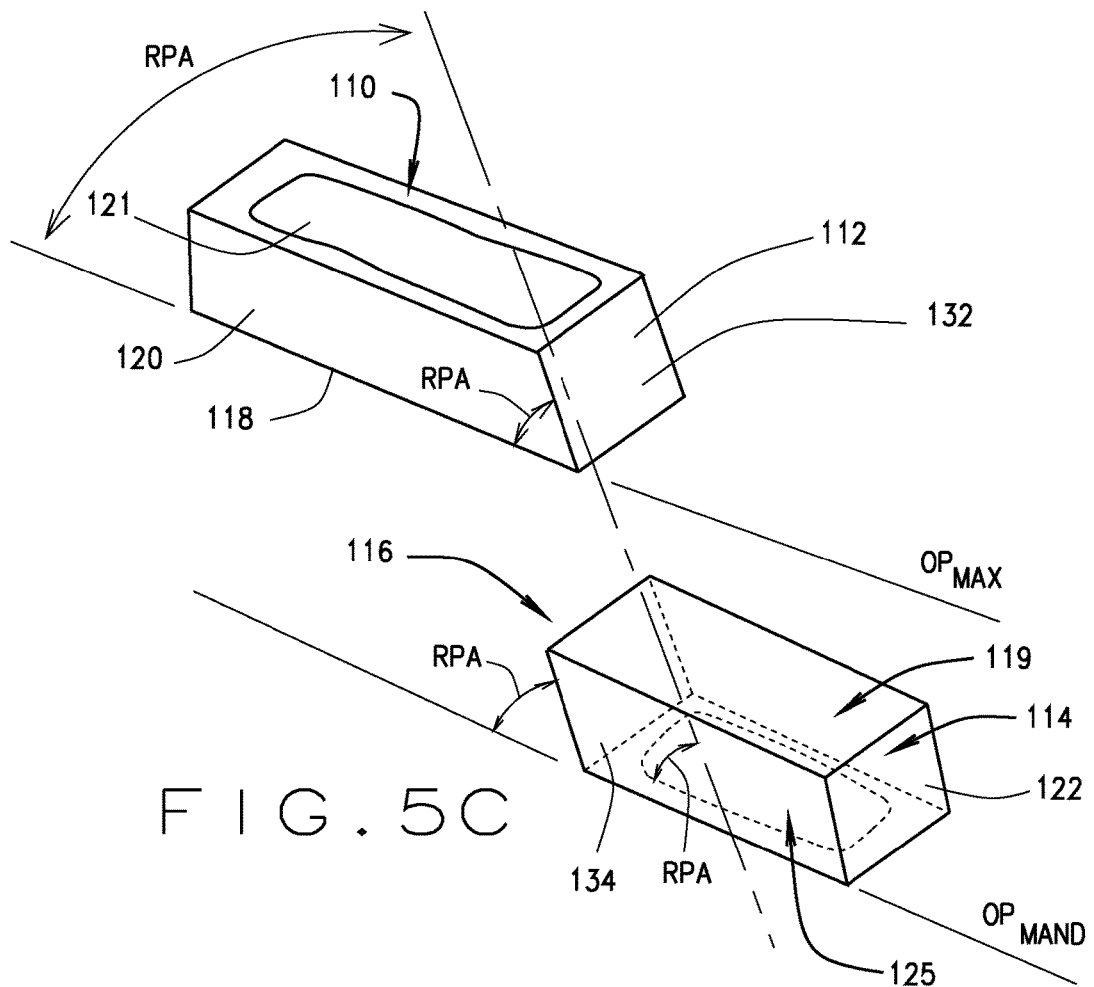

As shown in FIGS. 5A, 5B, and 5C, the upper treatment assembly 110 is configured to enclose all or only a portion of the upper teeth 18 in an upper cavity 121 and the lower treatment assembly 114 is positioned to enclose all or only a portion of the lower teeth 16 in a lower cavity 125. FIG. 5A illustrates lower assembly 114 selectively coupled with the upper assembly 110 through having the lower transition portion 116 engagable with the upper transition portion 112 such that when engaged the mandible 14 is coupled or retained with the maxilla 12 and the lower assembly 114 and the upper assembly 110 are fully closed about the occlusal plane OP at a centric occlusion point. As shown, due to the thickness of the materials and the other features as will be described herein, the lower assembly 114 and/or upper assembly 110 may be spaced slightly away from the natural OP, such as by a dimension of $D_{10}$. Each of the lower transition portion 116 and the upper transition portion 112 has its transition portion 112, 116 that has the same RPA so that each mates as shown. FIG. 5A illustrates the treatment assemblies 110, 114 being positioned for fully mating the mandible 14 relative to the maxilla 12 at the DTP, which in some embodiments can be the SAR. As shown, the oral treatment assembly 100 are formed wherein the mandible 14 is separated from the maxilla 12 relative the occlusal plan OP by a distance amount $D_{10}$, which can be as little as the amount of material of the combined thickness of the upper assembly 110 and lower assembly 114, or can be greater in some embodiments as may be desired by the caregiver for the particular treatment. The selection and varying of this thickness can be utilized by the caregiver in the design for treatments such as providing a lateral discluder LD, as will be discussed below.

As shown in FIG. 5A, the DTP is shown by way of example to the SAR point for this patient which is based on not only a retrusion prevention angle RPA, but also, a retrusion advancement $RP_{ADV}$. The $RP_{ADV}$ distance is the forward positioning $AM_F$ of the lower transition portion 116, in a forward position as defined by the selected the DTP and therefore transition portion 112, 116 at a position that provides for an advance or protrusion of the mandible 14 relative to the maxilla 12. While the amount of the $RP_{ADV}$ can be any amount, the inventor hereof has identified in some embodiments that a $RP_{ADV}$ of about 2 to 3 mm can be sufficient for the use of the treatment assembly 100 for not for retrusion prevention but also enhanced or required coupling or retaining the mandibular in relation to the maxilla 12. Further, such a $RP_{ADV}$ can be sufficient for use of the treatment assembly 100 for treating some patient disorders, such as sleep apnea. Of course, as also shown in FIGS. 5A and 5B, the caregiver determines the angle for the RPA to ensure retention of the lower transition portion 116 to the upper transition portion 112 allowing for movement of the mandible 14 only from the DTP within the DTA and based on the particular patient jaw movements.

Further, the caregiver determines the location of the transition portion 109 for the lower transition portion 116 and upper transition portion 112 along the arches and relative to the various enclosed upper teeth 18 and lower teeth 16 of each of lower assembly 114 and lower assembly 114, respectively. The retrusion angle RPA and its location or position, along with some of these other features, provides the caregiver with the ability to customize an treatment assembly 100 for each patient to ensure that the treatment assembly 100 provides for the retention of the patient's jaws is the objective retained position. By placing the mandibular assembly 114 in such mating position with the upper assembly 110, and keeping them retained or selectively coupled together in that desired position, this can ensure that such is maintainable by the patient during use without muscular contraction, due to the stretch memory in muscles, ligaments, and tendons of the jaw. The transition portion 109 comprised of the upper and lower transition portions 112, 116 of the upper and lower assemblies 110, 114, respectively, can be located anywhere and adjacent or in proximity to any of the teeth 16, 18. As one embodiment, the transition portion 109 can be located just distal of the maxillary cuspid or can be located interproximally, between the molar and the second or second and first pre-molar, i.e., in the gap between the molar and the first pre-molar or between the first and second pre-molars. In some embodiments, the transition portion 109 can be located in proximity to a cuspid, between the cuspid and the first bicuspids, between the first and second bicuspids, proximal to the distal of the maxillary cuspid, between the molar and the first pre-molar, or between the first and second pre-molars, by ways of examples, but not limited thereto. The location is selected by the caregiver based on the particular treatment and/or patient needs.

FIG. 5B illustrates the treatment assembly of FIG. 5A but wherein the mandible 14 is selectively moved forward and downward by the patient during treatment use. As shown, the lower assembly 114 has dropped downward by distance $D_{11}$ moving the mandible 14 downward away from the maxilla 12 is a slight opening of the jaw and mouth. The RPA and the interaction of the lower transition portion 116 with the upper transition portion 112 operate to move the mandible 14 and therefore the lower assembly 114 forward in a further protrusion identified as $D_{12}$ in FIG. 5B and also labeled as $RP_{ADV}$. As the lower transition portion 116 moves downward, the mandible 14 and the lower transition portion 116 are forced forward by the RPA, a movement $AM_F$ that is allowed based on the caregivers selection of the transition portion 109 location and the RPAs of the transition portions 112, 116. The transition portion 109 selection allows this selective movement by the patient during use, but biases the mandible 14 relative to the maxilla 12 to return to the DTP from within the DTA forward and downward movement.

While not shown in FIG. 5B, one of ordinary skill in the art will understand that an intentional downward and forward movement by the patient of their mandible 14 and therefore the lower transition portion 116 with respect to the upper transition portion 112 will result in the selective disengagement of the lower transition portion 116, and therefore the lower assembly 114 from the upper transition portion 112 and upper assembly 110. This can occur when the patient wants to remove the lower assembly 114 from the lower teeth 16 and the upper assembly 110 from the upper assembly 110 to selectively terminate use of the treatment assembly 100 and therefore the treatment. The mating configuration transition portions 112, 116 as selected by the caregiver provide the retrusion prevention RP includes the above described RPA that is identified relative to the occlusal plane OP in an anterior-posterior direction. The RPA is determined by the caregiver for each patient based on the amount of desired or required retrusion prevention or any required or desired $RP_{ADV}$ and provided a selective retention or coupling thereof. This RPA retrusion angle is also determined by the amount of patient protrusion of the mandible 14 required to overcome this RPA retrusion angle that provides the intercoupling of the lower assembly block 122, having this retrusion angle, from the upper assembly block 120, also having this same retrusion angle, in order to enable the patient to manipulate the mandible 14 to release or decouple their interconnection. Of course, the mating transition portions 112, 116 and RPAs must also be configured in view of the downward movement of the mandible 14 relative to the maxilla 12, as such selective retention or coupling is intended to be selectively manipulated by the patient during use. While not shown in FIG. 5B, but illustrated in FIGS. 5C and 5D, the upper and lower assemblies 110, 114 can include blocks 120, 122 or spacers formed with one or both assemblies 110, 114 such as in a monolithic body or permanently coupled or attached thereto, but can also be configured to be selectively removed from the upper and lower assemblies 110, 114. The method of selective attachment of any removable blocks 120, 122 can be of any suitable selective attachment means including, but not limited to, a pin, a snap, a flanged key, a twist lock, a press fit, by way of examples, but limited thereto. Where a selectively removable block 120, 122 is provided, the caregiver can adjust various of the described features such as lengths, thicknesses, surfaces and angles of the transition portions 112, 116 and the new occlusal surfaces 118, 119 provided thereby during a course of treatment of a single patient without having to build or configure completely new upper and lower assemblies 110, 114. Furthermore, the caregiver can customize the transition portion 109 and the new occlusal surfaces 118, 119 after manufacture such as by making minor adjustments to such features and parameters to provide more immediate customized treatment to the patient.

In some embodiments, by way of example only and not limited thereto, the RPA transition portions 112, 116 can be located distal of the cuspids. FIGS. 5A and 5B illustrate and refer to the RPA providing the retrusion prevention as RP as a feature of each of the transition portions 112, 116.

Figure 5D:
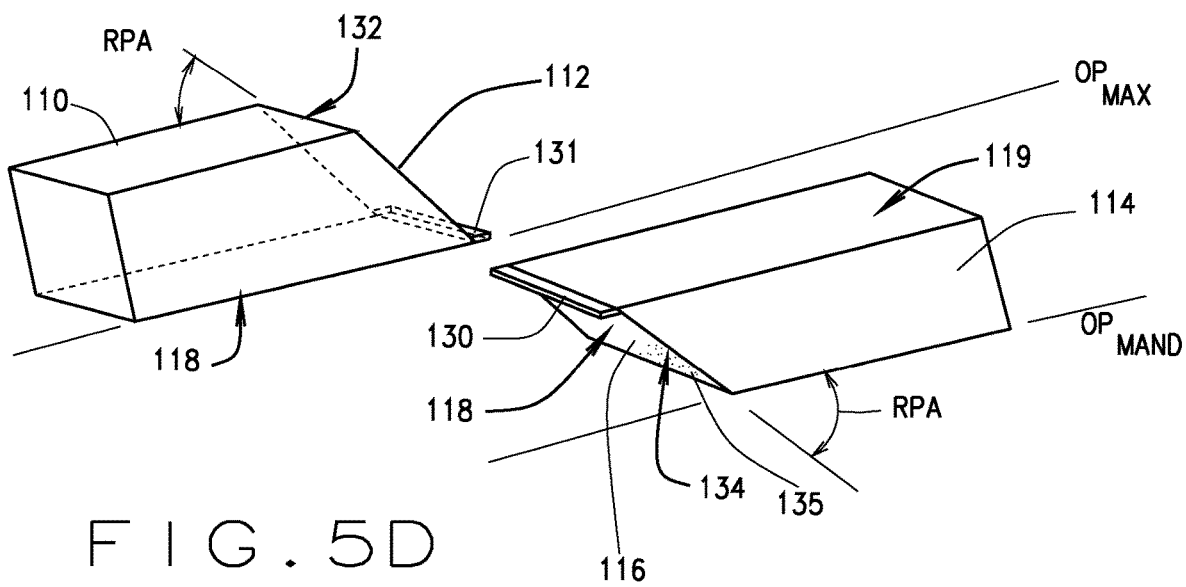

FIGS. 5C and 5D provide further details and description of the transition portions 112, 116 for the upper and lower oral treatment assemblies 100, formed in this example from upper and lower blocks 120, 122. FIGS. 5C and 5D illustrate portions of the upper assembly upper assembly 110 and the lower assembly 114, referred to as the assembly blocks 120, 122, the upper assembly block 120 and the lower assembly block 122 and features of various embodiments thereof. Also referred to as the vertical blocks the 120, 122 provides for the manufacturing or creation of the upper and lower transition portion surfaces 132, 134, which provides the transition portions 112, 116, respectively that is fabricated into the treatment assemblies such as a tray or the like to provide for various features as described herein. The upper block 120 can be in a maximum posterior location and can be as long or short as the caregiver may determine based on the treatment needs of each patient.

As shown, the upper block 120 can include a cavity 121 for receiving or enclosing at least in part some or all of the upper teeth 18 and the lower block 122 can include a cavity 125 for receiving enclosing at least in part some or all of the lower teeth 16. The upper transition portion 112 forms an upper transition portion surface 132 and the lower transition portion 116 forms a lower transition portion surface 134, each formed at the RPA and shown as angle line RPA in FIGS. 5C and 5D. Also, each of the transition portion surfaces 132, 134 can have a surface texture that can be smooth or otherwise as will be described. These are the assembly blocks 120, 122 that are the raised portions that are raised above the normal occlusal plane OP of the patient's teeth and that can define, at least in part, new occlusal surfaces 118, 119.

Further as shown in FIGS. 5C and 5D, in some exemplary embodiments, the transition portions 112, 116 can also include one or more features in addition to defining the mating RPAs with their formed transition portion surfaces 132, 134. By way of examples, as shown in FIG. 5D, the distal ends of the transition portions 109 of one or both of the upper transition portion 112 and lower transition portion 116, a raised lip 130, 131 can be formed and in some cases a flange receiving cavity (not shown) 131 at or near the distal ends of the transition portions 112, 116 from the gums of the transition portions 112, 116 that can be formed to add an additional interlocking capture and retention feature for retaining or coupling the lower transition portion 116 to the upper transition portion 112 to prevent the unintentional uncoupling of the lower assembly 114 from the upper assembly 110. When so formed, to release the lower transition portion 116 from the upper transition portion 112, the patient would have to intentionally add an additional forward movement of the mandible 14 relative to the maxilla 12 to uncouple and disengage the lower assembly 114 from the upper assembly 110. Such formed transition portion lips or flanges 130, 131 at the distill ends of the upper transition portion 112 and lower transition portion 116 can be configured to prevent the unintentional uncoupling of the transition portion 109, such as may occur when the patient unintentionally lowers the mandible 14 such as during sleep. These transition portion lips or flanges 130, 131 can prevent such unintentional separation of the lower assembly 114 from the upper assembly 110 during treatment use. In these embodiments, the raised transition portion lips or a single raised lip and flange 130, 131 or cavity/mating depressions in the mated transition portion 109 will allow the patient to selectively protrude the mandible 14 slightly forward during use, such as may occur if the patient lowers his mandible 14 slightly along the mated transition portion 109, but having a last catch of the lips, flanges or mating depression 130, 131, to prevent uncoupling of the transition portion 109, without intentional further protrusion by the patient to intentionally release the transition portion 109 completely.

In other embodiments also as shown in FIGS. 5C and 5D, the transition portions 112, 116 can include enhanced friction areas or structures or features 135 on the transition portion surfaces 132, 134 that increase the engagement or coupling friction between the two mated transition portion surfaces 132, 134. By having one or both of the mating surfaces transition portion surfaces 132, 134 of the two mated transition portions 112, 116 to have increased friction features 135 the mated transition portion surfaces 132, 134 provide an additional degree of restricted or inhibited movement of the lower transition portion 116 relative to the upper transition portion 112, and therefore, the mandible 14 downward relative from the maxilla 12. In such embodiments, the transition portion 109 can be formed to have a surface contact feature 135 of one or both transition portion surfaces 132, 134 that have texture that increases the mating friction of the mated transition portion 109 during use of the treatment assembly 100 during treatment by the patient. In this manner, a transition portion surfaces 132, 134 with texture features 135 can aid to inhibit or restrict minor movements of the mandible 14 during use unless the patient intentionally protrudes the mandible 14 forward to separate or at least reduce the friction as provided by the transition portion surfaces 132, 134 to allow the movement of the lower transition portion 116 downward relative to the upper transition portion 112. As noted above, in some other embodiments, the treatment and therefore the design, of the oral treatment assembly 100 by the caregiver for a particular patient may only require retrusion discouragement. In such embodiments, the transition portion transition portion 109 can be configured with very little or no reverse angle cut, especially where, as described herein, the transition portion transition portion 112, 116 having transition portion surfaces 132, 134 that have an increased friction or are configured with one or more engaging lips 130, 131 or features that aid in the retention of the mandible 14 relative to the maxilla 12 in a position that is less than being in a forward titrated position.

As will be described with reference to FIG. 6, including FIGS. 6A, 6B, and 6C, the assembly blocks 120, 122 or other features of the oral treatment assemblies 110, 114 as shown in FIGS. 5A, 5B, 5C and 5D can include and be customized by the caregiver to provide further treatment as may be determined for a particular patient, that is in addition to the retrusion prevention RP provided by the transition portions 112, 116 and the RPA angles thereof. These will now be discussed in view of exemplary embodiments of FIG. 5 as well as discussion above with regard to FIGS. 3 and 4 including FIGS. 3A, 3B, 4A, 4B, 4C, and 4D, as to treatment design.

Other Features in addition to Retrusion Prevention

In additional to the above, as previous disclosed the present disclosed oral treatment assembly 100 and the oral treatment assemblies enables the caregiver to provide a treatment assembly 100 that also treats other patient conditions.

Lateral Movement Aspect

One such additional treatment consideration is the lateral movement aspect LMA. As discussed above, one or more exemplary embodiments of the oral treatment assemblies 100, such as upper assembly 110 and lower assembly 114 can further be configured to provide, in addition to the retrusion prevention, lateral movement aspect LMA movement control or guidance. In addition to the RPA, the transition portions 112, 116 can include an angle that provides for control of the LMA, which is referred herein as angle LMAA. This angle is different and separate both in positioning and function than the RPA as described above, but in come embodiments, can be co-formed therewith. The LMAA controls the lateral movement of the mandible 14 and therefore the lateral borders of Posselt's diagram as described above. It should also be recognized that the LMA relates note only to the traditional Posselt's border movements, but also the non-traditional movements as shown and described above with regard to FIGS. 2D, and 3B. As noted above, nontraditional Posselt's border movement can occur in a small set of patients and the current treatment assemblies 100 are suitable for customization for accommodation and treatment thereof as well as shown in FIG. 6B as NTPM.

Figure 6A:
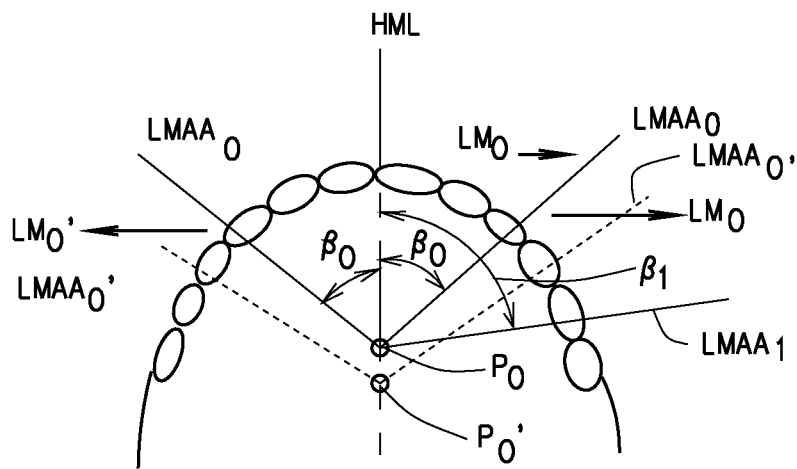
FIG. 6 includes FIGS. 6A, 6B, and 6C illustrating top view views of a maxilla or mandible arch illustrating lateral movement guidance feature and includes FIGS. 6D and 6E each illustrates a lateral movement guidance feature implemented on an upper and lower oral block, according to various exemplary embodiments of the present disclosure.
Figure 6B:
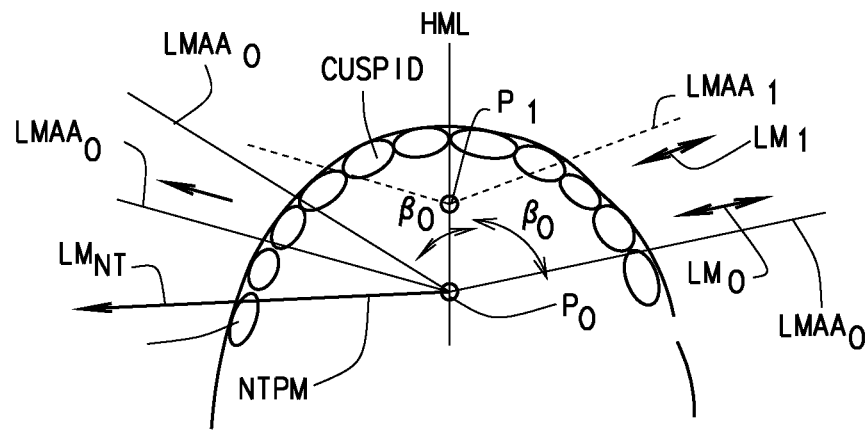
Figure 6C:
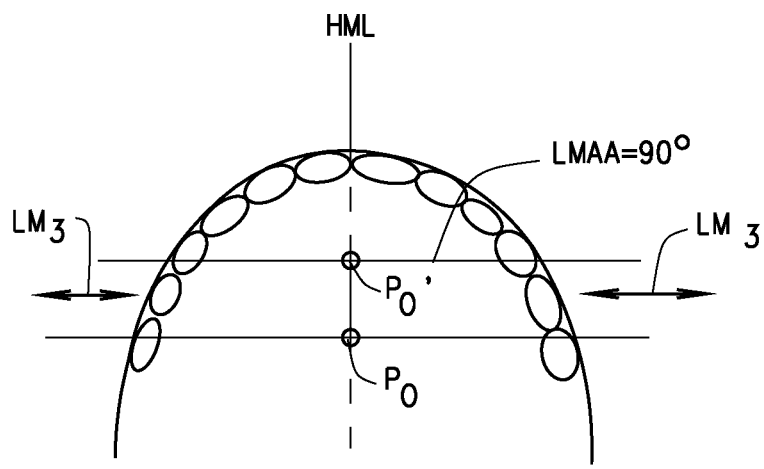

As compared to the RPA, the LMAA is defined, not relative to the occlusal plane, but rather relative to the centerline of the maxilla or referred herein as the HML as shown by way of example in FIGS. 6A, 6B, and 6C. The LMAA is defined as an angle from the HML, that provides some, but very little, lateral movement control or guidance if the LMA were about 90 degrees in the horizontal plane from the HML as shown in FIG. 6C. As known to those skilled in the art, the LMAA angles from the HML are often used to define the positioning of the anterior teeth 16, 18. In some embodiments, the LMAA can be selected, at least as an initial starting angle, to be the angle that is parallel to the lingual triangular ridge of the maxillary cuspid. However, LMAA's of less than 90 degrees to about 30 degrees from the HML can provide various amounts of LMA guidance or control. The LMAA and LMA aspect of the treatment assembly 100 can be integrated or co-formed with the RPA or surface of the transition portion 109 in some embodiments such as shown in the exemplary embodiments of FIG. 6D that illustrates the transition portions 112, 116 also defining LMAA as compared to the RPA. As illustrated in this exemplary embodiment, the LMAA is an angle that is angled from the lingual side to the buccal side of each of the transition portions 112, 116, which is referenced in FIG. 6D as being upper LMAA surface 136 and lower LMAA surface 138. The advantages of combining the LMAA for lateral movement guidance in the formation of the transition portions 112, 116 includes ease of fabrication by combining the directionality of the RPA and the LMAA into a single plane that defines the upper and lower contact surfaces 132, 134 of each pair of transition portions 112, 116. In other embodiments as will be described with regard to the exemplary embodiments of FIG. 6, the LMAA for providing LMA can be provided by a separate surface and formation than that which provides the RPA.

Referring now to exemplary embodiments of FIGS. 6A, 6B, and 6C, that are top views of the maxillary arch and upper teeth 18 that illustrate various options that a caregiver can determine for providing lateral movement guidance and therefore the design and configuration of a manufacturer lateral discluder feature LDF of the treatment assembly.

As shown in FIG. 6A relative to the HML centerline of the maxilla 12, the lateral movement aspect LM is defined as an angle LMA shown as $LMA_0$ having angle $\beta_0$ that extend from the HML at position $P_0$ in both the left and right directions. The LMAA is an additional angled slope that can be provided by the transition portion 109 that is in addition to the RPA and that slopes at the angle from position $P_0$ at angle $LMAA_0$. By providing the LMAA to both the upper transition portion 112 and the lower transition portion 116, lateral movement LM shown as $LM_0$ of the mandible 14 can be restricted or limited. The LMAA can be determined by a different point along the HML as shown by point $P_0'$, having the same LMAA.

The amount of lateral movement restriction and allowance can be determined based on the selection of the LMA from the HML. This is shown if FIG. 6B wherein the LMAA of $\beta_1$ is greater than the LMAA if $\beta_0$ of FIG. 6A allowing for a greater amount of lateral movement $LM_1$ as compared to $LM_0$. As shown, the placement of the transition portion 109 with the LMAA is shown to be between the cuspid or canine tooth and the first premolar along vector $LM_0$ wherein the $LMAA_0$ is angle $\beta_0$. The transition portion 109 can also be placed between the first and second premolars as shown by vector $LMA_1$ is $\beta_1$. Further, as illustrated in FIG. 6B, the non-traditional Posselt's border movements are shown as vector NTPM and shown as $LM_{NT}$. This can be accommodated by the oral treatment assembly 100 wherein the transition portion 109 is located in front of the first molar or slightly behind the 2nd premolar.

If the caregiver determines that for a particular patient there is no need for lateral guidance and therefore no LMAA is to be designed into the oral treatment assembly 100, than as shown in FIG. 6C, the LMAA having an angle $\beta_3$ that is equal to about 90 degrees, by way of example, is provided so that no lateral guidance or control is provided. As known to those of skill in the art, the LMAA and selection of location of such will vary by patient and could be an angle that is different than 90 degrees but still suitable for that particular patient for providing no lateral movement control and therefore free lateral movement, meaning no lateral restriction, movement control or guidance.

In some embodiments, the upper assembly block 120 and its upper transition portion 112 can be anywhere, but the location along the molars can provide for the most effective AGF if such is desired. The lower assembly block 122 and its lower transition portion 116 having the LMA with one or more LMAAs can be positioned to the rear or anterior to the upper transition portion 112 when not selectively retained or coupled by the user, but which can provide for selective mating and retention or coupling there between and therefore retrusion prevention when engaged by the patient. The location of the upper assembly block 120 above the molars can provide for improved effectiveness of other treatments such as anterior guidance by providing an anterior guidance feature AGF that can be implemented by the oral treatment assembly 100 such as on the lower assembly block 122. As will be shown and understood, AGF guidance includes control or guidance as to which teeth touch, when and by how much during a lateral movement and but also which teeth touch, when and by how much during protrusive or anterior movement. As will be described, various structures of the upper and lower assemblies 110, 114 can provide for customizable AGF for an assembly 100 for a particular patient.

Figure 6D:
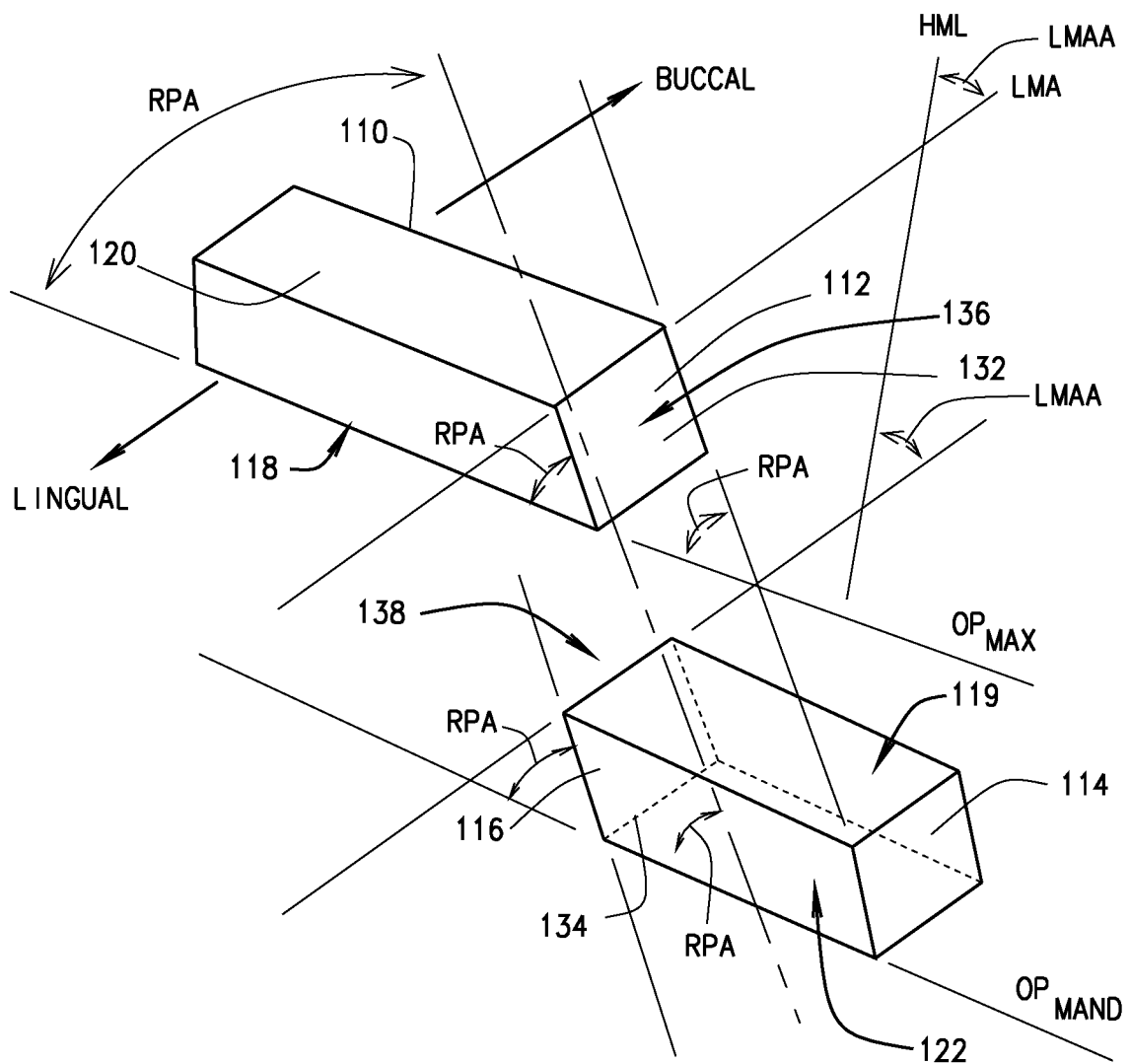

Referring now to FIG. 6D, as illustrated as to one set of mating upper assembly 110 and lower assembly 114, the upper block 120 defines the upper transition portion 112 having the RPA for retrusion prevention and having upper transition surface 132. The upper block 120 also defines an upper assembly occlusal surface 118 of the upper transition portion 112. The lower assembly 114 defines the lower transition portion 116 with lower transition surface 134 and having the same RPA, and defining the lower occlusal surface 119. However, in addition to the RPA as illustrated in FIGS. 5C and 5D, FIG. 6D further illustrates the upper and lower transition portions 112, 116 also implementing a LMAA (lateral movement angle) as illustrated in FIGS. 6A and 6B whereby the upper and lower transition portions are angled from the center line HML. As shown in FIG. 6D this is only the left side blocks of an assembly 100 as indicated by the sides being lingual or buccal, but it should be understood that this can be similarly implemented on the right side as well. The selected LMAA angles of the transition portions 112, 116 provide lateral movement guidance that is in addition to the retrusion prevention and coupling as provided by the RPA. The LMAA angles of these transition portions 112, 116 provide for the lateral movement guidance whereby the lateral movement of the mandible 14 is controlled from the resting fully closed treatment position during treatment and use of the treatment assembly 100. As can be understood from FIG. 6D, during the closing of the mandible 14, the LMAA guides and controls the lateral movement aspect of the mandible 14 relative to the maxilla 12. Further during movement of the mandible 14 when the upper transition portion 112 is coupled or engaged with the lower transition portion 114, lateral movement of the mandible is controlled by the transition portions 112, 116 and their LMAA angles so that only the lateral movements are along predetermined lateral movement vectors LMA as described above.

Figure 6E:
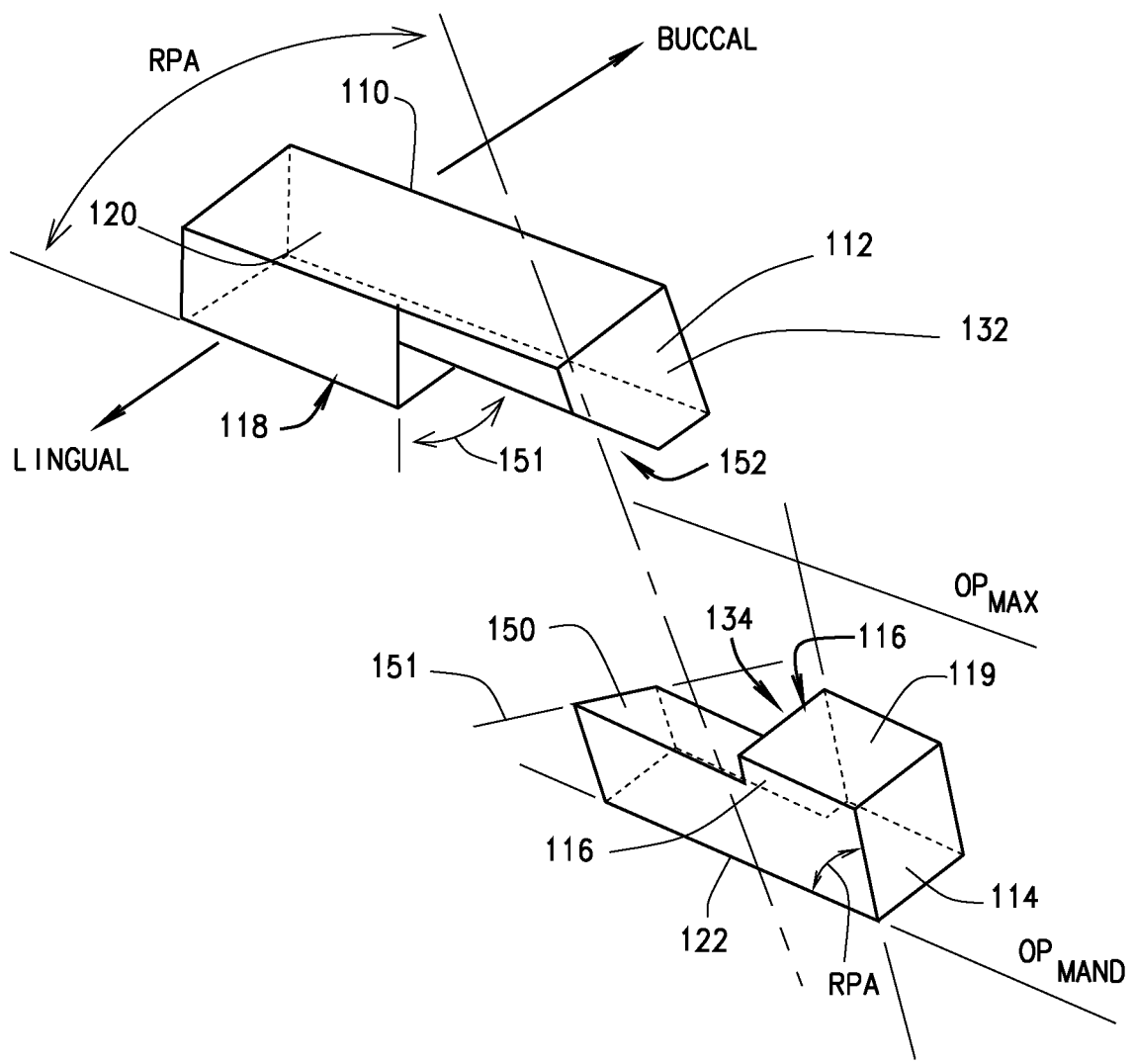

FIG. 6E illustrates a different treatment structure for assembly 100 for providing lateral guidance that could be for only one side wherein such lateral guidance is provided by a surface of the upper and lower blocks 120, 122 that is other than the transition portions 112, 116. As with FIG. 6D, FIG. 6E only illustrates the left side assembly 100 having a left upper assembly 110 with a left upper block 120 defining the upper transition portion 112 having angle RPA and with upper transition surface 132 and upper occlusal surface 118. The left lower assembly 114 including the left lower block 122 defines the lower transition portion 116 having the RPA with lower transition surface 134 as defined by an anterior portion lower block 122 that also defines the anterior occlusal surface 119. However, FIG. 6E illustrates an additional structural feature of the upper and lower assemblies 110, 114 and the additional treatment control that such provides. As a separate contact control surface between the upper and lower assemblies 110, 114, each further includes angled control occlusal surfaces 150 and 152 that have an additional mating or control angle 151. As shown, the lower assembly block 122 defines on a posterior end that is posterior to the lower transition portion 116 an angled posterior occlusal surface 119 that forms control surface 150 having an angle 151 that is downward from the lingual to buccal edges. The upper assembly block 120 has a similarly angled occlusal surface 152 that is a cut out of the lower portion of the anterior portion of the lower block 120 that starts at the upper transition portion 112 and extends backward. This upper angled occlusal surface 152 extends backward and need only extend backward sufficient to receive and couple to the posterior lower occlusal surface 150 of the lower block 122 sufficient to mate therewith and to control movement along this artificially defined movement border that includes angle 151, as well as the thicknesses and lateral position of such occlusal surfaces 150, 151. As can be seen to those of ordinary skill in the art, the mating of angled surface 150 of the mandible 14 with the surface 152 of the maxilla 12 during treatment provides for a different lateral positioning and control of the lower assembly 114 relative to the upper assembly 112 and therefore the mandible 14 relative to the maxilla 12 that is in addition to the control and guidance provided by the transition portions 112, 116 and their RPA and/or LMAA angles.

As should be understood to those of ordinary skill in the art, the illustrated structures of the blocks 120, 122 of the upper and lower assemblies 110, 114, respectively of FIGS. 5C, 5D, 6D and 6E are for illustrative purposes to show control and guidance surfaces and features for controlling the movement of the mandible 14 during treatment using the treatment assembly 100. It should be clear that these described control and guidance surfaces and features can be implements on various structures and structural elements of upper and lower assemblies 110, 114 and not limited to the simplicity of the blocks 120, 122 as shown in these explanatory illustrations. One or more of these structures, angled surfaces and features can be implemented, by way of different examples, by one or more structural features of the upper and lower assemblies 110, 114 such as upward or downward structural extensions, lingual or buccal structural extensions, contacting surfaces and combinations of extensions with receiving surfaces including cavities and cavity walls or other surfaces. By way of example, the lower transition portion 116 can be formed on one or more surfaces including the RPA and LMAA and other features, such as an end surface of an upward extending structure from the lower assembly 114. In such an example, the upper transition portion 112 can be formed by a contact surface on the upper assembly 112 such as a lingual surface of the assembly 112 that is on the lingual side proximate to an enclosed upper tooth 18. Three implementations of exemplary embodiments of such will be described with reference to FIGS. 7, 8 and 9.

Vertical Contact Surface (VSC) and Lingual/Palatal Extension

As discussed above with regard to FIG. 4C, the treatment assembly 100 can also be configured to include a vertical contact surface VCS that relates to the amount of mating surface between upper and lower members. If it is determined that the total mating surfaces of the upper and lower assemblies 110, 114, such as surfaces 118, 119, or transition portion surfaces 132, 134 is too small, an insufficiency will result and the mandible 14 can separate from the maxilla 12 during sleep thereby losing the desired treatment control of jaw position, and resultant treatment intended by the use of the treatment assembly 100, such as the opening of the airway. The determining for the setting of VCS is determined by the caregiver's analysis of each patient's physiologic swallow and lip seal. To address this, the caregiver can design the treatment assembly 100 to include a lingual extension LE for the upper transition portion 112 or possibly another feature of the upper assembly 110 where the caregiver determines that the particular patient needs increased VCS but is limited by total separation/vertical between the upper and lower assemblies 110, 114.

In such cases, the caregiver can design the treatment assembly 100 by extending the upper transition portion 112 inwardly or lingually toward the HML and accessing the vaulting contour of the maxilla 12. See lingual extension LE 171 as one example in FIG. 8B. This Lingual Extension LE 171 can also be referred to as a Palatal Extension PE as the extension from the upper transition portion 112 that lies to the lingual of the "Normal Occlusal Table". Further, in some embodiments, the LE can be formed as a structure that extends upward from the mandible 14 or the lower assembly 114 such as lower transition portion 116 that goes higher up into the palate and toward the palatal midline HML. This embodiment of the LE or PE extension rises upward from the occlusal plane OP of the mandible 14 as provided by the lower assembly 114 and also extends into the palate and toward the palatal midline HML. As such, the Palatal Extension PE or also referred herein as the LE will inherently decrease space for the tongue during use of the oral treatment assembly 100 by the patient. However, as it extends upward from the occlusal plane OP of the mandible 14, in such embodiments the LE will inherently increase the vertical contact surface VCS and in some cases, such increase can be substantial. As the VCS is increased, the area of the transition portions 11, 116 increases. Further, in those embodiments were lateral guidance is also a desired treatment the LMA feature can be included or adjusted and customized as well. In some embodiments, by way of example, the LE can also be formed on the backside of the cuspid wherein the oral treatment assembly 100 or at least the lower assembly block 122 of the lower assembly 114 through the addition of additional assembly material such as added assembly material to the lower block 122, that can provide for increased thickness or height.

Anterior Guidance Feature AGF

To further idealize the bite and function and anterior guidance feature AGF can be added to the lower assembly 114 as an additional feature as described below. While it is possible a portion of the AGF feature can be implemented on the upper assembly 110, in most embodiments, the primary AGF features are most often formed on the lower assembly 114 and in many cases formed as structural feature of the lower transition portion 116, as such provides the guidance and control for the movement of the mandible 14 relative to the maxilla 12.

In some embodiments, as introduced above, the AGF can be implemented on a oral treatment assembly 100 by providing an extension into the palate, or onto the lingual surface of the blocks 120, 122, or other structure of the assemblies 110, 114 that provide new surfaces relative to the anterior teeth 16, 18 in an apical or palatal direction relative to the natural tooth occlusal plane OP in an anterior-posterior direction. A caregiver can decide that for a particular patient the addition of the AGF to the oral treatment assembly 100 may be desired to provide reduced muscular contraction during movement of the mandible 14 during use by the patient. As will be discussed, the caregiver can define the AGF to include one or two treatment component features, lateral discluder LD and/or protrusive discluder PD.

The lateral discluder LD is a feature LDF that provides to the oral treatment assembly 100 a component that discludes or otherwise keeps the mandible 14 apart during a lateral guidance movement LMA as may be required for a particular patient. As such, a LD may be an addition of an additional structural feature such as a spacer or an addition amount of material that discludes or separates the mandible 14 at a defined distance from maxilla 12 during at least some or all portions of the movement of the mandible 14 relative to the maxilla 12 that may be greater than distance $D_{10}$ as addressed above with regard to FIGS. 5A and 5B. This can be formed by adding additional material to either the upper assembly 110 or lower assembly 114, or all or a portion of their assembly blocks 120, 122, such that the combined thickness of the upper assembly 110 and lower assembly 114 is greater than Occlusal Plane Separation OP $D_{10}$ of an otherwise provided treatment assemblies 100.

A protrusive discluder PD can be added for protrusive disclusion if the LD is inadequate for protrusive disclusion for a particular patient. In some embodiments, the PD can be placed on or about the cuspid or lateral incisor, but an alternate place would be on the central incisor.

The PD of the AGF can be an upward extension of the lower transition portion 116 that extends apical or toward the root or hard plate as compared to the natural occlusal plane OP of the maxilla 12.

In some embodiments, a desired location of the AGF is at a position that is opposing the cuspid lingual surface of the maxilla 12. Since the maxillary tissue is usually covered with the upper portion of the treatment assembly 110, the extension can go onto the cingulum or even the palatal tissue.

If additional AGF is required in the protrusive movement, the LA and/or the anterior guidance aspect of the AGF can be extended anteriorly to include contact that encompasses the lateral incisor of the desired right or left side.

Posterior Occlusion Aspect (POA)

The oral treatment assemblies 100 as described herein can further provide, in some embodiments, the ability for the caregiver to vary the anterior and posterior occlusions aspects during treatment use of the oral treatment assembly 100 by the patient. While discussed in further detail to the various exemplary embodiments, by way of one example, the posterior occlusion aspect POA of the oral treatment assembly 100 as described herein can be defined in at least four embodiments. A first embodiment is one where the oral treatment assembly 100 is configured such that the maxillary block 120 occludes against the mandibular anatomy. A second embodiment is where the oral treatment assembly 100 is designed so that the mandibular block 122 has a flat plane that occludes against the maxillary anatomy. A third embodiment is where the oral treatment assembly 100 is configured having the maxillary block 120 occluding against the mandibular block 122. A fourth embodiment would encompass "artificial anatomy" on one or both treatment assemblies 110, 114 to reinforce, change or idealize natural anatomic features, including but not limited to occlusal planes, overjet of buccal segments, and available tongue space, by way of example. The selection of the posterior occlusion aspect POA of the oral treatment assembly 100 is determined by the caregiver based on the identification of the desired treatment for treatment of a particular patient at a particular part of their treatment, which can change over a treatment period.

Embodiments and Combinations of Embodiments

As described above, depending on the determination of the caregiver for each patient, the treatment assembly 100 hereof can include a variety of different features that provide additional treatment features that enable the caregiver to customize the treatment assembly 100 to meet the treatment needs of each patient. The common feature in most all embodiments is the transition portion 109 that provides retrusion prevention RP. However, the treatment assembly 100 can, in some cases, but configured to have structural treatment features that do not provide such with a reverse RPA to provide such RP. Generally, the present treatment assembly 100 can provide different combinations of the features determined and specified by the caregiver for a particular patient's treatment. These can include Appliance Guidance Combinations AGC such as the following:

a. Retrusion Prevention RP with Lateral Movement Aspect LMA;
b. RP with Lingual Extension LE to increase vertical contact surface;
c. RP with LMA and LE;
d. RP with LMA and Lateral Disclusion LD;
e. RP with LMA, LE and LD;
f. RP with LMA, LD, and Protrusive Disclusion PD;
g. RP with LMA, LE, LD and PD;
h. RP with LMA, LE, LD, and PD; and
i. RP with LD+PD; RP with AGF-LD and/or AGF-PD.

Various other features and combinations of features are possible and considered to be within the scope of the present disclosure.

Three Exemplary Embodiments

Now that the general descriptions of the features and the treatment assemblies of the present disclosure have been described, three exemplary embodiments will be reviewed that implement one or more of the above features of the present disclosed treatment assembly. Exemplary embodiments of FIGS. 7 and 8 utilize upper assembly block 120 and lower assembly block 122 to provide the control and guidance features in large part through the provided and defined upper transition portion 112 and lower transition portion 116 on the ends or other portions of the assembly blocks 120, 122. The exemplary embodiment of FIG. 9 is a different design configuration as compared to the exemplary embodiments of FIGS. 7 and 8 in that the guidance, such as the RP and LMA, as well as some or all others, are provided by an extending pedestal that is selectively engaged by the patient during use into a mating treatment surface cavity, rather than upper and lower blocks formed on the respective oral treatment trays. As will be explained, in some embodiments, the use of the embodiment of FIG. 9 may be desirable in some situations wherein the blocks or guidance portions that would be formed thereon, may be otherwise undesired by the caregiver or the patient. It should be noted that the illustrations of FIGS. 7, 8 and 9 are rough illustrations provided herein based on actual oral treatment assemblies 100 reduced to practice by the inventor hereof in refining disclosed assemblies 100 in preparation for this disclosure. As each of these assemblies were constructed of clear plastic, and each includes numerous features, their illustrations and representations in FIGS. 7, 8 and 9 do not include all such features. The inventor herein, incorporate by reference, the numerous photographs of provisional application FIGS. 7, 8, and 9, and the specification descriptions of such, in the priority application disclosure of U.S. Provisional Application No. 62/778,143, from which the inventor has attempted to summarize and represent in the current FIGS. 7, 8 and 9.

Figure 7A:
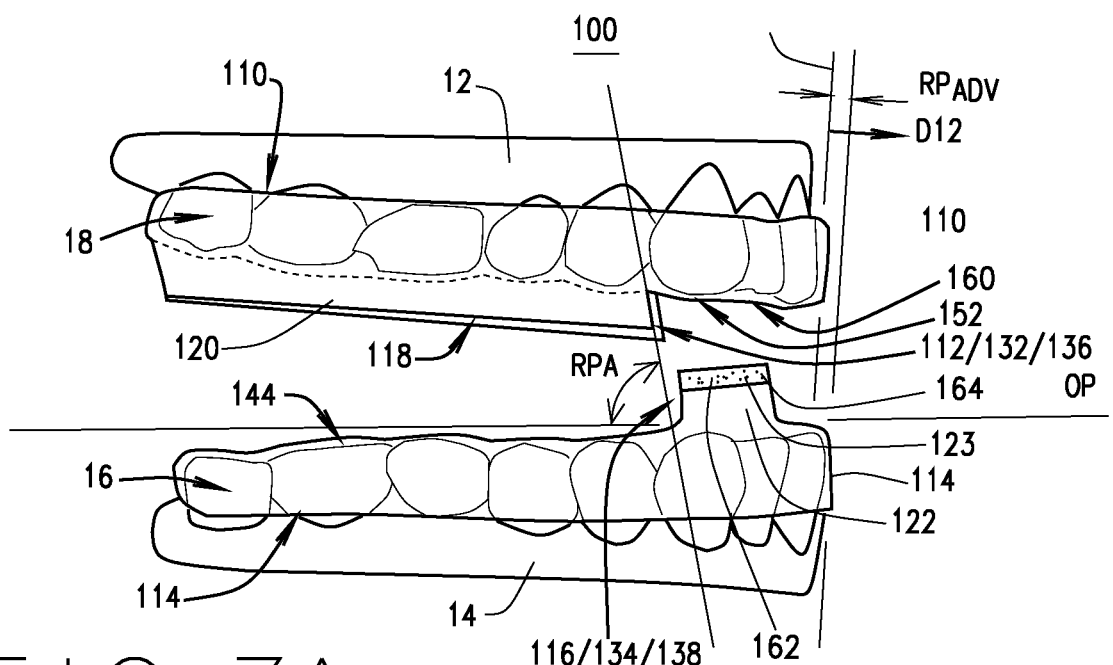
FIGS. 7A-7C, illustrates a first exemplary embodiment of an improved treatment assembly according to one embodiment of the present disclosure.
Figure 7B:
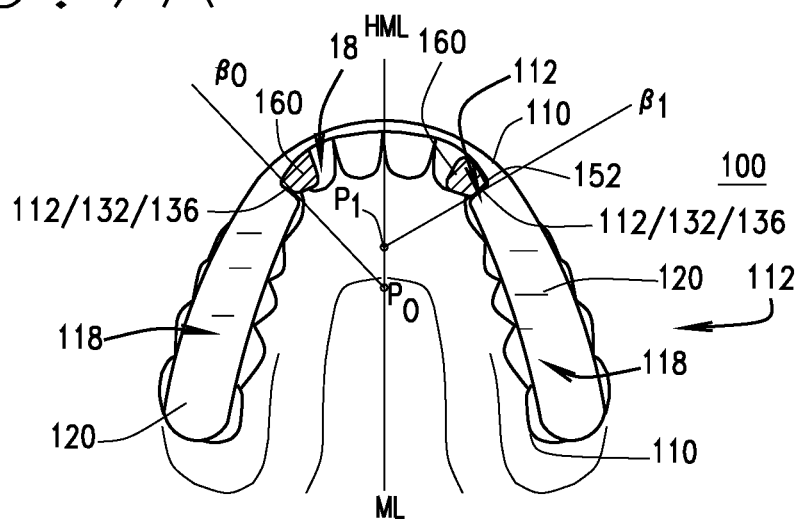
Figure 7B:
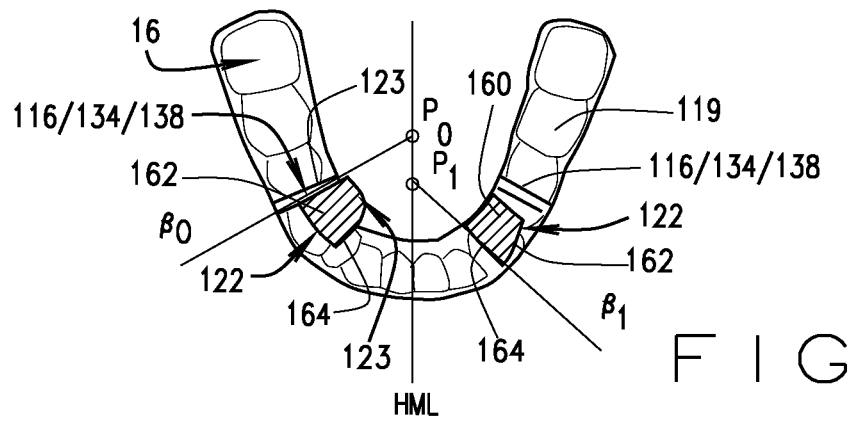
Figure 7C:
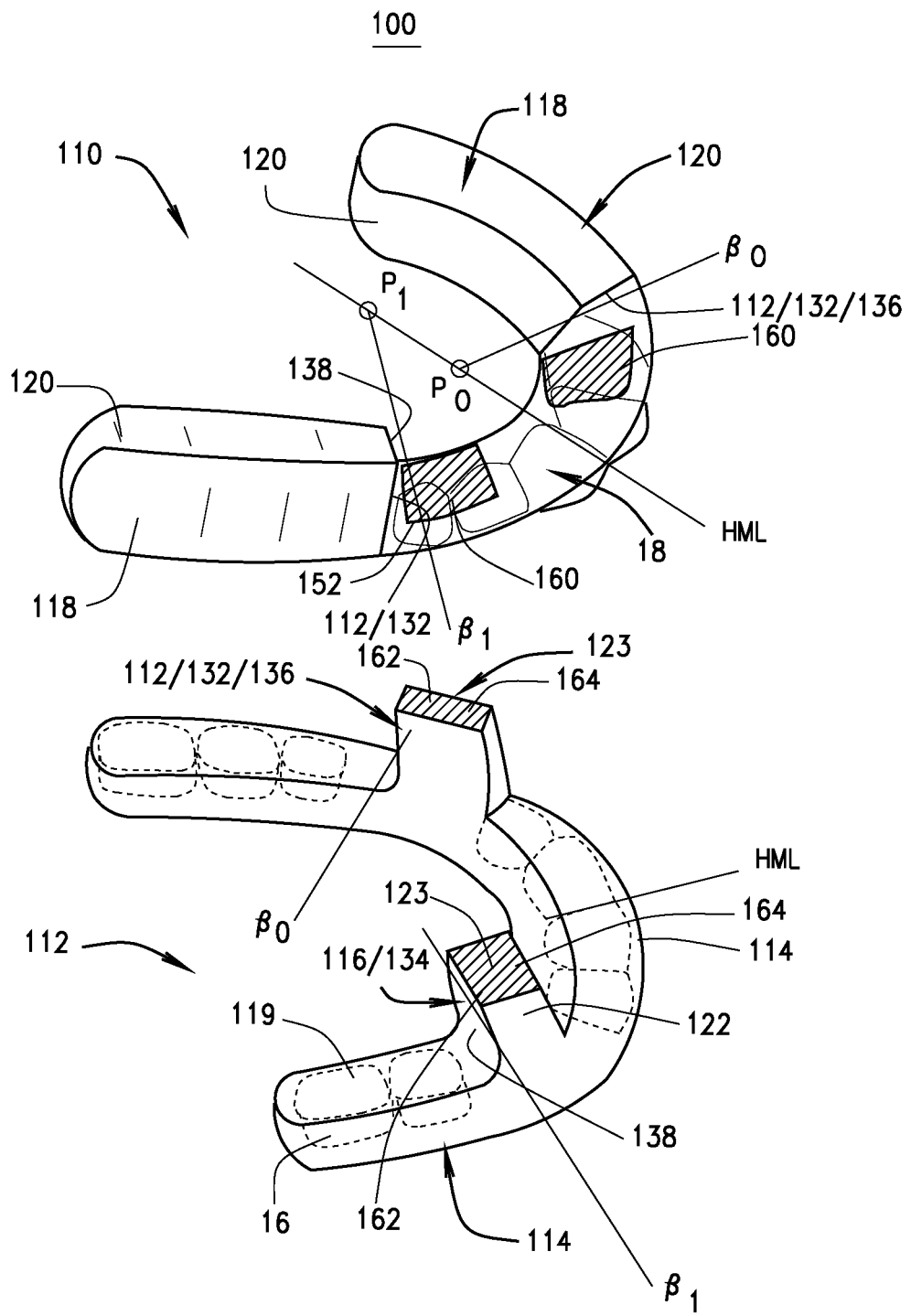

As shown in FIG. 7 including FIGS. 7A-7C, a first embodiment of a treatment assembly 100 is illustrated in numerous different views from numerous different points of view. This exemplary embodiment provides retrusion prevention and anterior guidance both laterally and anteriorly, while providing the patient with the maximum available room for their tongue and its movement during treatment use. As will be discussed, this is different than the second exemplary embodiment of FIG. 8 that provides the LE feature which extends upward and into the lingual area and therefore can interfere with a patient's tongue and its movement and therefore some patients may find it bothersome.

The exemplary embodiment of FIG. 7, as shown in FIGS. 7A, 7B, and 7C, an upper and lower assemblies 110, 114 with upper and lower blocks 120, 122. define the vertical contact surface VCS. The upper assembly 110 and the lower assembly 114 together form the oral treatment appliance 100. FIG. 7A is a side view of treatment assembly 100, with FIG. 7B showing a bottom view of the upper assembly 110 on the top and the top view of the lower assembly 114. FIG. 7C similarly shows a perspective view of the bottom view of the upper assembly 110 and the top view of the lower assembly 114. Each illustrates different view of an upper assembly 110 having an upper block 120 and the lower assembly 114 having a lower block 122 each of which defines the RPA by the mating of the upper transition portion 112 having upper transition portion surface 132 and the lower transition portion 116 having the lower transition portion surface 134.

As illustrated, this example of an assembly 100 includes the upper and lower assemblies 110, 114 having connected matable left sides forming the left side $TP_L$ and defining a $RPA_L$ and right sides forming the right side $TP_R$ and defining the $RPA_R$. As one of ordinary skill in the art would understand, the formed left side $TP_L$ and right side $TP_R$ could be the same angle or a different angle depending on the decision of treatment by the caregiver for the particular patient. Also this particular exemplary embodiment can include a front defined breathing orifice or space which is defined in the front between lower left side $TP_L$ and the right wide $TP_L$ where no upper or lower block 120, 122 is formed, as shown in the top view of the lower assembly 114 in FIG. 7B. As one of ordinary skill in the art will under stand in this embodiment with a front breathing space option, while RP is provided, no structure is provided that provides anterior guidance to the anterior teeth.

As shown, the upper and lower transition portions 112, 116 each include the upper and lower transition portion surfaces 132, 134 respectively. Further the centerline HML is shown that defines the LMAA, which in the exemplary embodiment is formed at $\beta_0$ on one side that forms upper and lower LMAAs 136, 138 on the right side and $\beta_1$ that forms the upper and lower LMAAs 136, 138 on the left side. This exemplary embodiment further includes VCS at the mating of the upper and lower blocks 120, 122 and the amount of material provided by each during contact, which determines and provides for the amount of the mating surfaces on the upper and lower assemblies 110, 114.

Further LE or PE, where required can be provided by shaping of the lower block 122 inwardly or lingually toward the HML and accessing the vaulting contour of the maxilla 12, which will be shown in more detail in the exemplary embodiment of FIG. 8. Further, lateral disclusion LD, as described above, can be provided by structure on the upper and lower blocks 120, 122. In this example, as shown, the lower block 122 includes a shaped upper end 123 and the interior or lingual side surface of the upper assembly 110, which could be a portion of the upper block 120 or otherwise, includes a shaped LD/PD contacting surface. The upper end 123 of lower block 122 can include a shaped portion that provides for lateral disclaimer LD 162 and/or protrusive disclaimer PD 164 as shown in FIGS. 7A and 7C. The LD 162 in this embodiment is a structural feature that provides for discluding or otherwise keeping the mandible 14 apart during a lateral guidance movement LMA as provided by the LMAA 136, 138. As such, the LD 162 is shown to be an addition of an additional structural feature that provides the caregiver's defined additional space through the addition of an addition amount of material to the lower block 122 and possibly to the upper inner contact surface 160 that discludes or separates the mandible 14 at a defined combined distance or thickness that is greater than the occlusal plane separation OP $D_{10}$ by an amount of $D_{12}$ that is the increased distance from maxilla 12 during at least some or all portions of the movement of the mandible 14 relative to the maxilla 12 as addressed above with regard to FIGS. 5A and 5B.

A structure that provides for protrusive discluder PD 164 can be added for protrusive disclusion if the LD 162 is inadequate for protrusive disclusion for a particular patient. In some embodiments, the PD 164 can be a structure that is placed on or about the cuspid or lateral incisor, but an alternate place would be on the central incisor. As shown in the embodiment of FIG. 7, the PD 164 is formed by way of example as a feature of the top end 123 of the lower block 120 and a portion of the inner contact surface 160 of the upper assembly 110. In other embodiments, the PD 164 of the AGF can be an upward extension of the lower transition portion 116 that extends apical or toward the root or hard plate as compared to the natural occlusal plane OP of the maxilla 12. Also, the amount of material in the upper blocks 120 on both right and left sides as shown, as well as any possible additional material on the posterior portions of the lower blocks 122 (not shown) can be configured to provide posterior occlusion aspect POA treatment. The structures of such can be provided by the caregiver to vary the anterior mandible 14 at a defined distance from maxilla 12 during at least some or all portions of the movement of the mandible 14 relative to the maxilla 12 that may be greater than distance $D_{10}$ as addressed above with regard to FIGS. 5A and 5B. This can be formed by adding additional material to either the upper assembly 110 or lower assembly 114, or all or a portion of their assembly blocks 120, 122, such that the combined thickness of the upper assembly 110 and lower assembly 114 is greater than Occlusal Plane Separation OP $D_{12}$ of an otherwise provided treatment assemblies 100. Further, the material in the posterior portions of the upper block 120 and possibly the lower block 122 can be reduced from that which is shown to reduce or possibly eliminate posterior occlusion if so designed by the by the caregiver.

In summary, each of these structures can provide for caregiver selected design for a particular treatment of a particular patient.

Figure 8A:
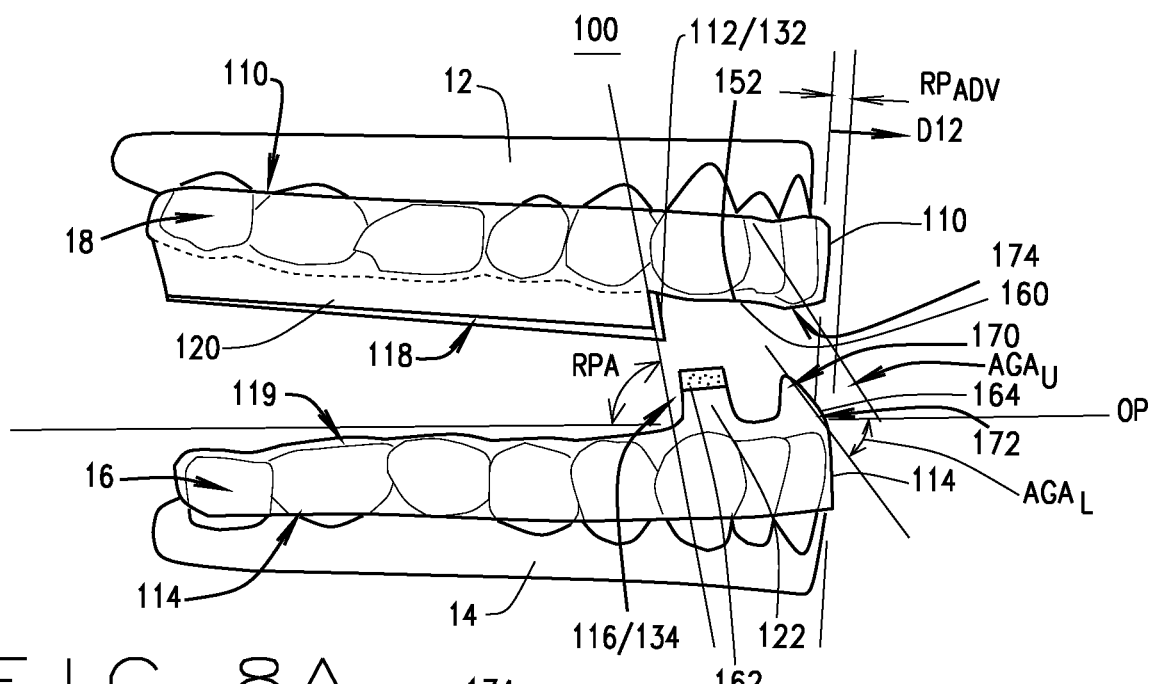
FIGS. 8A-8C, illustrates a second exemplary embodiment of an improved treatment assembly according to another embodiment of the present disclosure.
Figure 8B:
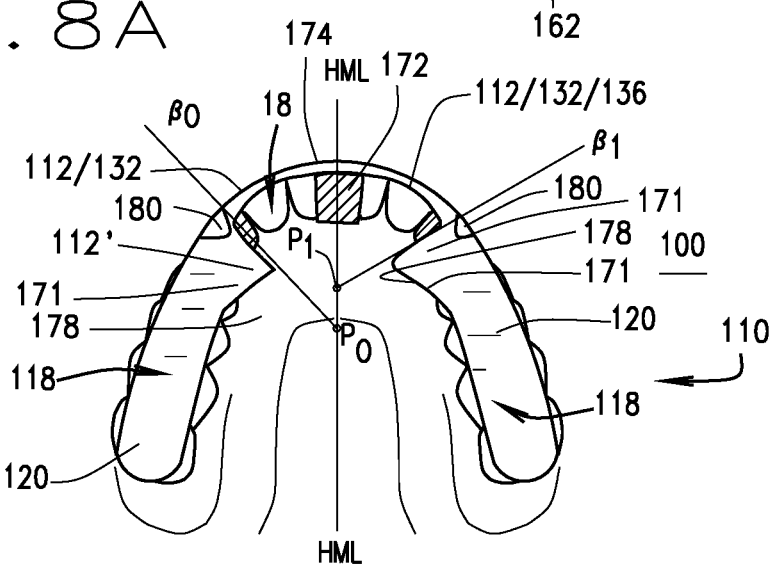
Figure 8B:
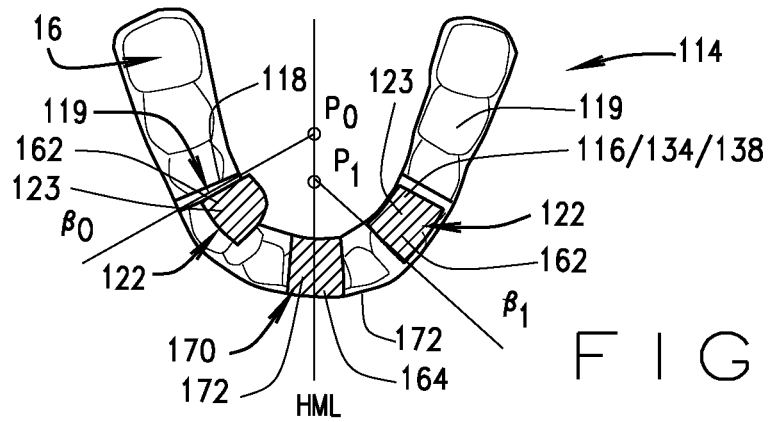
Figure 8C:
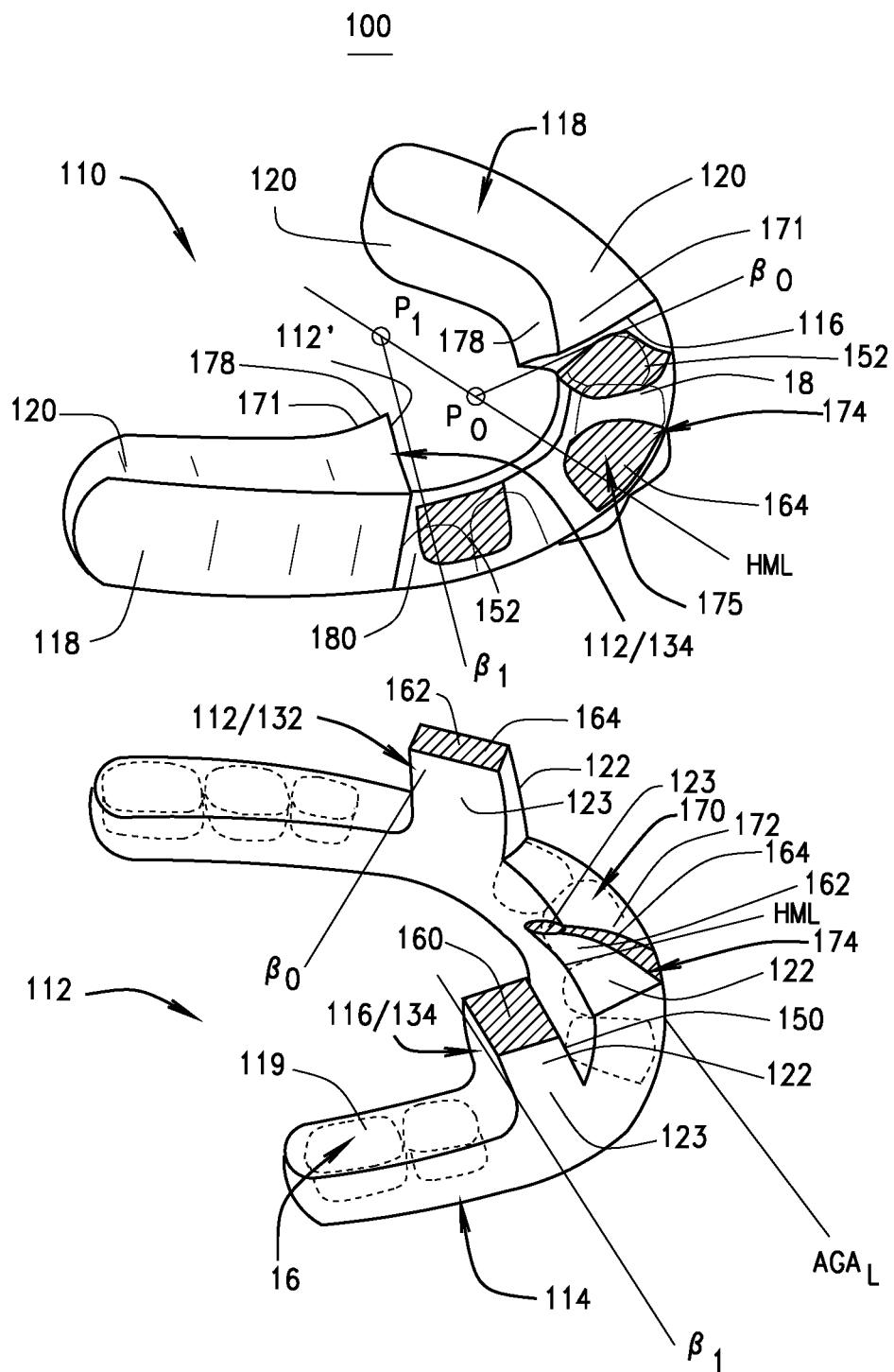
Figure 9A:
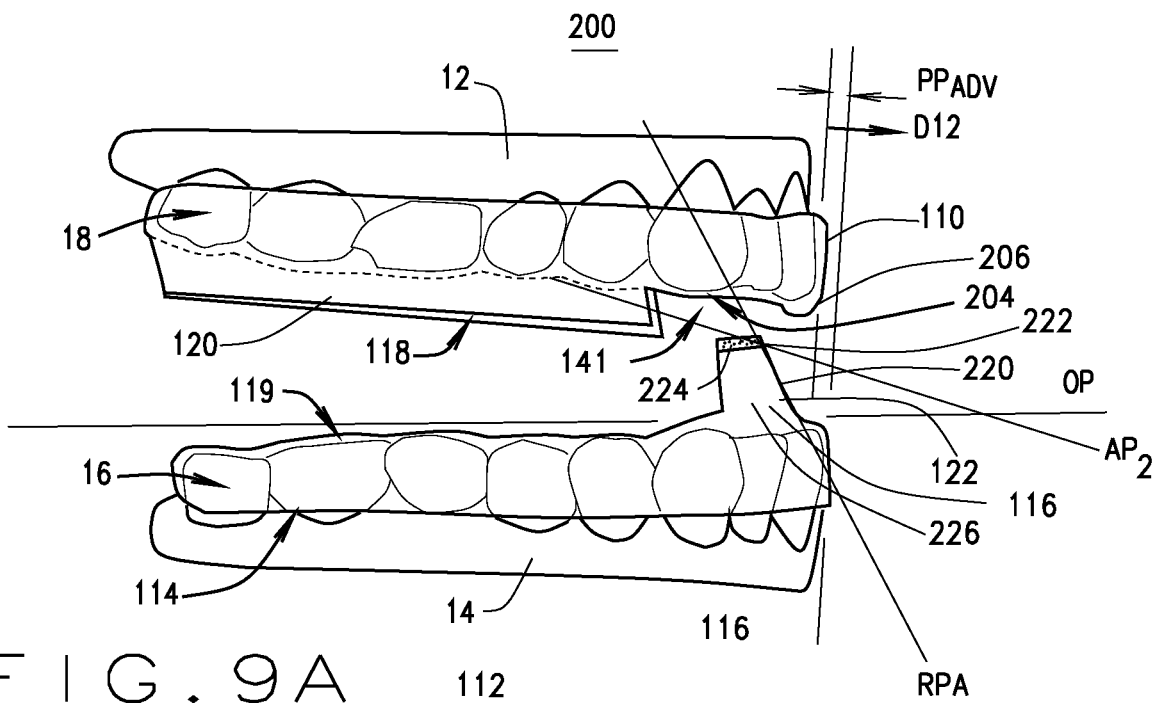
FIGS. 9A-9D, illustrates a third exemplary embodiment of an improved treatment assembly according to yet another embodiment of the present disclosure.
Figure 9B:
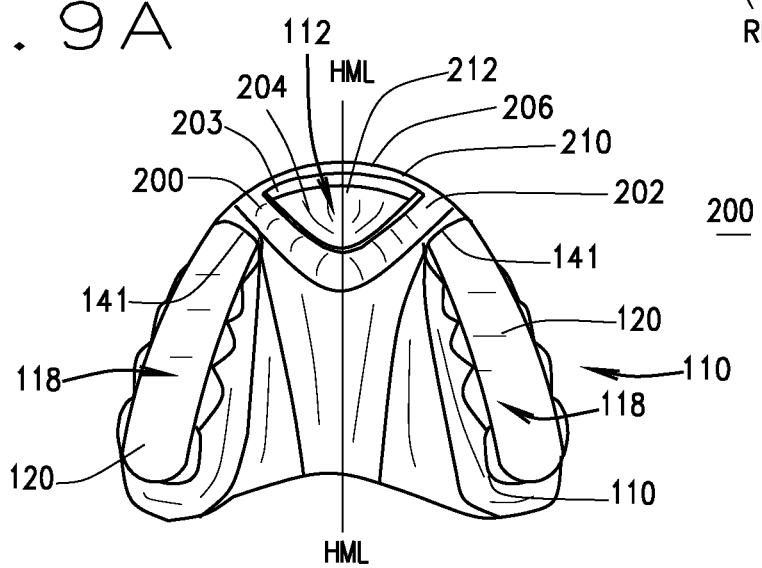
Figure 9B:
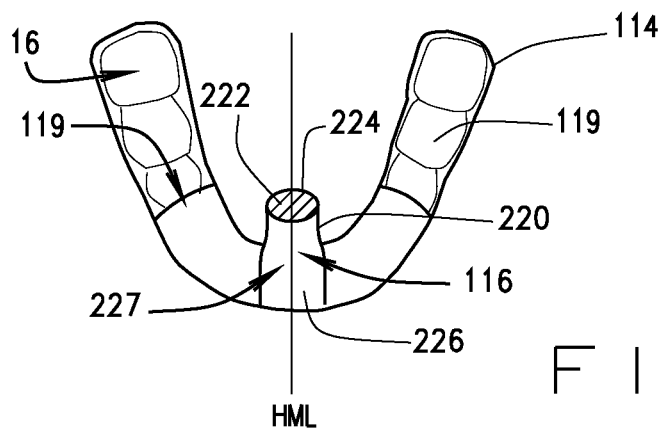
Figure 9C:
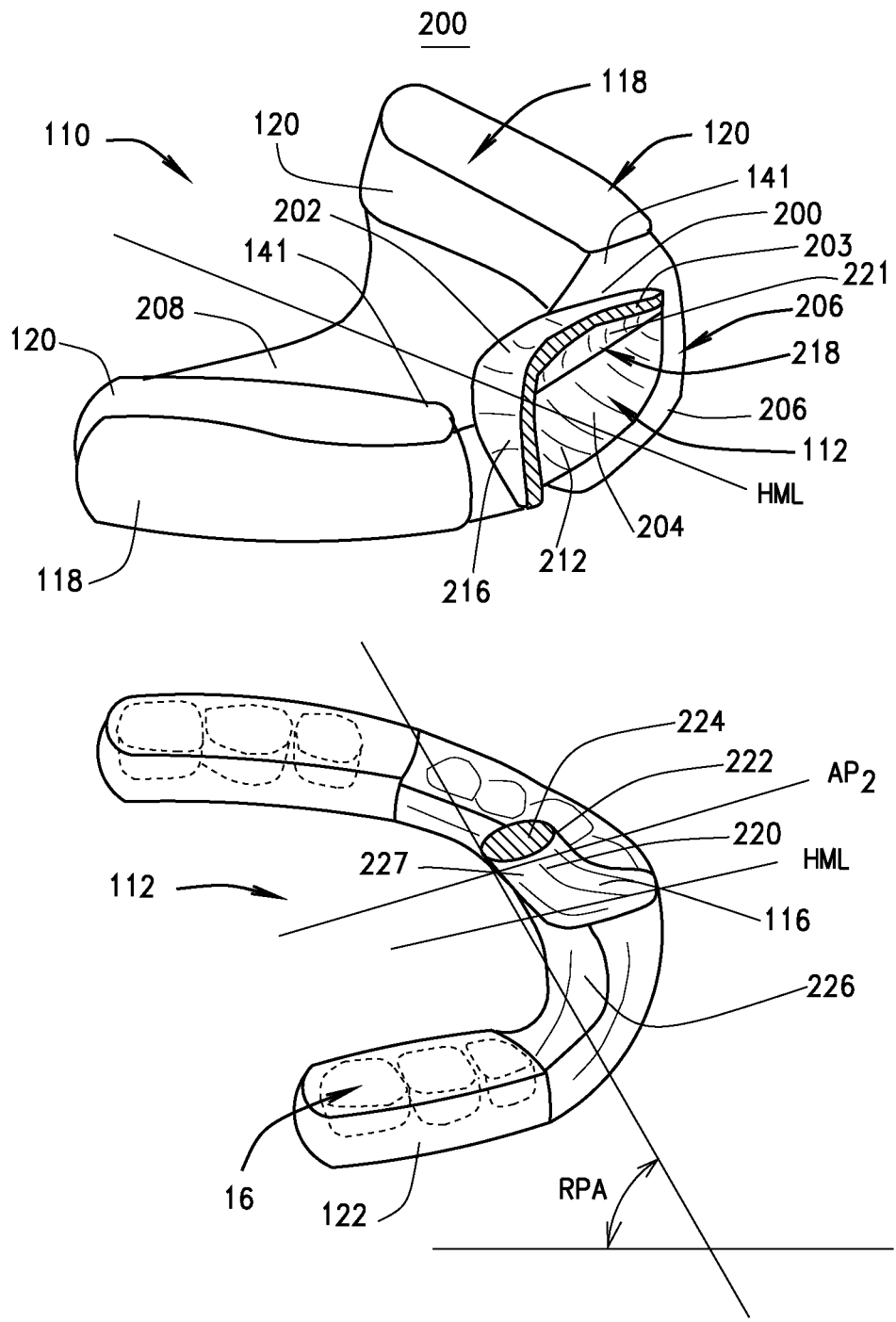
Figure 9D:
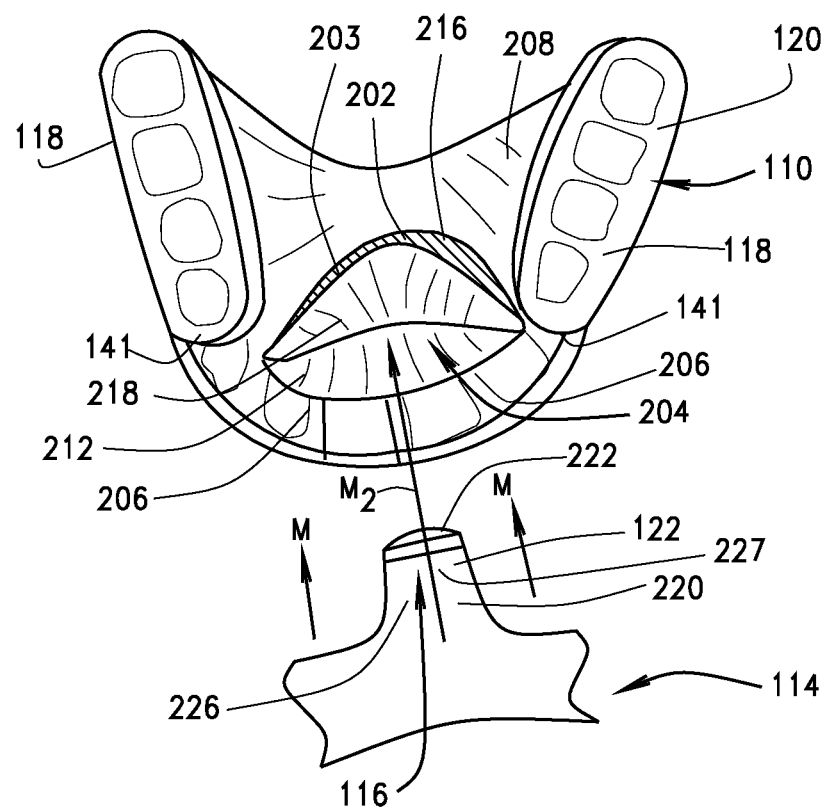

Referring now to the second exemplary embodiment as shown in FIG. 8, including FIGS. 8A-8C. This embodiment differs from the embodiment of FIG. 7 in that it has a longer vertical coupling surface VCS that is created by the lingual or palatal extension LE/PE 178 that is not in embodiment 1 of FIG. 7. The majority of the features described above with regard to the embodiment of FIG. 6 apply with several differences. FIG. 8 embodiment has a different configuration of the transition portion 109 and the structure providing the RP. In this embodiment, the RP has a negative angle RPA relative to the occlusal plane and relative to the posterior occlusion line in a posterior-anterior aspect. The length of the upper block 120 is greater creating a lingual intrusion by lingual intrusion structure 171 that has an inward lingual surface 178 and provides for a lingual extension 112' of the upper transition portion 171. In such an embodiment, if the LE 171 does not provide enough space for adequate vertical coupling the retrusion prevention portion 112 can be moved lingually to capitalize on the contour of the maxilla 12 extending into the hard plate. The LMAA 136, 138 defines the direction thereof. The LE 171 extends lingually and palatally of what would be considered a normal occlusal table. This is provided to increase the vertical coupling surface VCS of the transition portion 109, shown as transition portion extension 112' being in addition to the transition portion 112. This Lingual Extension LE 171 can also be referred to as a Palatal Extension PE as the extension from the upper transition portion 112 that lies to the lingual of the "Normal Occlusal Table". Further, in some embodiments, the LE can be formed as a structure that extends upward from the mandible 14 or the lower assembly 114 such as lower transition portion 116 that goes higher up into the palate and toward the palatal midline HML. This embodiment of the LE or PE extension rises upward from the occlusal plane OP of the mandible 14 as provided by the lower assembly 114 and also extends into the palate and toward the palatal midline HML. As such, the Palatal Extension PE or also referred herein as the LE 171, when provided, can decrease space for the tongue during use of the oral treatment assembly 100 by the patient. However, as it extends upward from the occlusal plane OP of the mandible 14, in such embodiments the LE 171 will increase the vertical contact surface VCS and in some cases, such increase can be substantial. As the VCS is increased, the transition portions 112 and 116 increases. Further, in those embodiments were lateral guidance is also a desired treatment the LMA feature can be included or adjusted and customized as well. In some embodiments, by way of example, the LE 171 can also be formed on the backside of the cuspid wherein the oral treatment assembly 100 or at least the lower assembly block 122 of the lower assembly 114 through the addition of additional assembly material such as added assembly material to the lower block 122, that can provide for increased thickness or height.

Further, as shown in FIG. 8 the lower assembly 114 and the upper assembly 110, by way of example. FIG. 8 also illustrates the LD 162 as well as a separate lower block 122, shown as block 170 that is placed in the front or anterior portion of the lower assembly 114 for providing a separate from PD 164. As compared to FIG. 7, the upper portion or surface 123 of lower block 122 is configured with an angle and surface characteristic that only provides for lateral disclusion LD 162 when contacting the upper contact control surface 160 of the upper assembly 110. In this example, the lower anterior block 170 has an upper end and an anterior surface 172 that is formed at a lower anterior guidance angle $AGA_L$. The lower anterior block 170 with these features are structured to contact with upper anterior contact control surface 174 that is formed in the front or anterior inside or lingual surface of the upper assembly 110. The upper anterior control contact surface 174 can be of any shape but often can have the same anterior guidance feature AGF having an anterior guidance AGA angle $AGA_u$ mating and providing guidance control generally at a front centered PD 164. As shown, the front lower block 170 is in the front center and raised at a height to create an interaction between the raised PD 164 formed by the above described features of the lower anterior block 170 that engages or contacts for the upper PD guidance contact surface 174.

Also as addressed as with FIG. 7 embodiment, the height or thickness of the posterior upper block 120 and possibly also or in the alternative the portions of the posterior of the lower block 122 can be configured to provide for posterior occlusion aspect POA by addition additional material for increased separation or possibly removal of material to remove posterior occlusion from occurring if such is desired.

As can be seen from FIG. 8, with the addition of the LD 162 and PD 164 structural features, that are in addition to the RP provided by the RPAs of transition portions 112, 116 and LMAA 132, 134 features, the appliance 100 has considerable features that contact and provide guidance between the lower assembly 114 and the upper assembly 110 that can provide for control of rest position as well as the movement therefrom of the patient's mandible 14 relative to the maxilla 12. The numerous combinations of treatment, control guidance features as described above can be selected and designed into the features of the embodiment of the appliance shown in FIG. 8 as should be clear to one of ordinary skill in the art after reviewing these illustrations.

Referring now to FIG. 9, including FIGS. 9A-9D, illustrate a third exemplary embodiment of assembly 200 that is identified as assembly 200 due to certain structural and operational differences. The embodiment of FIG. 9 uses a different configuration for formation of the various guidance features described herein, as discussed above, as the structural features of the present disclosure are not limited to those of the blocks 120, 122, as described above. In this embodiment, rather than the lower assembly 114 rather than having a lower block 122, 170 as in FIGS. 7 and 8, and the upper assembly 110 have an upper block 122 as disclosed therein, the lower assembly 114 has a single anterior upper block 120 that is formed as a pedestal 226 having a top end 222 with top end shaped surfaces 224 and can be positioned to have a reverse angle sloped RPA. For mating control and guidance, the upper assembly 100 includes a mating upper assembly guidance cavity 204 formed on the lingual side of the upper assembly 110 in the anterior palatal inside surface 141 thereof. The cavity 104 is formed with a downward extending skirt 200 having a wall 220 that has a lingual end or edge 203, an inner wall surface 218 and an outer wall surface 202. The skirt 200 is formed as a lingual extension from the upper palate plate portion 208. The upper bearing surface cavity skirt 200 can be dimensioned and formed to have right and left sloped bearing surfaces 212, 221 for contacting and cooperating with the lower assembly pedestal 226 and its treatment surfaces during use.

In this embodiment, the side upper block 120 and its occlusal surface 118, forms an anterior end 141 that does not form any part of the transition portion 109 and does not have a corresponding or mating surface on the lower assembly 114 or lower block 122. The upper block 120 and upper surface 118 can still be formed to provide a posterior occlusal surface or increased separation of the poster occlusive aspect POA, but does not provide for the RP or other features generally.

The same principles of structural control and guidance for various treatments apply to the embodiment 3 of FIG. 9, but the means for providing such guidance control contact surfaces are different. The lower block 122 pedestal 226 is shaped and sized and angled to cooperate in contact with the inner surfaces 212, 221 that together provides the RPA 114, 116. As the end 222 and end surface 224 of the pedestal come into contact with the inner surface 212 of the cavity 204, the mandible 14 is control along the control borders of the RPA. These upper surface 212 covers at least a portion of the hard palate of the patient and the downward upper bearing surface skirt assembly 200 is often set posterior to the maxillary incisor. Control cavity 204 is further shaped on both the right side and the left side with LMAA control shaped surface features 212 that provide for LMA border control and guidance as the mandible 14 is moved from the center position either right or left and the end 222 is guided and controlled in its lateral movements and also to move the mandible 14 downward with such lateral movement. Further, the inner wall surface 218 is also formed with a contact surface 221 to which the upper end 222 and the upper end shaping 224 or side shaping 226 are configured to provide guidance and controlled movement of the pedestal 226 during treatment use.

RP and where desired by the caregiver one or more other guidance features using the contact or bearing surfaces formed by the shapes, surfaces, contours and dimensions of the pedestal 226 and the inner surfaces 212 and 221 of the cavity 204. The selection of the guidance features as described above apply to this embodiment as well including the selection and ranges of the RPA. An additional option the is also available to this embodiment is the caregiver selection of a pedestal that prevents retrusion but that limits or restricts movement from the DTP such as only in the forward direction wherein the RPA can be defined as about a zero degrees RPA. By way of example, this can include limiting movement of the mandibular only forwards, at least initially from the static resting position, and not allowing, at least initially, any lateral movement in the right and/or left directions.

In some embodiments as shown in FIG. 9, the pedestal 226 is formed to slope backward from the anterior of the lower assembly 114 near or about the center and extends upward and can have a backward or posterior slope therefrom. To cooperate with the pedestal 226 and its treatment bearing surfaces, the upper assembly 110 includes the anterior positioned cavity 204. The anterior positioned treatment surface cavity 204. This FIG. 9 embodiment can also include, as described above with regard to the embodiments of FIGS. 7 and 8, the various treatment guidance including the RP but rather than providing such with maxillary assembly block 120 and lower assembly block 122 such are provided by the bearing treatment surfaces 224, 227 the pedestal 226 contacting, engaging and interacting with the interior bearing surfaces of the maxilla cavity 204, as may be similar to an inverted pedestal 226 and mortar 212, 221 (maxillary treatment surface cavity's 202 interior bearing surfaces).

As noted, lateral movement control or LMA can be provided by the shape of the outer surfaces 227 proximate to the end of the pedestal 226 and the shape of the contacting surfaces 212 of the cavity 204. The end 222 and end shape 224 of the pedestal 226 proximate to the end 222 can be configured to contact with shaped surfaces 221 of the wall 200 defining the cavity 204 to provide PD 164 for protrusive disclusion as well as LMA as described herein.

As shown in the exemplary embodiment, the upper assembly 114 includes upper posterior blocks 120 that can be configured by the caregiver for providing poster occlusion aspect POA by varying the amount of material therein, or that is in a lower block 122 for increasing the separation from the occlusal plane $D_{10}$ to $D_{12}$.

Another one of the differences of the design of treatment assembly 200 as compared to treatment assembly 100 as shown in two examples in FIG. 8 is that assembly 200 embodiment provides a different amount of an interference with the patient's tongue when the embodiment of FIG. 7 may be bothersome to some patients. This particular embodiment of treatment assembly 200 can be used in a treatment of a patient to retrain a patient that has a tongue thrust habit as the upper wall 202 with its upper wall surface 203 and the pedestal 226 can provide restrictions of the anterior thrust of the tongue of the patient during treatment.

As noted, these three embodiments are only examples of the assembly 100 that are available to a caregiver for providing a plurality of different treatments to a patient, all using similar assembly design methods and configurations, which can be varied to provide various combinations of treatment that are in addition to retrusion prevention, including, but not limited to mandibular advancement, lateral movement aspect LMA, anterior guidance features AGF that can include lateral disclusion LD and/or protrusive disclusion PD, lingual extension LE that increases the vertical contact surfaces, and/or posterior occlusion aspect POA.

Caregiver Design and Treatment Considerations

Figure 10:
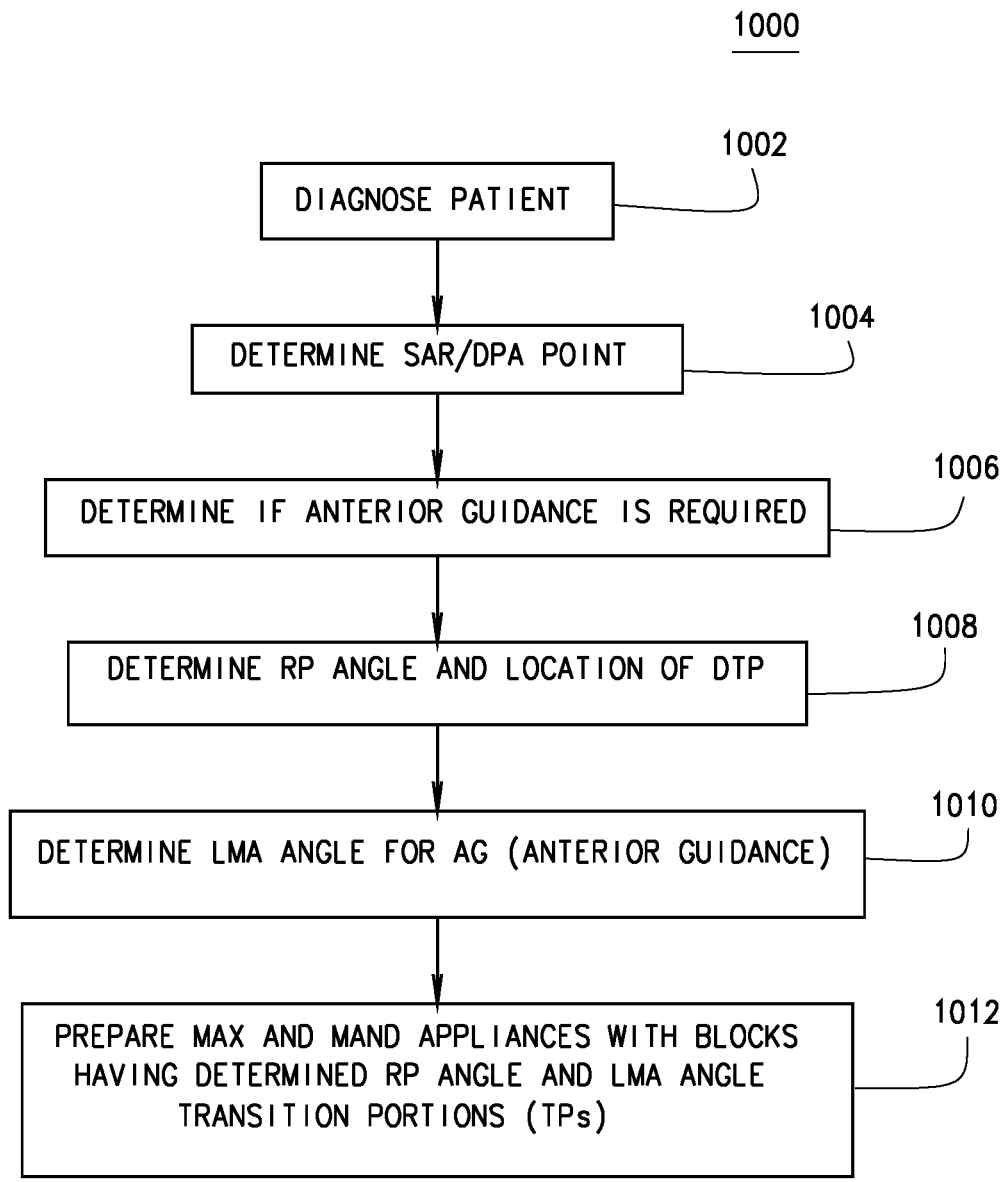
FIG. 10 is a flow diagram describing the method steps for preparation and design and fabrication of a treatment assembly that is one exemplary embodiment method according to the present disclosure.

Referring now to FIG. 10, the caregiver begins the process 1000 for determining the desired or required treatment of a patient begins in step 1002 with the diagnosis of a patient. The caregiver reviews the patient's condition and determines the desired areas of movement and the movement controls and guidance as identified above and herein. From this, as one example, as shown in step 1004, the MI as well as possibly the SAR, or DTA, can be used as the determined treatment starting point DTP. The caregiver then determines the areas of movement therefrom, such as if anterior guidance is required, such as shown by way of example in step 1006. Next or prior to step 1006, a RPA is determined as well as the location of the DTP as shown in step 1008. The caregiver then can determined from the DTP, if anterior guidance is desired by the assembly 100, the appropriate LMAA to provide such AG or control of lateral movements as described above, in step 1010. Additionally, while not shown in FIG. 10 or process 1000, each of the additional guidance features that can be provided by the assembly 100 for the patient are also determined. This can include the various combinations of Appliance Guidance Combinations AGC as disclosed and addressed above. Finally, after the selection of the AGC and the various angles and dimensions are determined as necessary to provide the caregiver selected AGCs, the caregiver has the assembly 100 prepared in steps 1012 which would include the preparation of the treatments assemblies 100 for the mandible 14 and the maxilla 12, lower assembly 114 and upper assembly 110. This can include, such as in the exemplary embodiments of FIGS. 7 and 8, the lower assembly block 122 and upper assembly block 120 of such oral treatment assembly 100s, or of embodiment FIG. 9 that includes the features and surfaces of the pedestal 226 and the cavity 204 that have the determined RPA and LMAAs and the transition portion 109 formed thereon as may be applicable.

Method of Use by a Patient

Figure 11:
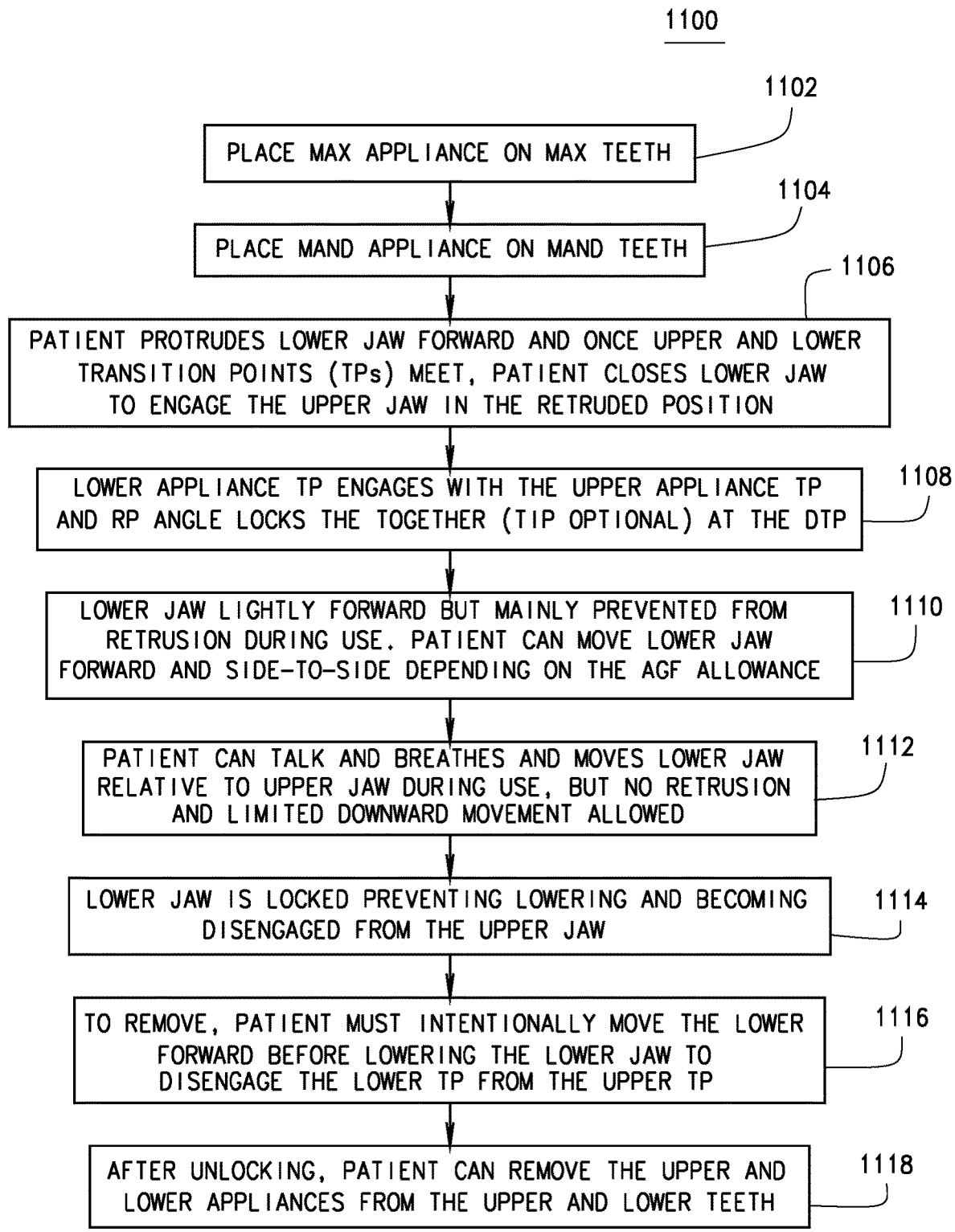
FIG. 11 is a flow diagram describing the method of use of a treatment assembly wherein the assembly is formed and that includes placement, use and removal by the patient during treatment according to the present disclosure.

FIG. 11 provides a method of use or operation 1100 by a patient after such is made by a caregiver of the patient as described above by way of one example with regard to FIG. 10. An oral treatment assembly 100 disallows retrusion upon placement of the oral treatment assembly 100s onto the respective maxillary teeth 18, the maxilla 12 and the lower teeth 16 the mandible 14 as in processes 1102 and 1104, respectively. In some embodiments of assembly 100, one or more maxillary teeth 18 and one or more mandibular teeth 16, the patient muscularly protrudes their mandible 14 and then upward to engage the treatment assembly to place the predetermined DTP treatment position as in steps 1106 and 1108. This engages the upper transition portion 112 of the upper assembly 110 to the lower transition portion 116 of the lower assembly 114 of the oral treatment assembly 100. Once in the DTP, the treatment assembly 100 is worn by the patient retains the mandible 14 in the DTP or AP position as the rest or default position as in step 1110, but also provides the patient with the ability to move the mandible 14 but only in controlled movements as to direction and extent of movement as predetermined by the patient's caregiver as in Step 1112. The user can disengage the lower assembly 114 from the upper assembly 110 by moving the mandible 14 forward and downward sufficient to disengage the lower transition portion 116 from the upper transition portion 112 as in step 1112. The mandible 14 becomes disengaged in process 1114. After disengagement in process 1114, the patient can reengage the lower transition portion 116 to the upper transition portion 112 by moving the mandible 14 forward and upward as in step 1116. In the alternative, after disengagement (also referred herein as "uncoupling"), in process 1118 the patient can remove the upper assembly 110 and the lower assembly 114 from the upper teeth 18 and lower teeth 16, respectively to remove treatment assembly 100/200.

Use of the treatment assembly 100/200 can be at any time, but in some embodiments, due to the restrictions on movement, a common treatment use of the treatment assembly will be for night time use by the patient. For example, during use of the treatment assembly, talking and chewing and other forms of mastication of the patient will likely be very difficult.

As will be appreciated by patient caregivers, the presently disclosed treatment assembly can be design, manufactured and used by patient caregiver for any treatment determined for patient is desired where the goal of the treatment and use is the control of the mandibular condyles. These methods of treatment use can include, but are not limited to, TMJ joint stabilization, controlled positional TMJ joint healing, patient airway stabilization, and training or retraining of the musculature involved in a lateral disclusion slide.

Summary of Benefits Over the Prior Art

The various features of the design and use for treatment of patient conditions as described are flexibly identifiable by the caregiver based on the disclosure provided herein and are intended to provide the caregiver with flexible treatment assembly and method for treatment of numerous patient conditions.

Generally, as described, the treatment assembly and method of treatment provided thereby provides for retrusion prevention using a transition portion that has a negative angle that is an improvement over the prior art that used a forward angle and that is an improvement to that generally accepted in the industry prior to the present invention which was the amount of protrusion of the mandible 14 provided by the treatment assembly. Further, the present design of focusing on retrusion prevention rather than protrusion advancement enables the present assemblies and methods of use to provide further treatment options to the caregiver including providing the treatment assembly with a transition portion that allows for movement within a treatment movement area while being "retained" in the determined treatment position. It also provides for adding further angles relative to the maxillary midline HML for providing placement and restricted movement within Posselt's movement borders for the lateral aspect. In this flexible design, the numerous available configurations provides a caregiver the ability to provide further customization through a mandibular extension ME of the lower transition portion 116 that can extend to the maxillary occlusal surface if the caregiver determines for a particular patient that there is not enough overlap in the lower transition portion 116 to keep it held in place with the upper transition portion 112 or otherwise engaged. In such an embodiment, the mandibular extension ME can be extended upward higher into the palate. Further, such embodiments of the treatment assembly can include a maxillary "LE" lingual extension where the upper block 120 extends toward the maxillary midline HML, and is "wider" than the normal facial-lingual width of maxillary teeth 18. In such embodiments, the wider LE of the upper assembly 110 provides for the mandibular extension ME with more vertical height for enhanced connection or engagement that can be enhanced to minimize and sometimes prevent unintended decoupling during use. Additionally, in some embodiments, the treatment assembly can be further customized to control and provide anterior guidance AG, which can include a lateral movement aspect LMA as well as a selection by the caregiver as to which teeth touch or contact during either a protrusive or an anterior movement as well as during lateral movement.

As will be known to those of skill in the art after reviewing and understanding the present disclosure, there are numerous benefits that the present treatment assemblies can provide. These can include, in some embodiments, the combination of retrusion prevention, condylar travel control and control of the occlusion, the oral treatment assemblies have applications for preventing TMJ joint compression or decompressing TMJ joint components, and controlled condylar placement and restricted condylar movement can relate to hard and/or soft tissue TMJ stabilization. This can also include holding certain airways "open" as related to mandibular position and mandibular movement control, prevent airway collapse as related to mandibular retrusion and lack of vertical dimension of occlusion, counteract compressive or retrusive CPAP facemask forces applied to a TMJ, and treat certain types of sleep apnea as related to mandibular positioning. These can also include treating bruxism through the neuro-feedback loop of anterior guidance, lateral guidance and protrusive guidance while disallowing posterior occlusal interference, allow or disallow condylar side shift, disallow pathological or nontraditional "Posselt's" border movements or determine and allow certain Posselt's border movements in an effort to treat mandibular condyles, glenoid fossas or retrain the muscle memory of lateral movement musculature. Also these can include increased vertical dimension of occlusion to elongate certain muscles of mastication for use in a night time therapeutic trial. In some cases, the treatment assemblies can be used in sports as a "knockout" prevention and protection assembly in contact and combat sports by interfering with the mandible 14 and mandibular transfers of impact energy onto the cranial base or the maxillary occlusal surfaces. As will be understood by those of skill in the art, these benefits can also include improved jaw positioning, and neck related benefits of jaw positioning such as neck generated headache treatment and prevention.

When describing elements or features and/or embodiments thereof, the articles "a", "an", "the", and "said" are intended to mean that there are one or more of the elements or features. The terms "comprising", "including", and "having" are intended to be inclusive and mean that there may be additional elements or features beyond those specifically described.

Those skilled in the art will recognize that various changes can be made to the exemplary embodiments and implementations described above without departing from the scope of the disclosure. Accordingly, all matter contained in the above description or shown in the accompanying drawings should be interpreted as illustrative and not in a limiting sense.

It is further to be understood that the processes or steps described herein are not to be construed as necessarily requiring their performance in the particular order discussed or illustrated. It is also to be understood that additional or alternative processes or steps may be employed.

What is claimed is:

1. An oral treatment assembly providing jaw control during use, comprising:
   an upper assembly comprising:
      an upper posterior portion having an upper posterior occlusal surface, and an upper anterior portion having an upper anterior occlusal surface said upper posterior portion defining an upper posterior part and a lower posterior part; said lower posterior part defining an upper block that extends downward from an axial plane of a bite surface of a user's upper teeth such that the upper posterior occlusal surface is below the upper anterior occlusal surface;

an anterior facing end of said upper block extending from the upper anterior occlusal surface to the upper posterior occlusal surface;

wherein, said anterior facing end defines an upper transition portion having a sloped upper transition surface with an upper reverse angle such that a lower anterior edge of the sloped upper transition surface is forward of an upper posterior edge of the sloped transition surface; the upper anterior portion extending from the upper posterior part of the upper posterior portion;

a lower assembly comprising:

a lower posterior portion having a lower posterior occlusal surface;

a lower anterior portion having a lower anterior occlusal surface, a lower block that extends upward from the lower anterior occlusal surface, said lower block being positioned forward of said upper block when said upper and lower assemblies are positioned in a user's mount, a posterior face of said lower block defining a lower transition portion having a sloped lower transition surface having a lower reverse angle such that a lower anterior edge of the sloped lower transition surface is forward of an upper posterior edge of the sloped lower transition surface; wherein the lower posterior portion extends from a lower end of said lower transition surface and wherein the lower posterior portion is sized and shaped such that it does not extend above the lower block;

wherein the lower transition portion is configured to selectively couple to the upper transition portion and wherein the lower sloped transition surface and the upper sloped transition surface are configured to selectively engage when the user of the oral treatment assembly extends a mandible jaw forward by a predetermined distance at which point the lower assembly engages the upper assembly at a predetermined relationship, and wherein when the upper and lower assemblies are engaged, the upper block registers with the lower posterior portion of the lower assembly and the lower block of the lower assembly registers with the upper anterior portion of the upper assembly.

2. The oral treatment assembly of claim 1 wherein
the upper assembly includes a right cavity for receiving a plurality of upper teeth on a right side of a user's maxilla and a left cavity for receiving a plurality of teeth on a left side of the user's maxilla, with the upper posterior occlusal surface positioned about the crown the received plurality of the received upper teeth, and
the lower assembly includes a right cavity for receiving a plurality of lower teeth on a right side of the mandibular and a left cavity for receiving a plurality of teeth on a left side of the mandibular, with the lower posterior occlusal surface positioned about the received lower teeth.

3. The oral treatment assembly of claim 2 wherein the upper assembly includes a right upper transition portion and a left upper transition portion and the lower assembly includes a right lower transition portion and a left lower transition portion, and the right upper and lower transition portions form a right transition portion and the left upper and lower transition portions form a left transition portion.

4. The oral treatment assembly of claim 3 wherein the right upper and lower transition portions have a right reverse angle and the left upper and lower transition portions have a left reverse angle, and wherein the right reverse angle is different than the left reverse angle.

5. The oral treatment assembly of claim 3 wherein the right upper and lower transition portions have a right reverse angle and the left upper and lower transition portions have a left reverse angle, and wherein the right reverse angle is the same as the left reverse angle.

6. The oral treatment assembly of claim 2 wherein the upper assembly is a tray defining the right and left cavities for receiving the plurality of maxillary teeth on each side and the lower assembly defines a lower tray defining the right and left cavities for receiving the plurality of mandibular teeth on each side.

7. The oral treatment assembly of claim 2 wherein the upper assembly and the lower assembly are each trays configured to have a u-shaped arch for receiving the plurality of teeth and forming the downward extended upper block of the upper assembly and the upward extending lower block of the lower assembly and the upper and lower transition portions.

8. The oral treatment assembly of claim 7 wherein the upper and lower trays are formed from an acrylic by molding.

9. The oral treatment assembly of claim 1 wherein the downward extended upper block registers with the lower posterior portion of the lower assembly and the lower block registers with the upper anterior portion of the upper assembly forming a new occlusal surface by the contacting there between.

10. The oral treatment assembly of claim 1 wherein the upper sloped transition surface and the lower sloped transition surface are each sloped from their respective upper and lower edges at an angle from an occlusal plane elected from a group of angles consisting of a) about 60 degrees, b) between about 22 degrees to about 90 degrees; c) less than 90 degrees; and d) between about 30 degrees and 89 degrees.

11. The oral treatment assembly of claim 10 wherein the upper and lower transition portions are positioned relative to the interproximal area selected from the group consisting of between the cuspid and the first bicuspids, between the first and second bicuspids, proximal to the distal of the maxillary cuspid, between the molar and the first pre-molar, and between the first and second pre-molars.

12. The oral treatment assembly of claim 1 wherein an upper end of the upper block is shaped downward from a lingual side to a buccal side, and the upper block includes an interior surface shaped to provide lateral disclaimer and configured for engaging with the shaped upper end of the upper extending block for providing lateral guidance between the upper assembly and the lower assembly during treatment.

13. The oral treatment assembly of claim 1, further comprising a protrusive discluder (PD) for providing protrusive disclusion, with the protrusive discluder having a structure that is placed on or about a cuspid, a lateral incisor, or a central incisor and is formed on a top end of the lower block and at an inner contact surface of the upper assembly, or can be an upward extension of the lower transition portion that extends apical or toward a root or a hard plate as compared to a natural occlusal plane of a maxilla.

14. The oral treatment assembly of claim 1 wherein the upper and lower transition portions are positioned proximate to the cuspids.

15. The oral treatment assembly of claim 1 wherein the upper and lower transition portions are positioned relative to the cuspids and the first cuspids.

16. The oral treatment assembly of claim 1 wherein the lower block having an upper end defining an lower anterior surface have a lower anterior surface angle, and
wherein the upper assembly has an anterior contact control surface formed on an inside surface of the upper anterior portion and configured for contacting with the upper anterior surface of the lower block for providing anterior guidance as a function of the lower anterior surface angle.

17. The oral treatment assembly of claim 1 wherein the sloped upper and lower transition surfaces of the upper transition portion and the lower transition portion are each further angled outward from a buccal side of the upper and lower transition portions to a lingual side at angles from respective midlines of each of the upper and lower assemblies to define outward angles, wherein the outward angles are defined by the respective midline and a respective perpendicular to each midline.

18. The oral treatment assembly of claim 17 wherein the outward angle of the upper transition portion and the lower transition portion are each between about 30 degrees from each respective midline to about 90 degrees from the respective midlines of each of the upper and lower assemblies.

19. The oral treatment assembly of claim 17 wherein the upper transition portion and the lower transition portion each have an outward angle of about 30 degrees from each respective midlines of each of the upper and lower assemblies.

20. The oral treatment assembly of claim 1 wherein the sloped upper and lower transition surfaces of the upper transition portion and the lower transition portion are each further outwardly angled from the buccal side of each transition portion to the lingual side and side edges of the buccal sides of the upper and lower transition portions are set back towards the posterior relative to the lingual side edges.

21. The oral treatment assembly of claim 1 wherein the sloped upper and lower transition surfaces of the upper transition portion and the lower transition portion are each further outwardly angled from the buccal side of the transition portion to the lingual side and side edges of the buccal sides of the upper and lower transition portions are set forward towards the anterior relative to the side edges of the lingual sides.

22. The oral treatment assembly of claim 17 wherein the upper transition portion and the lower transition portion are each perpendicular to a midline from the buccal side edges of the transition portion to side edges of the lingual sides.

23. The oral treatment assembly of claim 1 wherein the sloped upper and lower transition surfaces of the upper transition portion and the lower transition portion are each further outwardly angled from the buccal side of the transition portion to the lingual side at an angle that is less than 90 degrees from the midline, wherein side edges of the buccal sides of the transition portions and are set forward towards the anterior relative to the side edges of the lingual sides of the transition portions.

24. The oral treatment assembly of claim 1 wherein the downward extended block of the upper assembly, the upward extending block of the lower assembly, the location of the upper and lower transition portions and the angles of the upper and lower transition portions are configured for the patient for control of one or more of the following:
a. condylar translation;
b. condylar rotation
c. condylar side shift;
d. Posselt's lateral and/or opening movements;
e. retrusion prevention;
f. lateral guidance, including disclusion angle;
g. anterior guidance, including disclusion angle;
h. anterior posterior condylar position; and
i. condylar decompression, vertical dimension of occlusion.

25. The oral treatment assembly of claim 1 wherein the upper anterior portion of the upper assembly is formed to substantially conform with and enclose anterior upper teeth substantially along an axial plane of the anterior upper teeth and the upper posterior portion forming the downward extended block is formed to extend downward from an axial plane of the posterior maxilla teeth; and wherein the lower anterior portion of the lower assembly is formed to extend upward from an axial plane of the enclosed anterior lower teeth and the lower posterior portion of the lower assembly is formed to enclose the anterior lower teeth substantially along an axial plane of the mandibular teeth.

26. The oral treatment assembly of claim 1 wherein the downward extended upper block of the upper assembly is defined by right and left upper assembly blocks that define (1) right and left upper transition portions having right and left upper reverse angles on anterior portions of the right and left upper assembly blocks and 2) posterior occlusal surfaces that extend from the right and left upper transition portions to a posterior end of the upper assembly, and
wherein the lower block of the lower assembly is defined by right and left lower assembly blocks that define right and left lower transition portions and have right and left lower reverse angles on anterior portions of the right and left lower assembly blocks.

27. The oral treatment assembly of claim 26 wherein each of the upper assembly and lower assembly blocks further define a lateral movement angle (LMA) that is defined by a centerline of a maxilla within a mouth cavity of the user, the lateral movement angle (LMA) being less than or equal to about 90 degrees whereby no lateral guidance or control is provided except for nontraditional Posselt's movement, or being less than 90 degrees and wherein lateral guidance or control of movement between the lower assembly and the upper assembly is provided.

28. The oral treatment assembly of claim 1 wherein the upper block is selectively attached to the upper assembly and the lower block is selectively attached to the lower assembly each by a selective attachment feature.

29. The oral treatment assembly of claim 1 wherein at least one of the upper sloped transition surface and the lower sloped transition surface includes a surface texture that, when the upper transition portion and the lower transition portion are in contact with each other, an increased friction between the upper and lower sloped transition surfaces is provided.

30. The oral treatment assembly of claim 1 wherein a downward extended distal end of the upper transition portion and an upward extended distal end of the lower transition portion each include at least a lip or an end retention or mating feature or catch for providing an increased coupling when the upper and lower assemblies are engaged or physically coupled.

31. The oral treatment assembly of claim 1 wherein the upper and lower assemblies and the upper and lower transition portions are configured and positioned for one or more of the following:
  a. relaxing musculature;
  b. controlling of retrusive forces;
  c. limiting retrusive forces and thereby limiting the force applied to the temporomandibular condyle and joint;
  d. enabling the forward movement or advancement of the mandibular relative to the maxilla by the user during use;
  e. controlling condylar movement as it relates to Posselt's movements;
  f. engaging lateral guidance in the cuspid and first bicuspid to reduce muscular contraction during movement;
  g. engaging anterior guidance to reduce muscular contraction during movement; and
  h. lengthening over closed musculature relative to vertical dimension.

32. The oral treatment assembly of claim 1 wherein the upper and lower transition portions can be configured to be laterally angled to be tangential to the arch of the teeth proximate to the upper and lower transition portions as a function of an amount of predetermined required condylar control.

33. The oral treatment assembly of claim 27 wherein the lateral movement angle (LMA) is angled outward from a buccal side of each transition portion to a lingual side to define lateral movement angles from a midline of each of the upper and lower assemblies with the lateral movement angle (LMA) of the upper and lower transition portions being less than 90 degrees to about 30 degrees.

34. The oral treatment assembly of claim 1 wherein the upper block extends from a posterior end of the upper assembly forward in the anterior direction to an anterior end of the upper block defining the upper transition portion, the upper transition portion being positioned relative to an interproximal area of the maxilla selected from the group consisting of between the cuspid and the first bicuspids, between the first and second bicuspids, proximal to the distal of the maxillary cuspid, between the molar and the first pre-molar, and between the first and second pre-molars.

35. The oral treatment assembly of claim 1 wherein the upper and lower assemblies have right and left transition portions, wherein the only one of the right and left transition portions is configured with a lateral movement angle (LMA) that is less than an angle between its respective midline and the perpendicular thereof, with the other of the right and left transition portions defines an angle that is equal to or greater than the angle between its respective midline and a perpendicular thereof.

36. The oral treatment assembly of claim 1 wherein the upper block further includes an inward intrusion structure that extends lingually as a lingual intrusion with an inward lingual surface that extends the upward sloped surface of the upper transition portion lingually for engaging with the lower sloped surface of the lower transition portion and configured to provide decreased space for a tongue of a user during use of the oral treatment assembly.

37. An oral treatment assembly providing jaw control during use, comprising:
  an upper assembly comprising:
    an upper posterior portion having an upper posterior occlusal surface,
    an upper anterior portion having an upper anterior occlusal surface;
    the upper posterior portion defining an upper posterior part and a lower posterior part; said lower posterior part defining an upper block that extends downward from an axial plane of a bite surface of a user's upper teeth such that the upper posterior occlusal surface is below the upper anterior occlusal surface;
    the upper posterior portion being coupled by an upper part of said upper posterior portion to said upper anterior portion,
    block defining an upper transition portion on an anterior facing end having an upper sloped surface with an upper reverse angle such that a lower anterior edge of the upper transition portion is forward of an upper posterior edge of the upper transition portion;
  a lower assembly comprising:
    a lower posterior portion and a lower anterior portion,
    a lower block that extends upward in a direction of the incisors and that extends upward from an anterior mandibular bite surface of the anterior portion and wherein said posterior portion does not extend upward above the lower block,
  the lower block being coupled to the lower posterior portion by a lower transition portion coupling the lower block to the lower posterior portion by a lower sloped surface having a lower reverse angle whereby the lower block extends in a posterior direction and over a portion of a non-extended posterior portion,
  the lower transition portion being configured to selectively couple to the upper transition portion and wherein the lower sloped surface of the lower transition portion and the upper sloped surface of the upper transition portion are configured to selectively engage when the user of the upper and lower assemblies extends a mandible jaw forward by a predetermined distance at which point the upper sloped surface and the lower sloped surface selectively engage; the lower assembly is at a predetermined relationship relative to the upper assembly, wherein when selectively positioned for mating, the upper block registers with the posterior portion of the lower assembly and the lower block registers with the anterior portion of the upper assembly;
  wherein the upper transition portion and the lower transition portion are each further angled outward from a buccal side of each transition portion to a lingual side at lateral movement angles from a midline of each of the upper and lower assemblies to form a lateral movement angle (LMA) of the upper and lower transition portions, wherein the outward lateral movement angle (LMA) is less than an angle between each respective midline and a perpendicular thereof and is configured for controlling the lateral movement of the upper assembly relative to the lower assembly when the upper transition portion is engaged with the lower transition portion.

* * * * *